United States Patent
Godefroy et al.

(10) Patent No.: US 9,395,368 B2
(45) Date of Patent: Jul. 19, 2016

(54) METHODS, AGENTS AND PEPTIDES FOR INDUCING AN IMMUNE RESPONSE TO MATRIX METALLOPROTEINASE-2 EXPRESSING TUMORS

(71) Applicants: Emmanuelle Godefroy, New York, NY (US); Francine Jotereau, Carquefou (FR); Nina Bhardwaj, West Orange, NJ (US)

(72) Inventors: Emmanuelle Godefroy, New York, NY (US); Francine Jotereau, Carquefou (FR); Nina Bhardwaj, West Orange, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/914,112

(22) Filed: Jun. 10, 2013

(65) Prior Publication Data
US 2014/0030216 A1 Jan. 30, 2014

Related U.S. Application Data

(62) Division of application No. 12/930,592, filed on Jan. 11, 2011, now Pat. No. 8,481,477.

(60) Provisional application No. 61/335,765, filed on Jan. 12, 2010.

(51) Int. Cl.
| | |
|---|---|
| *G01N 33/569* | (2006.01) |
| *A61K 38/20* | (2006.01) |
| *A61K 39/00* | (2006.01) |
| *C12N 9/64* | (2006.01) |
| *G01N 33/574* | (2006.01) |
| *A61K 38/00* | (2006.01) |

(52) U.S. Cl.
CPC ........ *G01N 33/56977* (2013.01); *A61K 38/208* (2013.01); *A61K 39/0011* (2013.01); *C12N 9/6491* (2013.01); *G01N 33/5743* (2013.01); *A61K 38/005* (2013.01); *A61K 2039/572* (2013.01); *C07K 2319/01* (2013.01); *C07K 2319/33* (2013.01); *C07K 2319/55* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,585,356 | A | 12/1996 | Liotta et al. |
| 6,184,022 | B1 | 2/2001 | Seiki et al. |
| 2002/0031817 | A1 | 3/2002 | Falduto et al. |
| 2007/0264275 | A1 | 11/2007 | Guilloux et al. |
| 2010/0003336 | A1 | 1/2010 | Deming et al. |

FOREIGN PATENT DOCUMENTS

| | | |
|---|---|---|
| WO | 0180811 | 11/2001 |
| WO | 02098351 | 12/2002 |
| WO | 2005000342 | 1/2005 |
| WO | 2008035350 | 3/2008 |

OTHER PUBLICATIONS

Su et al, Cancer Res 63:600-607, 2003).*
Yi et al, Cancer Gene Therapy 14:158-164, 2007.*
Smith et al, Immunology, 165:3136-3144, 2000.*
Benlalam et al., "Identification of five new HLA-B*3501-restricted epitopes derived from common melanoma-associated antigens, spontaneously recognized by tumor-infiltrating lymphocytes", The Journal of Immunology, 2003, vol. 171, pp. 6283-6289.
Brooks et al., Localization of matrix metalloproteinase MMP-2 to the surface of invasive cells by interaction with integrin alpha v beta3, Cell, 1996, vol. 85, pp. 683-693.
Brooks et al., "Disruption of angiogenesis by PEX, a noncatalytic metalloproteinase fragment with integrin binding activity", Cell, 1998, vol. 92, pp. 391-400.
Coulie et al., "T-cell responses of vaccinated cancer patients", Curr Opin Immunol, 2003, vol. 15, pp. 131-137.
Godefroy et al., "Alpha v beta3-dependent cross-presentation of matrix metalloproteinase-2 by melanoma cells gives rise to a new tumor antigen", J Exp Med, 2005, vol. 202, pp. 61-72.
Godefroy et al., "MMP-2: a novel target for antitumor immune therapy", Journal of Clinical Oncology, ASCO Annual Meeting Proceedings, 2009, vol. 27, No. 15S, 3053 (Abstract Only).
Godet et al., MELOE-1 is a new antigen overexpressed in melanomas and involved in adoptive T cell transfer efficiency, J Exp Med, vol. 205, No. 11, pp. 2673-2682.
Khammari et al., "Long-term follow-up of patients treated by adoptive transfer of melanoma tumor-infiltrating lymphocytes as adjuvant therapy for stage III melanoma", Cancer Immunol Immunother, 2007, vol. 56, pp. 1853-1860.
Khammari et al., "Treatment of metastatic melanoma with autologous melan-A/mart-1-specific cytotoxic T lymphocyte clones", Journal of Investigative Dermatology, 2009, vol. 129, pp. 2835-2842.
Nielsen et al., "MHC class II epitope predictive algorithms", Immunology, 2010, vol. 130, pp. 319-328.

(Continued)

*Primary Examiner* — Lei Yao
(74) *Attorney, Agent, or Firm* — Klauber & Jackson LLC

(57) ABSTRACT

The present invention relates to enhancing, modulating or stimulating the immune response to MMP-2 expressing tumors, including melanoma, and to the modulation and application of immune modulators and MMP-2 peptides for melanoma or other MMP-2 expressing tumor vaccines. The invention provides methods and means to activate an effective response to MMP-2 expressing tumors and modulate the ability of MMP-2 to skew CD4+ T cell responses toward that of $T_H2$ cells, which are less effective mediators of tumor cell clearance than $T_H1$ cells. Methods and assays are provided for screening for compounds, agents, or peptides capable of enhancing or activating immune responses, particularly to melanoma.

11 Claims, 30 Drawing Sheets

(56) References Cited

OTHER PUBLICATIONS

Su et al., "Active immunogene therapy of cancer with vaccine on the basis of chicken homologous matrix metalloproteinase-2", Cancer Research, 2003, vol. 63, pp. 600-607.
Vignard et al., "Adoptive transfer of tumor-reactive melan-A-specific CTL clones in melanoma patients is followed by increased frequencies of additional melan-A-specific T cells", The Journal of Immunology, 2005, vol. 175, pp. 4797-4805.
Herman et al., "Tissue factor pathway inhibitor-2 is a novel inhibitor of matrix metalloproteinases with implications for atherosclerosis", J Clin Inves, 2001, vol. 107, pp. 1117-1126.
Stevanovic, "Identification of tumour-associated T-cell epitopes for vaccine development", Nature Reviews, 2002, vol. 2, pp. 1-7.
Harig et al., "Induction of cytotoxic T-cell responses against immunoglobulin V region-derived peptides modified at human leukocyte antigen-A2 binding residues", Blood, 2001, vol. 98, pp. 2999-3005.

* cited by examiner

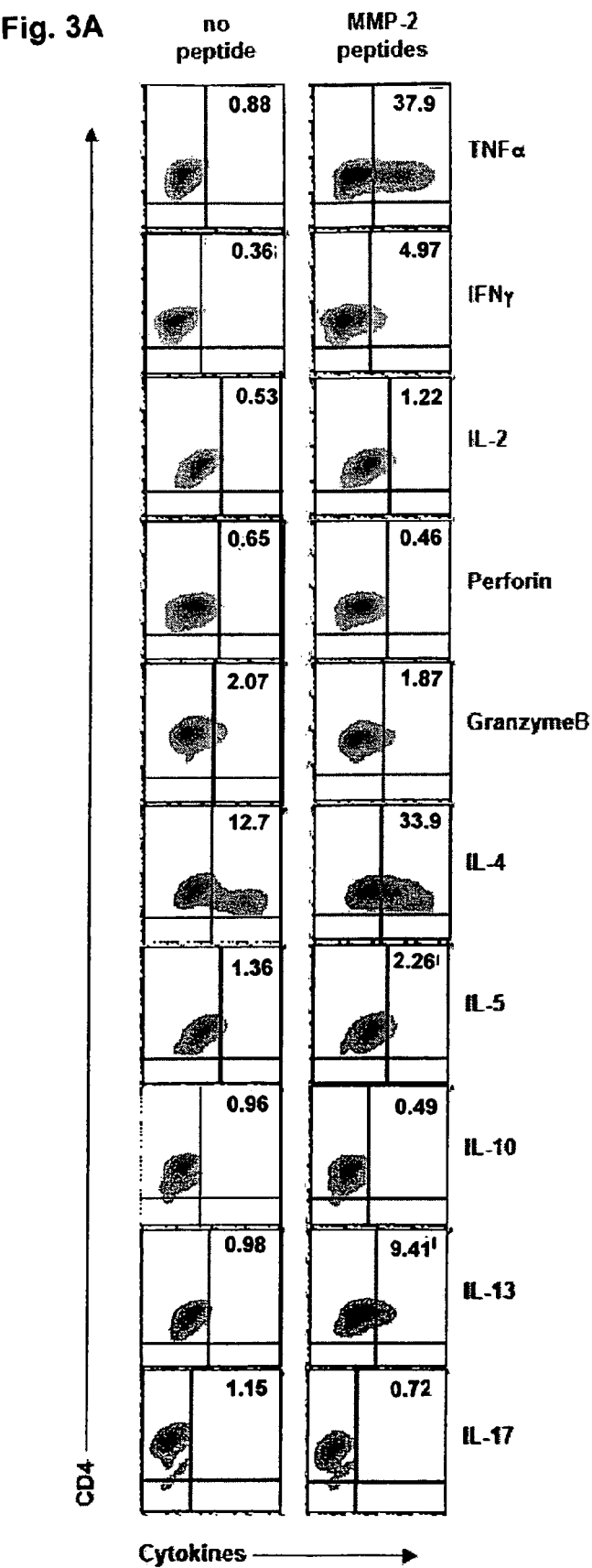

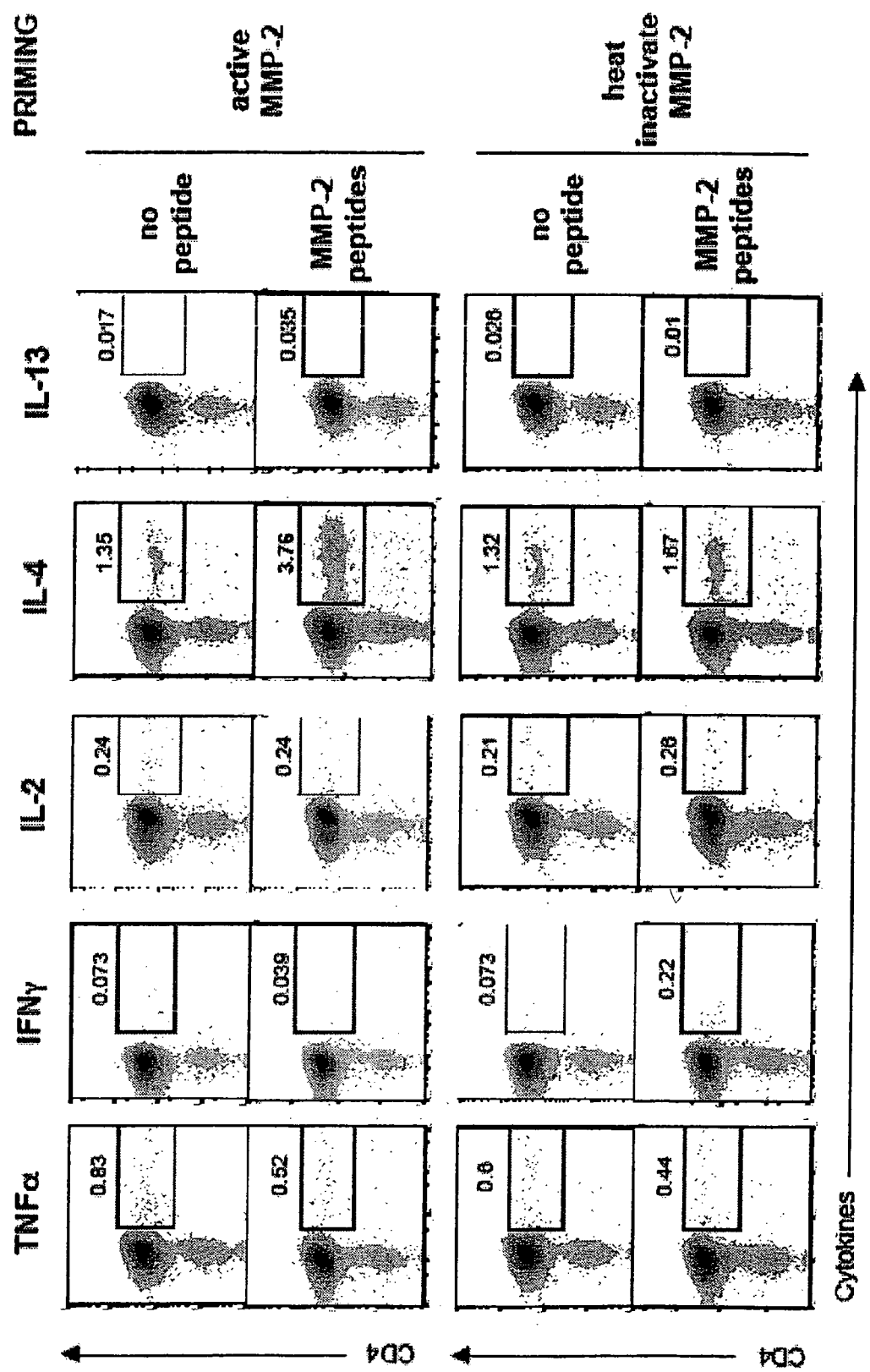

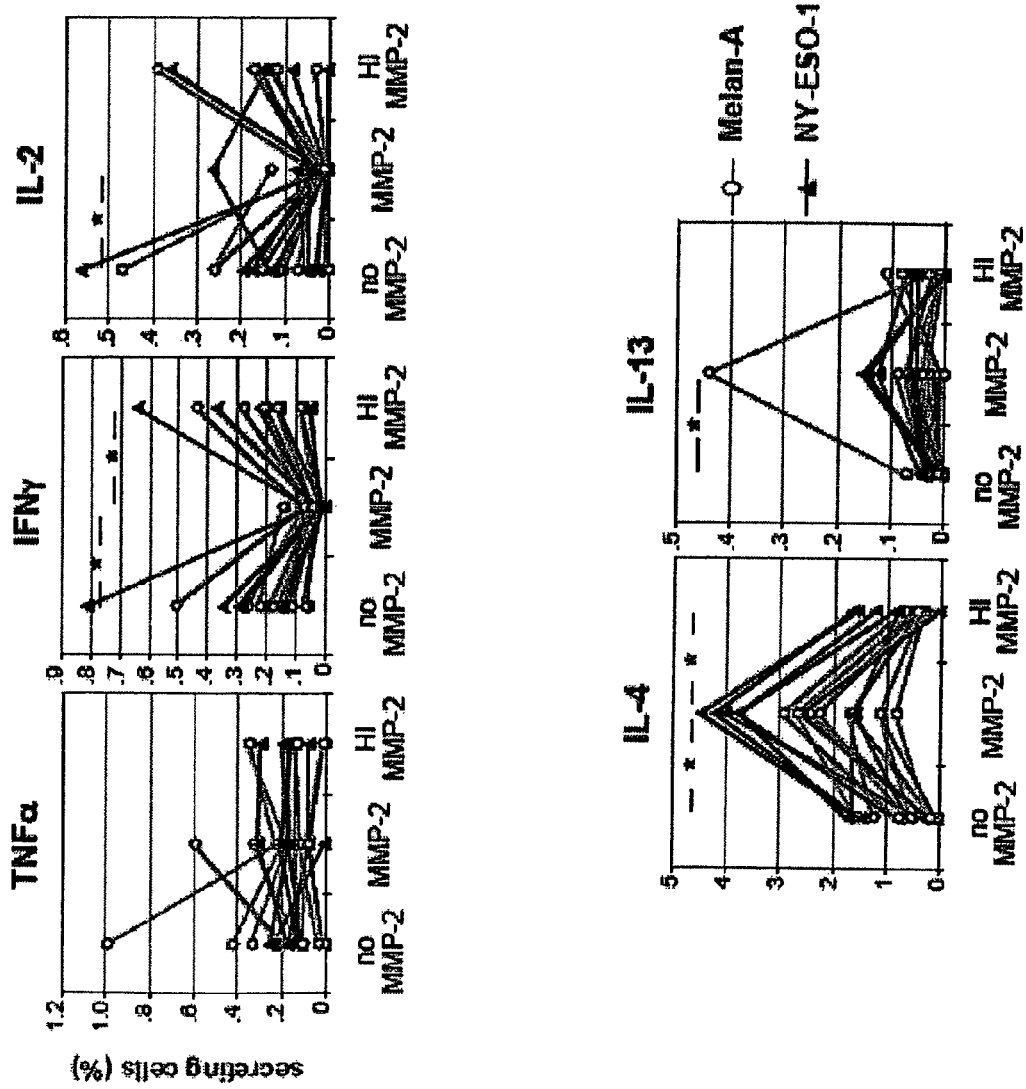

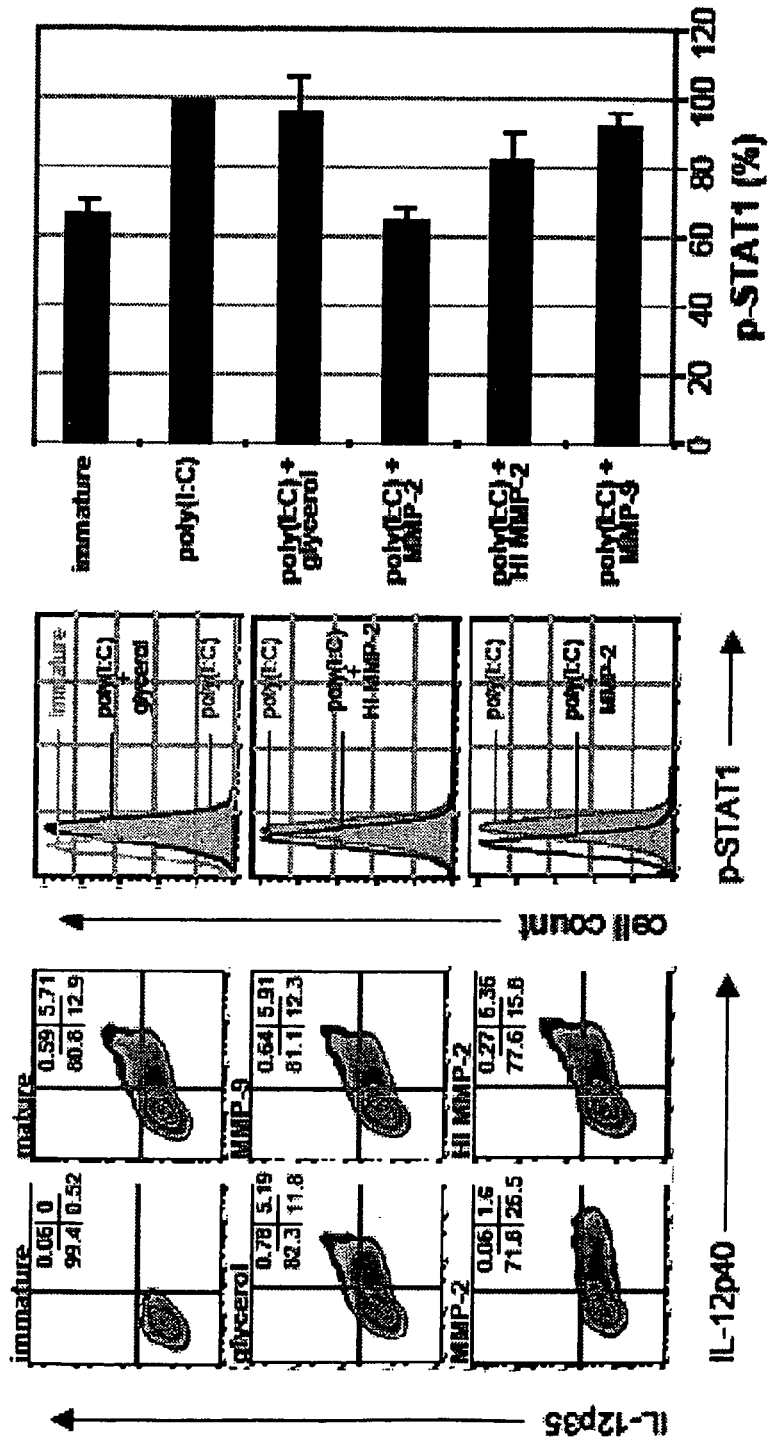

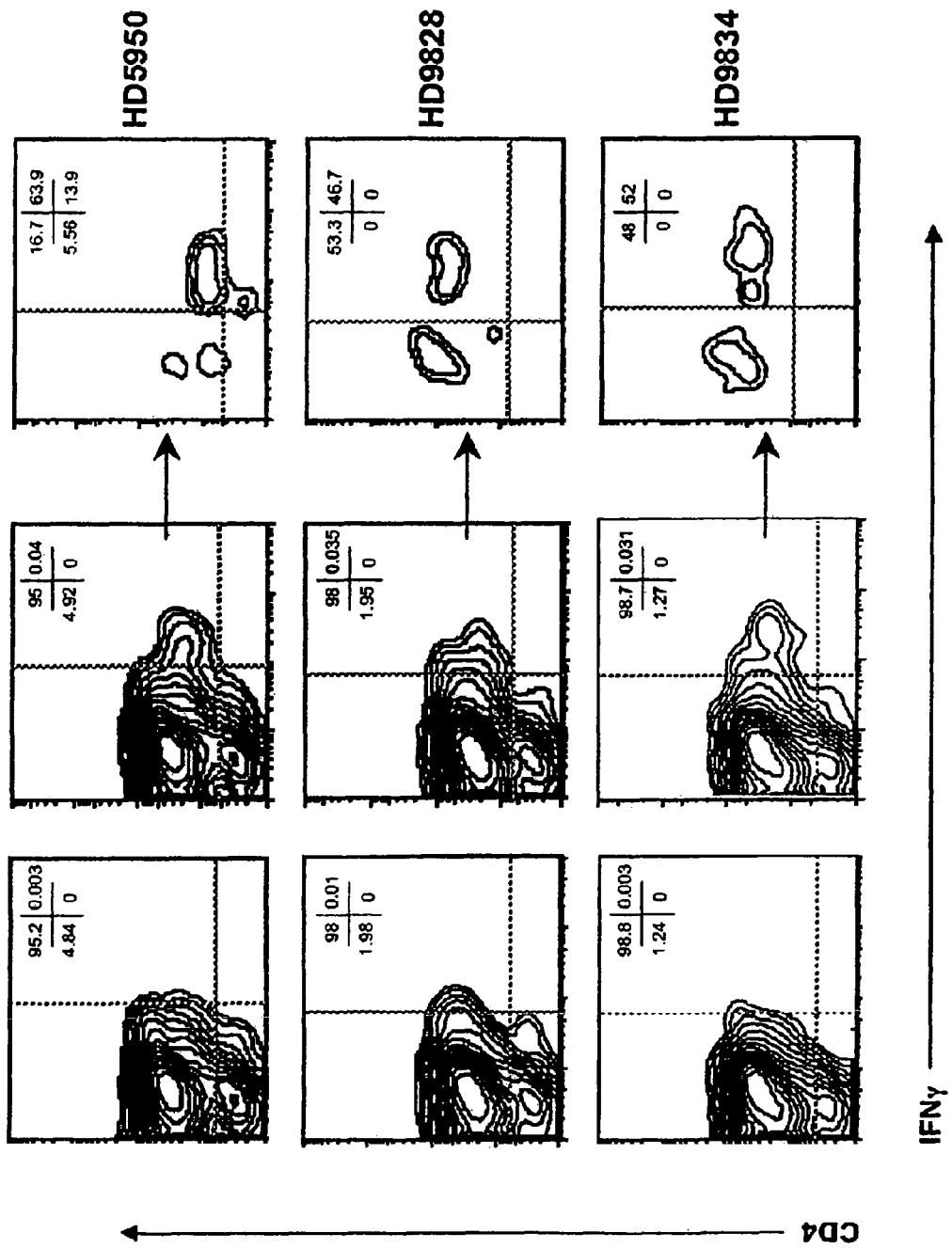

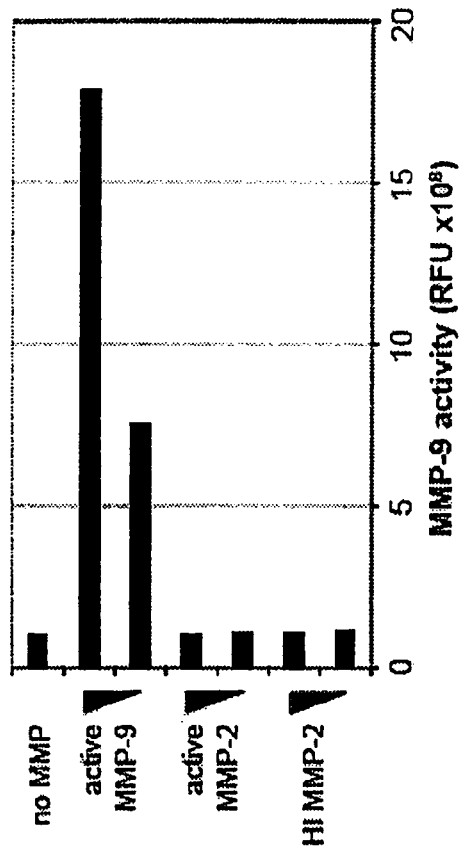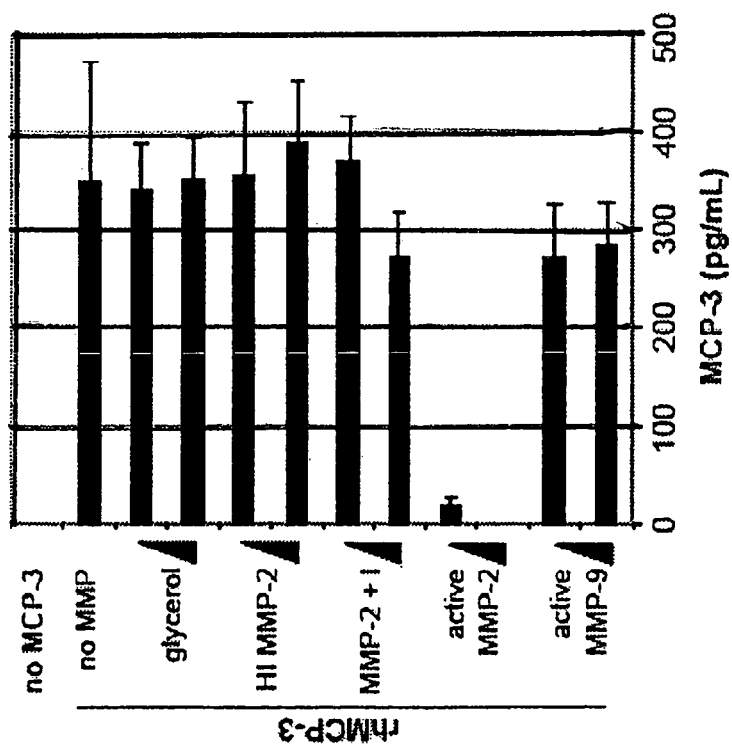
Fig. 13D
Fig. 13C

Fig. 16

| CD4⁺ T cell Clones | MMP-2 epitope positions | TCR Vβ | restricting HLA |
|---|---|---|---|
| HD5950/MC2/45 | 1-20 | 22 | DR |
| HD5950/MC3/26 | 1-20 | 2 | DR |
| HD5950/MC3/47 | 1-20 | 2 | DR |
| HD5950/MC2/5 | 11-30 | nd | DR |
| HD5950/MC2/33 | 11-30 | nd | DR |
| HD5950/MC2/8 | 21-40 | nd | DR |
| HD5950/MC2/50 | 21-40 | nd | DR |
| HD5950/MC3/16 | 21-40 | nd | DR |
| HD5950/MC3/43 | 21-40 | nd | DR |
| HD5950/MC3/30 | 41-60 | 13.2 | nd |
| HD5950/MC2/43 | 161-180 | 17 | nd |
| HD5950/MC3/4 | 161-180 | 17 | nd |
| HD9834/MC1/32 | 361-380 | nd | DR |
| HD9828/MC1/46 | 551-570 | 13.1 | nd |
| HD9828/MC1/35 | 571-590 | 13.2 | nd |
| HD9828/MC1/56 | 601-620 | nd | DR |
| HD5950/MC1/38 | 621-640 | 5.3 | DR |
| HD5950/MC1/67 | 621-640 | 13.2 | DR |
| *HD9828/MC1/52* | *631-650* | *21.3* | *DR* |

SEQUENCE LISTING

```
<160> NUMBER OF SEQ ID NOS: 27

<210> SEQ ID NO 1
<211> LENGTH: 660
<212> TYPE: PRT
<213> ORGANISM: Homo sapiens

<400> SEQUENCE: 1

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
                20                  25                  30

Pro Ile Ile Lys Phe Pro Gly Asp Val Ala Pro Lys Thr Asp Lys Glu
            35                  40                  45

Leu Ala Val Gln Tyr Leu Asn Thr Phe Tyr Gly Cys Pro Lys Glu Ser
        50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220
```

-continued

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
            245                 250                 255

Leu Trp Cys Ser Thr Thr Tyr Asn Phe Glu Lys Asp Gly Lys Tyr Gly
        260                 265                 270

Phe Cys Pro His Glu Ala Leu Phe Thr Met Gly Gly Asn Ala Glu Gly
    275                 280                 285

Gln Pro Cys Lys Phe Pro Phe Arg Phe Gln Gly Thr Ser Tyr Asp Ser
290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
                340                 345                 350

Phe Thr Phe Leu Gly Asn Lys Tyr Glu Ser Cys Thr Ser Ala Gly Arg
        355                 360                 365

Ser Asp Gly Lys Met Trp Cys Ala Thr Thr Ala Asn Tyr Asp Asp Asp
370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
            420                 425                 430

Leu Ser Gln Asp Asp Ile Lys Gly Ile Gln Glu Leu Tyr Gly Ala Ser
        435                 440                 445

Pro Asp Ile Asp Leu Gly Thr Gly Pro Thr Pro Thr Leu Gly Pro Val
    450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
        515                 520                 525

Glu Glu Lys Ala Val Phe Phe Ala Gly Asn Glu Tyr Trp Ile Tyr Ser
530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
        595                 600                 605

Ala Trp Asn Ala Ile Pro Asp Asn Leu Asp Ala Val Val Asp Leu Gln
610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp

```
                  645                 650                 655

Trp Leu Gly Cys
            660

<210> SEQ ID NO 2
<211> LENGTH: 20
<212> TYPE: PRT
<213> ORGANISM: Homo sapiens

<400> SEQUENCE: 2

Met Glu Ala Leu Met Ala Arg Gly Ala Leu Thr Gly Pro Leu Arg Ala
1               5                   10                  15

Leu Cys Leu Leu
            20

<210> SEQ ID NO 3
<211> LENGTH: 20
<212> TYPE: PRT
<213> ORGANISM: Homo sapiens

<400> SEQUENCE: 3

Thr Gly Pro Leu Arg Ala Leu Cys Leu Leu Gly Cys Leu Leu Ser His
1               5                   10                  15

Ala Ala Ala Ala
            20

<210> SEQ ID NO 4
<211> LENGTH: 20
<212> TYPE: PRT
<213> ORGANISM: Homo sapiens

<400> SEQUENCE: 4

Gly Cys Leu Leu Ser His Ala Ala Ala Ala Pro Ser Pro Ile Ile Lys
1               5                   10                  15

Phe Pro Gly Asp
            20

<210> SEQ ID NO 5
<211> LENGTH: 20
<212> TYPE: PRT
<213> ORGANISM: Homo sapiens

<400> SEQUENCE: 5

Val Ala Pro Lys Thr Asp Lys Glu Leu Ala Val Gln Tyr Leu Asn Thr
1               5                   10                  15

Phe Tyr Gly Cys
            20

<210> SEQ ID NO 6
<211> LENGTH: 20
<212> TYPE: PRT
<213> ORGANISM: Homo sapiens

<400> SEQUENCE: 6

Arg Ile His Asp Gly Glu Ala Asp Ile Met Ile Asn Phe Gly Arg Trp
1               5                   10                  15

Glu His Gly Asp
            20

<210> SEQ ID NO 7
<211> LENGTH: 20
<212> TYPE: PRT
```

```
<213> ORGANISM: Homo sapiens

<400> SEQUENCE: 7

Glu Ser Cys Thr Ser Ala Gly Arg Ser Asp Gly Lys Met Trp Cys Ala
 1               5                  10                  15

Thr Thr Ala Asn
            20

<210> SEQ ID NO 8
<211> LENGTH: 20
<212> TYPE: PRT
<213> ORGANISM: Homo sapiens

<400> SEQUENCE: 8

Gly Tyr Pro Lys Pro Leu Thr Ser Leu Gly Leu Pro Pro Asp Val Gln
 1               5                  10                  15

Arg Val Asp Ala
            20

<210> SEQ ID NO 9
<211> LENGTH: 20
<212> TYPE: PRT
<213> ORGANISM: Homo sapiens

<400> SEQUENCE: 9

Ala Phe Asn Trp Ser Lys Asn Lys Lys Thr Tyr Ile Phe Ala Gly Asp
 1               5                  10                  15

Lys Phe Trp Arg
            20

<210> SEQ ID NO 10
<211> LENGTH: 20
<212> TYPE: PRT
<213> ORGANISM: Homo sapiens

<400> SEQUENCE: 10

Gly Phe Pro Lys Leu Ile Ala Asp Ala Trp Asn Ala Ile Pro Asp Asn
 1               5                  10                  15

Leu Asp Ala Val
            20

<210> SEQ ID NO 11
<211> LENGTH: 20
<212> TYPE: PRT
<213> ORGANISM: Homo sapiens

<400> SEQUENCE: 11

Val Asp Leu Gln Gly Gly Gly His Ser Tyr Phe Phe Lys Gly Ala Tyr
 1               5                  10                  15

Tyr Leu Lys Leu
            20

<210> SEQ ID NO 12
<211> LENGTH: 20
<212> TYPE: PRT
<213> ORGANISM: Homo sapiens

<400> SEQUENCE: 12

Phe Phe Lys Gly Ala Tyr Tyr Leu Lys Leu Glu Asn Gln Ser Leu Lys
 1               5                  10                  15

Ser Val Lys Phe
            20
```

<210> SEQ ID NO 13
<211> LENGTH: 1983
<212> TYPE: DNA
<213> ORGANISM: Homo sapiens

<400> SEQUENCE: 13

| | | | | | |
|---|---|---|---|---|---|
| atggaggcgc | taatggcccg | gggcgcgctc | acgggtcccc | tgagggcgct | ctgtctcctg | 60 |
| ggctgcctgc | tgagccacgc | cgccgccgcg | ccgtcgccca | tcatcaagtt | ccccggcgat | 120 |
| gtcgccccca | aaacggacaa | agagttggca | gtgcaatacc | tgaacacctt | ctatggctgc | 180 |
| cccaaggaga | gctgcaacct | gtttgtgctg | aaggacacac | taagaagat | gcagaagttc | 240 |
| tttggactgc | cccagacagg | tgatcttgac | cagaatacca | tcgagaccat | gcggaagcca | 300 |
| cgctgcggca | acccagatgt | ggccaactac | aacttcttcc | ctcgcaagcc | caagtgggac | 360 |
| aagaaccaga | tcacatacag | gatcattggc | tacacacctg | atctggaccc | agagacagtg | 420 |
| gatgatgcct | ttgctcgtgc | cttccaagtc | tggagcgatg | tgaccccact | gcggttttct | 480 |
| cgaatccatg | atggagaggc | agacatcatg | atcaactttg | ccgctgggcga | gcatggcgat | 540 |
| ggatacccct | tgacggtaa | gacggactc | ctggctcatg | ccttcgcccc | aggcactggt | 600 |
| gttggggggag | actcccattt | tgatgacgat | gagctatgga | ccttgggaga | aggccaagtg | 660 |
| gtccgtgtga | agtatggcaa | cgccgatggg | gagtactgca | agttccccctt | cttgttcaat | 720 |
| ggcaaggagt | acaacagctg | cactgatact | ggccgcagcg | atggcttcct | ctggtgctcc | 780 |
| accacctaca | actttgagaa | ggatggcaag | tacggcttct | gtccccatga | agccctgttc | 840 |
| accatgggcg | gcaacgctga | aggacagccc | tgcaagtttc | cattccgctt | ccagggcaca | 900 |
| tcctatgaca | gctgcaccac | tgagggccgc | acggatggct | accgctggtg | cggcaccact | 960 |
| gaggactacg | accgcgacaa | gaagtatggc | ttctgccctg | agaccgccat | gtccactgtt | 1020 |
| ggtgggaact | cagaaggtgc | ccctgtgtc | ttccccttca | ctttcctggg | caacaaatat | 1080 |
| gagagctgca | ccagcgccgg | ccgcagtgac | ggaaagatgt | ggtgtgcgac | cacagccaac | 1140 |
| tacgatgacg | accgcaagtg | gggcttctgc | cctgaccaag | ggtacagcct | gttcctcgtg | 1200 |
| gcagcccacg | agtttggcca | cgccatgggg | ctggagcact | cccaagaccc | tggggccctg | 1260 |
| atggcaccca | tttacaccta | caccaagaac | ttccgtctgt | cccaggatga | catcaagggc | 1320 |
| attcaggagc | tctatggggc | ctctcctgac | attgaccttg | gcaccggccc | cacccccaca | 1380 |
| ctgggccctg | tcactcctga | gatctgcaaa | caggacattg | tatttgatgg | catcgctcag | 1440 |
| atccgtggtg | agatcttctt | cttcaaggac | cggttcattt | ggcggactgt | gacgccacgt | 1500 |
| gacaagccca | tgggggcccct | gctggtggcc | acattctggc | ctgagctccc | ggaaaagatt | 1560 |
| gatgcggtat | acgaggcccc | acaggaggag | aaggctgtgt | tctttgcagg | aatgaatac | 1620 |
| tggatctact | cagccagcac | cctggagcga | gggtaccca | agccactgac | cagcctggga | 1680 |
| ctgcccctg | atgtccagcg | agtggatgcc | gcctttaact | ggagcaaaaa | caagaagaca | 1740 |
| tacatctttg | ctggagacaa | attctggaga | tacaatgagg | tgaagaagaa | aatggatcct | 1800 |
| ggctttccca | agctcatcgc | agatgcctgg | aatgccatcc | ccgataacct | ggatgccgtc | 1860 |
| gtggacctgc | agggcggcgg | tcacagctac | ttcttcaagg | gtgcctatta | cctgaagctg | 1920 |
| gagaaccaaa | gtctgaagag | cgtgaagttt | ggaagcatca | aatccgactg | gctaggctgc | 1980 |
| tga | | | | | | 1983 |

<210> SEQ ID NO 14

```
<211> LENGTH: 60
<212> TYPE: DNA
<213> ORGANISM: Homo sapiens

<400> SEQUENCE: 14
atggaggcgc taatggcccg gggcgcgctc acgggtcccc tgagggcgct ctgtctcctg      60

<210> SEQ ID NO 15
<211> LENGTH: 60
<212> TYPE: DNA
<213> ORGANISM: Homo sapiens

<400> SEQUENCE: 15
acgggtcccc tgagggcgct ctgtctcctg ggctgcctgc tgagccacgc cgccgccgcg      60

<210> SEQ ID NO 16
<211> LENGTH: 60
<212> TYPE: DNA
<213> ORGANISM: Homo sapiens

<400> SEQUENCE: 16
ggctgcctgc tgagccacgc cgccgccgcg ccgtcgccca tcatcaagtt ccccggcgat      60

<210> SEQ ID NO 17
<211> LENGTH: 60
<212> TYPE: DNA
<213> ORGANISM: Homo sapiens

<400> SEQUENCE: 17
gtcgccccca aaacggacaa agagttggca gtgcaatacc tgaacacctt ctatggctgc      60

<210> SEQ ID NO 18
<211> LENGTH: 60
<212> TYPE: DNA
<213> ORGANISM: Homo sapiens

<400> SEQUENCE: 18
cgaatccatg atggagaggc agacatcatg atcaactttg ccgctgggga gcatggcgat      60

<210> SEQ ID NO 19
<211> LENGTH: 60
<212> TYPE: DNA
<213> ORGANISM: Homo sapiens

<400> SEQUENCE: 19
gagagctgca ccagcgccgg ccgcagtgac ggaaagatgt ggtgtgcgac cacagccaac      60

<210> SEQ ID NO 20
<211> LENGTH: 60
<212> TYPE: DNA
<213> ORGANISM: Homo sapiens

<400> SEQUENCE: 20
gggtacccca agccactgac cagcctggga ctgccccctg atgtccagcg agtggatgcc      60

<210> SEQ ID NO 21
<211> LENGTH: 60
<212> TYPE: DNA
<213> ORGANISM: Homo sapiens

<400> SEQUENCE: 21
gcctttaact ggagcaaaaa caagaagaca tacatctttg ctggagacaa attctggaga      60
```

```
<210> SEQ ID NO 22
<211> LENGTH: 60
<212> TYPE: DNA
<213> ORGANISM: Homo sapiens

<400> SEQUENCE: 22
ggctttccca agctcatcgc agatgcctgg aatgccatcc ccgataacct ggatgccgtc    60

<210> SEQ ID NO 23
<211> LENGTH: 60
<212> TYPE: DNA
<213> ORGANISM: Homo sapiens

<400> SEQUENCE: 23
gtggacctgc agggcggcgg tcacagctac ttcttcaagg gtgcctatta cctgaagctg    60

<210> SEQ ID NO 24
<211> LENGTH: 60
<212> TYPE: DNA
<213> ORGANISM: Homo sapiens

<400> SEQUENCE: 24
ttcttcaagg gtgcctatta cctgaagctg gagaaccaaa gtctgaagag cgtgaagttt    60

<210> SEQ ID NO 25
<211> LENGTH: 10
<212> TYPE: PRT
<213> ORGANISM: Homo sapiens

<400> SEQUENCE: 25

Gly Leu Pro Pro Asp Val Gln Arg Val Asp
 1               5                  10

<210> SEQ ID NO 26
<211> LENGTH: 9
<212> TYPE: PRT
<213> ORGANISM: Homo sapiens

<400> SEQUENCE: 26

Ile Phe Ala Gly Asp Lys Phe Trp Arg
 1               5

<210> SEQ ID NO 27
<211> LENGTH: 9
<212> TYPE: PRT
<213> ORGANISM: Human Immunodeficiency Virus

<400> SEQUENCE: 27

Arg Lys Lys Arg Arg Gln Arg Arg Arg
 1               5
```

METHODS, AGENTS AND PEPTIDES FOR INDUCING AN IMMUNE RESPONSE TO MATRIX METALLOPROTEINASE-2 EXPRESSING TUMORS

CROSS REFERENCE TO RELATED APPLICATIONS

The present application is a Divisional Application of U.S. application Ser. No. 12/930,592, filed Jan 11, 2011, which in turn claims priority under 35 USC §119(e) from U.S. Provisional Application Ser. No. 61/335,765, filed Jan 12, 2010, each of which applications is herein specifically incorporated by reference in its entirety.

GOVERNMENTAL SUPPORT

The research leading to the present invention was supported, at least in part, by National Institutes of Health Grant Nos. R01 AI071078 and CCSG 5 P30 CA16087. Accordingly, the Government has certain rights in the invention.

FIELD OF THE INVENTION

The present invention relates to enhancing, modulating and/or stimulating the immune response to matrix metalloproteinase-2 (MMP-2) and tumors expressing MMP-2 and to the modulation and application of MMP-2 peptides for pharmaceutical and immunogenic compositions, as well as vaccines. Melanoma is an exemplary tumor type that expresses MMP-2 and for which such pharmaceutical and immunogenic compositions, as well as vaccines, would confer benefit to patients. The invention relates to methods and means to activate an immune response to MMP-2 and tumors expressing MMP-2, as well as modulating the predominantly $T_H2$ driven anti-tumor immune responses induced by MMP-2 to achieve a more effective $T_H1$ driven response.

BACKGROUND OF THE INVENTION

The citation of references herein shall not be construed as an admission that such is prior art to the present invention.

A large array of human melanoma-associated antigens (MAA) has been identified and used in various immunization strategies to treat cancer patients. However, despite significant induction of tumor-specific T cells (Coulie and van der Bruggen, 2003; Rosenberg, 2004), the therapeutic efficacy of these approaches has been suboptimal, indicating a need for improving current strategies. Possible explanations for failure (Loose and Van de Wiele, 2009) include malignant cells producing immunosuppressive cytokines (IL-10, TGFβ, IL-6 and M-CSF), prostaglandins and vascular endothelial growth factor, thereby skewing the immune response towards type-2 or regulatory T cells and deleteriously modulating the differentiation, maturation and function of antigen presenting cells (APCs). Furthermore, malignant cells that chronically stimulate infiltrating T cells can actively exhaust and eliminate T cells through expression of molecules such as FasL, PDL-1 or RCAS1 Finally, due to immune pressure, immunoresistant tumor cell variants emerge through selection of mutants with reduced antigenicity. This can affect the expression/function of molecules implicated in antigen processing and presentation or the expression of tumor antigens themselves (Hirohashi et al., 2009; Yee et al., 2000).

A way to circumvent this latter limitation would be to vaccinate against immunogenic proteins whose expression is critical for tumor growth and/or invasiveness. The matrix metalloproteinase-2 (MMP-2), overexpressed in many tumors including melanoma, may be such an antigen. MMP-2 is a proteolytic enzyme that degrades numerous components of extracellular matrix such as collagens, laminin or fibronectin and contributes to cell migration by clearing the surrounding extracellular matrix and basement membrane barriers. MMP-2 over-expression has been associated with tumor progression. Indeed, MMP-2 modulates various oncogenic processes such as angiogenesis (Brooks et al., 1998; Itoh et al., 1998) and tumor dissemination (Kessenbrock et al., 2010; Liotta et al., 1980; Westermarck and Kahari, 1999).

We previously identified MMP-2 as a novel melanoma-associated antigen (MAA) recognized by HLA-A*0201-restricted CD8$^+$ tumor infiltrating lymphocytes (TILs) (Godefroy et al., 2005). Because MMP-2 activity is critical for melanoma progression, MMP-2 is a promising tumor antigen to target in immunotherapy against malignant melanoma. Accordingly, several patients administered CD8$^+$ T cells that recognize this epitope among others have remained tumor-free up to 15 years after treatment (Godefroy et al., 2005; Khammari et al., 2007).

SUMMARY OF THE INVENTION

The invention relates generally to methods and agents for inducing an effective immune response to melanoma and other tumors that express MMP-2. Several melanoma-associated antigens have been targeted in immunization strategies to treat melanoma patients. The therapeutic efficacy of these approaches remains limited, however, indicating an urgent need for improved strategies. Because MMP-2 activity is critical for progression of many tumors, including that of melanoma, it represents an interesting target for vaccine therapy. As shown herein, MMP-2 is an immunogenic tumor antigen. MMP-2-specific CD4$^+$ T lymphocytes, however, display a suboptimal inflammatory $T_H2$ profile. Indeed, we show herein that MMP-2-conditioned DCs prime $T_H2$ responses against several melanoma-associated antigens (MAA), suggesting that MMP-2 can create a $T_H2$ skewing microenvironment in a bystander fashion. Elucidation of the underlying mechanisms opens the way to improving immune responses towards a more effective $T_H1$ response, and highlights the potential of MMP2 as a target antigen in melanoma.

Accordingly, the present invention presents novel targets for therapeutic intervention in the care of a subject afflicted with an MMP-2 expressing tumor, such as a melanoma, and novel indicators of the status of an immune response to an MMP-2 expressing tumor, such as a melanoma. Also presented are novel indicators for prognostic assessment of a subject afflicted with an MMP-2 expressing tumor, such as a melanoma. Methods for stimulating or facilitating immune response to an MMP-2 expressing tumor, and assays for screening and identifying agents, compounds or peptides to modulate immune response to an MMP-2 expressing tumor are also described herein. The method of the invention leads to methods for promoting $T_H1$ anti-tumor responses to MMP-2 expressing tumors and, more particularly, to promoting MMP-2 and/or other tumor-specific $T_H1$ responses to MMP-2 expressing tumors. The assays of the invention are based on promoting and assessing $T_H1$ responses to MMP-2 expressing tumors and, more specifically, to promoting MMP-2 specific $T_H1$ responses to MMP-2 expressing tumors. The methods, agents and assays of the invention can be implemented in pharmaceutical and immunogenic compositions, in vaccine strategies, and the stimulation of immune response to MMP-2 expressing tumors, including melanoma.

In an embodiment of the invention, an MMP-2 peptide is presented, wherein the MMP-2 peptide consists of 20-25 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; or is at least 90% identical to any one of the MMP-2 peptides consisting of 20-25 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1, wherein the MMP-2 peptide comprises a CD4+ T cell epitope. Also encompassed, are MMP-2 peptides that at least 91%, 92%, 93%, 94%, 95%, 96%, 97%, 98%, or 99% percent identical to any one of the MMP-2 peptides consisting of 20-25 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1, wherein the MMP-2 peptide comprises a CD4+ T cell epitope.

Accordingly, an MMP-2 peptide is presented, wherein the MMP-2 peptide consists of (a) 20 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (b) 21 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (c) 22 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (d) 23 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (e) 24 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; or (f) 25 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; wherein the at least one MMP-2 peptide comprises a CD4+ T cell epitope. Also encompassed, are MMP-2 peptides that at least 90%, 91%, 92%, 93%, 94%, 95%, 96%, 97%, 98%, or 99% percent identical to any one of the MMP-2 peptides consisting of 20-25 contiguous amino acids [(a)-(f) above] of SEQ ID NO: 1 comprising any one of P1-20, P11-30, P21-40, P41-60, P161-180, P361-380, P551-570, P571-590, P601-620, P621-640, or P631-650 of SEQ ID NO: 1, wherein the MMP-2 peptide comprises a CD4+ T cell epitope.

Also encompassed herein are MMP-2 peptides, wherein the MMP-2 peptide consists of any one of P1-20, P11-30, P21-40, P41-60, P161-180, P361-380, P551-570, P571-590, P601-620, P621-640, or P631-650 of SEQ ID NO: 1, or is at least 90% identical to any one of P1-20, P11-30, P21-40, P41-60, P161-180, P361-380, P551-570, P571-590, P601-620, P621-640, or P631-650 of SEQ ID NO: 1.

A vaccine or immunogenic composition comprising a pharmaceutically acceptable carrier and at least one of the MMP-2 peptides as described herein is also envisioned. In a particular aspect, a vaccine or immunogenic composition is encompassed comprising a pharmaceutically acceptable carrier and at least one MMP-2 peptide, wherein the at least one MMP-2 peptide consists of 20-25 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1, wherein the at least one MMP-2 peptide comprises a CD4+ T cell epitope; or a protein comprising SEQ ID NO: 1, wherein the protein is enzymatically inactive.

Accordingly, a vaccine or immunogenic composition comprising a pharmaceutically acceptable carrier and at least one MMP-2 peptide, wherein the at least one MMP-2 peptide consists of (a) 20 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (b) 21 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (c) 22 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (d) 23 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; (e) 24 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; or (f) 25 contiguous amino acids of SEQ ID NO: 1 comprising any one of P1-20, P11-30, P21-40, P41-60, P161-180, P361-380, P551-570, P571-590, P601-620, P621-640, or P631-650 of SEQ ID NO: 1; wherein the at least one MMP-2 peptide comprises a CD4+ T cell epitope.

In a more particular embodiment, the vaccine or immunogenic composition further comprises a therapeutically effective amount of interleukin-12 (IL-12) or a blocking agent of OX40L, e.g. an anti-OX40L monoclonal antibody.

In another aspect of the invention, a vaccine or pharmaceutical composition comprising autologous $T_H1$ cells specific for at least one of the MMP-2 peptides described herein, and a pharmaceutically acceptable carrier is envisioned. In accordance with guidance presented herein and known in the art, autologous T cells are isolated from a patient and exposed to the at least one MMP-2 peptide in vitro to generate autologous $T_H1$ cells specific for the at least one MMP-2 peptide. In a more particular embodiment, autologous $T_H1$ cells specific for the at least one MMP-2 peptide are selected for epitope specificity, functional capacities such as cytokine secretion, proliferative capacity, differentiation status, and/or anti-tumor activity prior to administration to a subject in need thereof.

Also encompassed herein is a method for stimulating or enhancing an immune response to a matrix metalloproteinase-2 (MMP-2) expressing tumor comprising administering at least one of the MMP-2 peptides described herein or a nucleic acid sequence encoding same; a protein comprising SEQ ID NO: 1, wherein the protein is enzymatically inactive (e.g., heat inactivated; or a vaccine or immunogenic composition as described herein. As described herein, the method may be performed in vitro in a cell culture comprising the relevant cell types, such as, e.g., APCs and T cells (e.g., naive T cells or PBLs) or performed in a subject by administering the above to a subject in need thereof.

In an aspect of the method, the MMP-2 expressing tumor is a melanoma, breast cancer, colon cancer, gastric cancer, lung cancer, ovarian cancer, pancreatic cancer, prostate cancer, or squamous cell carcinoma of the head and neck.

In yet another aspect of the method, wherein the protein or peptide is associated with or covalently attached to a polycationic or cell penetrating peptide to promote cellular uptake or delivery. An exemplary polycationic or cell penetrating peptide is a Tat peptide comprising the sequence RKKRRQRRR (SEQ ID NO: 27). In particular embodiments, dendritic cells are targeted for cellular uptake or delivery. Dendritic cells may be targeted for uptake or delivery via known means, including Toll-like receptor (TLR) agonists, conjugation to ligands for receptors expressed on DCs, conjugation to receptors expressed on DCs, or use of DC targeted vaccines.

The method may further comprise assessing enhanced cell mediated and/or humoral immune responses, wherein enhanced cell mediated immune responses are detected as an increase in at least one of MMP-2-specific CD4+ $T_H1$ cells, cytokines characteristic of CD4+ $T_H1$ cells, MMP-2-specific CD8+ T cells, and dendritic cells expressing type-I IFN receptor (IFNAR1); and enhanced humoral immune responses are detected as an increase in at least one of MMP-2 specific B cells and MMP-2 specific antibodies.

In particular aspects, the method inhibits induction of MMP-2-specific CD4+ $T_H2$ cells.

In particular embodiments, the method calls for using nucleic acid sequences encoding at least one of the MMP-2 peptides, wherein the nucleic acid sequences are at least one of SEQ ID NOs: 14-24.

In certain aspects, the method involves administering the MMP-2 peptides or nucleic acid sequences encoding same, or compositions described herein to a mammalian subject. In particular embodiments, the mammalian subject has an MMP-2 expressing tumor. The MMP-2 expressing tumor may, for example, be a melanoma. In a more particular embodiment, the mammalian subject is a human.

Also encompassed herein is a method for monitoring and assessing immune response to an MMP-2 expressing tumor comprising assessing enhanced cell mediated and/or humoral immune responses, wherein enhanced cell mediated immune responses are detected as an increase in at least one of MMP-2-specific CD4+ $T_H1$ cells, cytokines characteristic of CD4+ $T_H1$ cells, MMP-2-specific CD8+ T cells, and dendritic cells expressing type-I IFN receptor (IFNAR1); and enhanced humoral immune responses are detected as an increase in at least one of MMP-2 specific B cells and MMP-2 specific antibodies.

Also envisioned is a method of screening for an agent, compound or peptide capable of stimulating or enhancing an immune response to an MMP-2 expressing tumor comprising determining the expression or activity of an MMP-2-specific CD4+ $T_H1$ cell immune response marker in a cellular system in the presence of an MMP-2 peptide, wherein the expression or activity of the MMP-2-specific CD4+$T_H1$ cell immune response marker is increased or enhanced in the presence of the agent, compound or peptide.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 3A-D shows MMP-2-specific CD4+ T cells display an inflammatory $T_H2$ phenotype. (A, B) CD4+ T cell clones were stimulated with peptides (2 μM) for 6 h. Cytokine production was assessed by intracellular staining (clone HD5950/MC2/43 is shown as an example) (A). The results for the 19 MMP-2-specific CD4+ clones are also shown (B, black bars). Three Melan-A/MART-1- and 8 NY-ESO-1-specific CD4+ T cell clones were stimulated with peptides (2 μM) for 6 h before intracellular staining for cytokines (B, gray and white bars, respectively). (C, D) T-bet and GATA-3 expression was measured by intracellular staining of MMP-2-(n=19), Melan-A/MART-1-(n=3) and NY-ESO-1-specific CD4+ T cell clones (n=8). Histogram plots show a representative example for one NY-ESO-1-specific CD4+ T cell clone (HD3014/1) and one MMP-2-specific CD4+ T cell clone (HD5950/33). (C) Isotype control is represented in tinted gray. (D) MFIs for all CD4+ T cell clones are represented. Cord blood-derived CD4+/CD45RA+/CD62L+ naive cells (n=9) were used as a negative control. For each cytokine or transcription factor, analyses of variance were used to compare T cells specific for MMP-2, Melan-A and NY-ESO-1, and t-tests were used for pairwise comparisons between groups. P values≤0.025 (*) were considered statistically significant using a Bonferroni correction for 2 comparisons. See also FIG. 11 and FIG. 16: Table 1.

FIG. 4A-B shows an effect of MMP-2 enzyme on specific CD4+ T cell differentiation. Cord blood-derived CD4+/CD25− cells from 11 donors were stimulated with irradiated autologous CD4− cells loaded either with active MMP-2, heat-inactivated (HI) MMP-2 or with MMP-2 pre-incubated with a specific inhibitor (+I). After 15 days, CD4+ T cells were stimulated with the MMP-2 peptide pool (2 μM) for 6 h before intracellular staining of cytokines. (A) Density plots representing cytokine production by CD4+ T cells are shown for the representative donor CB35 primed to MMP-2 either in its active form or after heat-inactivation. Numbers indicate percentages of cytokine-producing cells upon MMP-2 peptide stimulation. (B) Cytokines secreted by MMP-2-specific CD4+ T cells primed to inactive protein or peptides for all donors are shown and compared to MMP-2-specific CD4+ T cells generated after priming with active MMP-2. MMP-2 enzymatic activity was controlled (FIG. 13C-D). For each cytokine, 3 paired t-tests were used to compare active MMP-2 to heat inactivated MMP-2, to MMP-2+I, and to MMP-2 peptides. P values≤0.0167 (*) were considered statistically significant using a Bonferroni correction for 3 comparisons.

FIG. 5A-B shows MMP-2 influences Melan-A/MART-1- and NY-ESO-1-specific T helper differentiation. (A) Cord blood-derived CD4+/CD25− cells were stimulated with autologous poly(I:C)-matured DCs pulsed with overlapping peptides spanning either Melan-A/MART-1 or NY-ESO-1. Prior to poly(I:C) addition, DCs were incubated with or without MMP-2 (active or heat-inactivated) for 1 h. MMP-2 enzymatic activity was controlled (FIG. 13C-D). After 15 days, CD4+ T cells were stimulated with the Melan-A/MART-1 or NY-ESO-1 peptide pools (2 μM) for 6 h before intracellular staining of cytokines. Percentages of antigen-specific CD4+ T cells, secreting indicated cytokines, are represented for all donors. (B) Contour plots showing percentages of cytokine-producing CD4+ T cells are shown for representative donor CB45 primed to Melan-A/MART-1. Percentage of secreting cells upon peptide stimulation was considered specific/positive when it exceeded by more than twofold the background (cytokine-secreting cells in the absence of stimulation) and had more than 0.5% of responding cells (after background subtraction) for at least one cytokine. For each cytokine, 2 paired t-tests were used to compare priming in the presence of active MMP-2 to either priming in the absence of active MMP-2 or with HI MMP-2. The Bonferroni adjustment was used for multiple comparisons. P values≤0.025 (*) were considered statistically significant using a Bonferroni correction for 2 comparisons.

FIG. 7A-H shows an MMP-2-dependent mechanism blocking IL-12 production by DCs. Immature DCs were incubated with MMP-2 (0.5 μg/mL or 5 μg/mL) and poly(I:C)-matured 1 h later. IL-12 levels were measured 16 h later. (A) Results are represented as a percentage of IL-12p70 levels, measured by CBA, produced when DCs were incubated with poly(I:C) only (n=11). (B) For intracellular staining of IL-12p35 and IL-12p40 chains, Brefeldin A was added 4 h after poly(I:C) activation and cells were stained after an additional 12 h incubation. Numbers in the upper right quadrants are the percentages of each population for a representative donor (n=3). (C,D) Immature DCs were incubated with MMP-2 for 1 h (5 μg/mL) before poly(I:C) maturation. Intracellular staining of phosphorylated (Y701) STAT1 (P-STAT1) was performed 3 h later. A representative donor (C) and results for all 3 donors (D) are shown. Active MMP-2 only significantly inhibits STAT1 phosphorylation (p≤0.0047). (E) Immature DCs were incubated with MMP-2 and poly(I:C)-matured 1 h later. IFNβ levels were measured by ELISA 16 h later. Results are represented as a percentage of IFNβ levels produced when DCs were incubated with poly(I:C) only (n=9). (F,G) 10⁶DCs/lane were treated with 0.1 μg MMP-2 or controls. Poly(I:C) was added 1 h later. IFNAR1 protein expression was detected the next day by Western blot analysis using a rabbit monoclonal antibody. A representative donor (F) and results for all 7 donors (G) are shown. (H) The rhIFNAR1 (5 μg; ≈110 kD) was incubated overnight with 0.3 μg MMP-2 before performing Western blot analysis for IFNAR1. The second band (around 90 kD) and the third band (25 kD) very likely correspond to either a degraded form of the protein still recognized by the antibody or a contaminant present in the commercial protein preparation and non-specifically recognized by the antibody. MMP-2 enzymatic activity was controlled (FIG. 13C-D). Stastistical analysis: A: Two paired t-tests were used to compare low levels of glycerol with low levels of active MMP-2 and high levels of glycerol with high levels of active MMP2; E: For low and high levels, 3 comparisons were carried out (glycerol to active MMP-2, glycerol to HI MMP-2 and active MMP-2 to active MMP-9); G: 3 comparisons were carried out (glycerol to active MMP-2, glycerol to HI MMP-2 and active MMP-2 to HI MMP-2). For the 2 comparisons, p-values≤0.025 (*) were considered statistically significant; for the 3 comparison analyses, p-values≤0.0167 (*) were considered statistically significant. See also FIGS. 13, 14 and 15.

FIG. 10A-B shows detection and enrichment of IFNγ-secreting MMP-2-specific CD4+ T cells (related to FIG. 2). (A) CD4+/CD25− T lymphocytes were stimulated with the MMP-2 peptide pool (2 μM) for 12 days after which they were re-stimulated with the MMP-2 peptide pool (204) for 6 h before intracellular staining of IFNγ. Contour plots representing percentages of cytokine-producing CD4+ T cells are shown for the 3 donors used to generate CD4+ T cell clones. (B) IFNγ-secreting MMP-2-specific T cells were enriched by cytokine-guided magnetic selection (Miltenyi). Percentages of IFNγ-producing cells purified are shown in the upper right quadrants. MMP-2-specific CD4+ T cell clones were generated from the enriched IFNγ-secreting populations by limiting dilution.

FIG. 13A-D shows that active MMP-2 does not degrade IL-12 (related to FIG. 7). (A) Recombinant IL-12p70 (at 2 doses: 3,000 and 30,000 pg/mL) was incubated in IMDM media using U-bottom 96-well plates (same conditions as cell culture) with or without MMP-2 (active or heat inactivated) at 37° C. Sixteen hours later, supernatants were harvested and their content in IL-12p70 was measured by CBA. (B) specificity of the CBA kit for intact IL-12p70 was checked using both single chains (IL-12p35 and IL-12p40) and IL-12p70 incubated overnight in indicated conditions including digested by 0.5× trypsin. After 16 h, supernatants were harvested and IL-12p70 content was measured by CBA. (C) MMP-2 activity was controlled by measuring MCP-3 degradation. Indicated forms of MMP-2 (0.5 or 5 μg/mL) were incubated overnight at 37° C. with its substrate, rhMCP-3 (300 pg/mL). MCP-3 contents were measured by ELISA. (D) MMP-9 activity was controlled using the SensoLyte MMP-9 Assay Kit (AnaSpec).

FIG. 16 shows Table 1 (related to FIG. 3). All 19 MMP-2-specific CD4+ T cell clones were characterized for epitope specificity by testing clone responses to every peptide separately. TCR Vβ expression was assessed by surface staining HLA class-II isotype restriction was determined by using blocking mAb to HLA-DP, -DQ and -DR. Results listed for the T cell clone HD9828/MC1/52 are shown in FIG. 1 and FIG. 11, and are highlighted in bold italics.

DETAILED DESCRIPTION

Figure 9A:
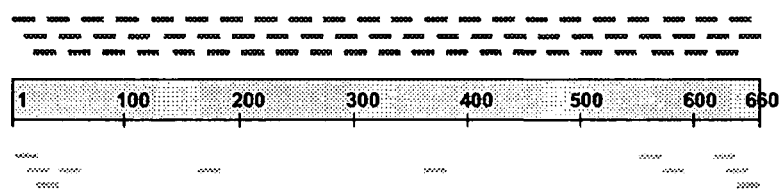
FIG. 9A-B shows MMP-2 peptides/epitopes and clinical outcome of melanoma patients with TILs containing MMP-2-specific CD4+ T cells (related to FIG. 1). (A) MMP-2 protein (660 amino acid-long) is represented in gray. Overlapping peptides spanning the entire MMP-2 amino acid sequence and used in the present study are represented in black. MMP-2 epitopes recognized by CD4+ T cell clones are shown in light gray. (B) Survival of melanoma patients with or without MMP-2-specific CD4+ T cell responses in their TILs, logrank p=0.121 (Kaplan-Meier).

Since CD4 help is essential for generating effective anti-tumor immunity, the present inventors evaluated whether MMP-2 was recognized by CD4+ T cells. Using a library of overlapping peptides covering the entire sequence of MMP-2 (SEQ ID NO: 1; see below), we detected frequent MMP-2-specific CD4+ T cell responses in melanoma patients and identified 11 novel MMP-2-derived peptides recognized by CD4+ T cell clones. See FIG. 9A for a schematic which depicts the library of overlapping peptides and the relative positions of the 11 novel MMP-2-derived peptides shown herein to be recognized by CD4+ T cell clones.

The MMP-2 protein sequence (from amino to carboxy termini) is as follows:

```
                                                    (SEQ ID NO: 1)
MEALMARGALTGPLRALCLLGCLLSHAAAAPSPIIKFPGDVAPKTDKELA

VQYLNTFYGCPKESCNLFVLKDTLKKMQKFFGLPQTGDLDQNTIETMRKP

RCGNPDVANYNFFPRKPKWDKNQITYRIIGYTPDLDPETVDDAFARAFQV

WSDVTPLRFSRIHDGEADIMINFGRWEHGDGYPFDGKDGLLAHAFAPGTG

VGGDSHFDDDELWTLGEGQVVRVKYGNADGEYCKFPFLFNGKEYNSCTDT

GRSDGFLWCSTTYNFEKDGKYGFCPHEALFTMGGNAEGQPCKFPFRFQGT

SYDSCTTEGRTDGYRWCGTTEDYDRDKKYGFCPETAMSTVGGNSEGAPCV

FPFTFLGNKYESCTSAGRSDGKMWCATTANYDDDRKWGFCPDQGYSLFLV

AAHEFGHAMGLEHSQDPGALMAPIYTYTKNFRLSQDDIKGIQELYGASPD

IDLGTGPTPTLGPVTPEICKQDIVFDGIAQIRGEIFFFKDRFIWRTVTPR

DKPMGPLLVATFWPELPEKIDAVYEAPQEEKAVFFAGNEYWIYSASTLER

GYPKPLTSLGLPPDVQRVDAAFNWSKNKKTYIFAGDKFWRYNEVKKKMDP

GFPKLIADAWNAIPDNLDAVVDLQGGGHSYFFKGAYYLKLENQSLKSVKF

GSIKSDWLGC
```

The MMP-2 nucleic acid sequence is as follows:

```
atggaggcgctaatggcccggggcgcgctcacgggtcccctgagggcgctctgtctcctgggctgcctgctgagccacgc  (SEQ ID NO: 13)

cgccgccgcgccgtcgcccatcatcaagttccccggcgatgtcgcccccaaaacggacaaagagttggcagtgcaatacc
```

-continued

```
tgaacaccttctatggctgccccaaggagagctgcaacctgtttgtgctgaaggacacactaaagaagatgcagaagttc tttggactgccccagacaggtgatcttgaccagaataccatcgagaccatgcggaagccacgctgcggcaacccagatgt ggccaactacaacttcttccctcgcaagcccaagtgggacaagaaccagatcacatacaggatcattggctacacacctg atctggacccagagacagtggatgatgcctttgctcgtgccttccaagtctggagcgatgtgaccccactgcggttttct cgaatccatgatggagaggcagacatcatgatcaactttggccgctgggagcatggcgatggataccccttttgacggtaa ggacggactcctggctcatgccttcgcccaggcactggtgttggggagactcccattttgatgacgatgagctatgga ccttgggagaaggccaagtggtccgtgtgaagtatggcaacgccgatgggagtactgcaagttccccttcttgttcaat ggcaaggagtacaacagctgcactgatactggccgcagcgatggcttcctctggtgctccaccacctacaactttgagaa ggatggcaagtacggcttctgtccccatgaagccctgttcaccatgggcggcaacgctgaaggacagccctgcaagtttc cattccgcttccagggcacatcctatgacagctgcaccactgagggccgcacggatggctaccgctggtgcggcaccact gaggactacgaccgcgacaagaagtatggcttctgccctgagaccgccatgtccactgttggtgggaactcagaaggtgc cccctgtgtcttccccttcactttcctgggcaacaaatatgagagctgcaccagcgccggccgcagtgacggaaagatgt ggtgtgcgaccacagccaactacgatgacgaccgcaagtggggcttctgccctgaccaagggtacagcctgttcctcgtg gcagcccacgagtttggccacgccatggggctggagcactcccaagaccctggggccctgatggcacccatttacaccta caccaagaacttccgtctgtcccaggatgacatcaagggcattcaggagctctatggggcctctcctgacattgaccttg gcaccggccccaccccacactgggccctgtcactcctgagatctgcaaacaggacattgtatttgatggcatcgctcag atccgtggtgagatcttcttcttcaaggaccggttcatttggcggactgtgacgccacgtgacaagcccatgggccct gctggtggccacattctggcctgagctcccggaaaagattgatgcggtatacgaggccccacaggagagaaggctgtgt tctttgcagggaatgaatactggatctactcagccagcacctggagcgagggtaccccaagccactgaccagcctggga ctgcccctgatgtccagcgagtggatgccgcctttaactggagcaaaaacaagaagacatacatctttgctggagacaa attctggagatacaatgaggtgaagaagaaaatggatcctggctttcccaagctcatcgcagatgcctggaatgccatcc ccgataacctggatgccgtcgtggacctgcagggcggcggtcacagctacttcttcaagggtgcctattacctgaagctg gagaaccaaagtctgaagagcgtgaagtttggaagcatcaaatccgactggctaggctgctga
```

As described herein, the present inventors used a pool of sixty-six 20-amino acid long, partially overlapping peptides spanning the entire sequence of MMP-2 (SEQ ID NO: 1) to screen for the presence of MMP-2-specific CD4⁺ T cells and identify the specific MMP-2 epitopes for which these clones were specific. See, for example, FIG. 9A. Using this method, CD4⁺ T cell clones specific for eleven distinct and novel MMP-2-derived peptides/epitopes were generated. An empirical approach to determining which, if any, of the potential MMP-2 peptides could induce MMP-2-specific CD4⁺ T cells was necessitated because of the nature and complexity of antigen processing and presentation by antigen presenting cells [APCs; e.g., monocyte-derived dendritic cells (DCs)] and the additional complexities involved in T cell recognition of presented antigen, which are influenced by, for example, the presence and/or concentration of particular cytokines that are instructive for divergent T cell differentiation pathways.

With regard to antigen presentation, proteins are engulfed by APCs and peptides are generated therefrom after cleavage and trimming of the protein by various proteases and peptidases localized in different subcellular compartments or the cytoplasm. This processing step leads to expression of the produced peptides on the APC surface via presentation on one of the highly polymorphic class-II HLA molecules. Peptide-HLA complexes can subsequently be recognized by particular T cells via T cell receptors (TCR), which exhibit exquisite antigen specificity. Because each step of the processes briefly described above involves so many known and unknown variables, epitopes that are going to be processed, presented and recognized by T cells cannot be predicted. In light of the above, a TCR epitope can only be identified experimentally via exhaustive analyses such as those described herein for MMP-2.

The relative positions within full length MMP-2 and amino acid sequences of the 11 novel MMP-2-derived peptides identified herein as specific epitopes recognized by CD4⁺ T cell clones and nucleic acid sequences encoded same are as follows:

```
P1-20:    MEALMARGALTGPLRALCLL (SEQ ID NO: 2), encoded by atg gag gcg cta atg gcc cgg ggc
          gcg ctc acg ggt ccc ctg agg gcg ctc tgt ctc ctg (SEQ ID NO: 14);

P11-30:   TGPLRALCLLGCLLSHAAAA (SEQ ID NO: 3), encoded by acg ggt ccc ctg agg gcg ctc tgt
          ctc ctg ggc tgc ctg ctg agc cac gcc gcc gcc gcg (SEQ ID NO: 15);
```

```
P21-40:      GCLLSHAAAAPSPIIKFPGD (SEQ ID NO: 4), encoded by ggc tgc ctg ctg agc cac gcc gcc
             gcc gcg ccg tcg ccc atc atc aag ttc ccc ggc gat (SEQ ID NO: 16);

P41-60:      VAPKTDKELAVQYLNTFYGC (SEQ ID NO: 5), encoded by gtc gcc ccc aaa acg gac aaa gag
             ttg gca gtg caa tac ctg aac acc ttc tat ggc tgc (SEQ ID NO: 17);

P161-180:    RIHDGEADIMINFGRWEHGD (SEQ ID NO: 6), encoded by cga atc cat gat gga gag gca gac
             atc atg atc aac ttt ggc cgc tgg gag cat ggc gat (SEQ ID NO: 18);

P361-380:    ESCTSAGRSDGKMWCATTAN (SEQ ID NO: 7), encoded by gag agc tgc acc agc gcc ggc cgc
             agt gac gga aag atg tgg tgt gcg acc aca gcc aac (SEQ ID NO: 19);

P551-570:    GYPKPLTSLGLPPDVQRVDA (SEQ ID NO: 8), encoded by ggg tac ccc aag cca ctg acc agc
             ctg gga ctg ccc cct gat gtc cag cga gtg gat gcc (SEQ ID NO: 20);

P571-590:    AFNWSKNKKTYIFAGDKFWR (SEQ ID NO: 9), encoded by gcc ttt aac tgg agc aaa aac aag
             aag aca tac atc ttt gct gga gac aaa ttc tgg aga (SEQ ID NO: 21);

P601-620:    GFPKLIADAWNAIPDNLDAV (SEQ ID NO: 10), encoded by ggc ttt ccc aag ctc atc gca
             gat gcc tgg aat gcc atc ccc gat aac ctg gat gcc gtc (SEQ ID NO: 22);

P621-640:    VDLQGGGHSYFFKGAYYLKL (SEQ ID NO: 11), encoded by gtg gac ctg cag ggc ggc ggt
             cac agc tac ttc ttc aag ggt gcc tat tac ctg aag ctg (SEQ ID NO: 23);
             and P631-650:    FFKGAYYLKLENQSLKSVKF (SEQ ID NO: 12), encoded by ttc ttc aag ggt gcc tat tac
             ctg aag ctg gag aac caa agt ctg aag agc gtg aag ttt (SEQ ID NO: 24).
```

Upon antigen stimulation, the MMP-2 specific CD4+ T cell clones identified secreted inflammatory $T_H2$ cytokines, i.e. TNFα, IL-4 and IL-13, but no or little IFNγ and IL-2. Further analyses revealed that MMP-2 drives the differentiation of $T_H2$ responses through inhibition of IL-12p70 production and OX40L expression by DCs. The present results, therefore, reveal a new role for MMP-2 in polarizing naive CD4+ T cells towards an inflammatory $T_H2$ profile, and thus potentially limiting effective antitumor T cell responses.

Accordingly, the present method is directed to promoting $T_H1$ responses to MMP-2 expressing tumors and, more particularly, to promoting MMP-2 specific $T_H1$ responses to MMP-2 expressing tumors so as to induce a more effective immune response against the MMP-2 expressing tumors. Methods described herein are further directed to modulating the MMP-2 directed $T_H2$ promoting microenvironment so as to create a microenvironment that promotes differentiation and activation of MMP-2 specific $T_H1$ cells, as reflected in the number of MMP-2 specific $T_H1$ cells induced therein.

The present inventors also show herein that MMP-2-conditioned DCs prime $T_H2$ responses against several melanoma-associated antigens (MAA), suggesting that MMP-2 can create a $T_H2$ skewing microenvironment in a bystander fashion. Accordingly, the present method is also directed to promoting $T_H1$ responses to MMP-2 expressing tumors and, more particularly, to promoting MMA specific $T_H1$ responses to these tumors so as to induce a more effective immune response against the tumors. Methods described herein are further directed to modulating the MMP-2 directed $T_H2$ promoting microenvironment so as to create a microenvironment that promotes differentiation and activation of MMA specific $T_H1$ cells, as reflected in the number of MMA specific $T_H1$ cells induced therein.

It will be appreciated that certain of the regions of overlap identified in the novel MMP-2 epitopes described herein may be of functional significance and the amino acid regions/structures of these overlapping regions and their utility as agents alone and in immunogenic and pharmaceutical compositions, as well as vaccines, are encompassed herein. The regions of overlap are illustrated below:

```
P1-20:      MEALMARGALTGPLRALCLL                     (SEQ ID NO: 2)
P11-30:             TGPLRALCLLGCLLSHAAAA             (SEQ ID NO: 3)
P21-40:                     GCLLSHAAAAPSPIIKFPGD     (SEQ ID NO: 4)

P621-640:   VDLQGGGHSYFFKGAYYLKL                     (SEQ ID NO: 11)
P631-650:           FFKGAYYLKLENQSLKSVKF             (SEQ ID NO: 12)
```

The MMP-2 peptides described herein as CD4+ T cell epitopes or antigens recognized by CD4+ T cells when presented by APCs are novel with respect to both sequence and functionality. Indeed, the MMP-2 peptides described herein differ from those previously described with respect to both amino acid sequence and functionality. MMP-2 peptides described in WO2005/0003442 and WO02/098351, for example, describe MMP-2 peptides that differ with respect to primary amino acid sequence and are recognized by CD8+ T cells. It is, therefore, understood that P551-570 (SEQ ID NO: 8) and P571-590 (SEQ ID NO: 9) are distinct from those described in WO2005/000342 and WO02/098351 both structurally and functionally. Accordingly, claims directed to either of SEQ ID NO: 8 and 9, compositions, and/or methods of using same include a proviso to exclude peptides consisting of the amino acid sequences of GLPPDVQRVD (SEQ ID NO: 25) and IFAGDKFWR (SEQ ID NO: 26) to the exclusion of additional amino acid sequence that flank these sequences in the context of full length MMP-2, as described in these references.

In accordance with the present discoveries, enzymatically inactive MMP-2 (SEQ ID NO: 1) may be used as an agent alone or in immunogenic or pharmaceutical compositions, or vaccines, and/or methods as described herein to promote $T_H1$ cell driven immune responses to MMP-2 expressing tumors, including melanoma. This appreciation is based on results presented herein that demonstrate that MMP-2 enzymatic activity is an important feature of the protein that contributes to the ability of the protein to skew the tumor microenvironment to favor $T_H2$ cell based responses. Enzymatically inactive MMP-2 may be produced by treating isolated MMP-2 using heat inactivation or contact with MMP-2 specific inhibitors as described in the Examples below or potentially by treatment with chemical inactivators or irradiation. Nucleic acid sequences encoding enzymatically inactive MMP-2 are also envisioned as useful as agents alone or in immunogenic or pharmaceutical compositions, or vaccines, and/or methods as described herein to promote $T_H1$ cell driven immune responses to MMP-2 expressing tumors, including melanoma. Such nucleic acid sequences would encode an enzymatically dead or inactive variant of MMP-2 and thus, would include mutations within the context of the nucleic acid sequence encoding MMP-2 (SEQ ID NO: 13). The catalytic domain of MMP-2 is, for example, known in the art and mutations that alter critical residues encoded thereby are envisioned for this purpose. A homozygous 1210G-A transition in exon 8 of the MMP2 gene, leads to glu-to-lys (E404K) substitution in the catalytic domain of the protein. The glutamic acid at codon 404 is believed to be essential for the peptidase activity of all metalloproteinases, as its carboxyl group catalyzes 2 proton transfers, helps stabilize the transition state, and triggers the release of the products. Additional inactivating mutations are also envisioned, such as a G-to-A transition in codon 101 of exon 2 of MMP2, which is known to result in replacement of an arginine by histidine (R101H) in the prodomain, a region highly conserved across species and other members of the MMP gene family that is involved in autoproteolytic activation of MMP2. See also Brooks et al. (Cell 92:391, 1998), the entire contents of which is incorporated herein by reference in its entirety, and references cited therein. Methods describing a DNA-based vaccine comprising chicken MMP-2 cDNA encoding enzymatically active chicken MMP-2 are, moreover, known as described by Su et al. (Cancer Res. 63:600, 2003), the entire contents of which is incorporated herein by reference in its entirety.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned in part with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" is any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF) or a toxin (e.g., ricin) or anti-mitotic or apoptotic agent or factor.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains Preferably, an antigen binding domain comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al., *Immunology, Second Ed,* 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

As used herein, the term "immunomodulator" refers to an agent which is able to modulate an immune response. An example of such modulation is an enhancement of cell activation or of antibody production.

The term "effective amount" of an immunomodulator refers to an amount of an immunomodulator sufficient to enhance a vaccine-induced immune response, be it cell-mediated, humoral or antibody-mediated. An effective amount of an immunomodulator, if injected, can be in the range of about 0.1-1,000 µg, preferably 1-900 µg, more preferably 5-500 µg, for a human subject, or in the range of about 0.01-10.0 µg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. For many antigens, this is in the range of about 5-100 µg for a human subject. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtiter plates for use in immunoassays, or will be mixed with pharmaceutically acceptable carriers or diluents when used in diagnosis or therapy.

As used herein, "pg" means picogram, "ng" means nanogram, "ug" or "µg" mean microgram, "mg" means milligram, "ul" or "µl" mean microliter, "ml" means milliliter, "l" means liter.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |

-continued

| TABLE OF CORRESPONDENCE | | |
|---|---|---|
| SYMBOL | | |
| 1-Letter | 3-Letter | AMINO ACID |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding MMP-2 or peptide sequences therein (such as any one of SEQ ID NOs: 2-12) or comprising or consisting of sequences which are degenerate thereto. DNA sequences having the nucleic acid sequence encoding the peptides of the invention are contemplated, including degenerate sequences thereof encoding the same, or a conserved or substantially similar, amino acid sequence. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCC or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |

| | | | |
|---|---|---|---|
| Aspartic Acid (Asp or D) | GAU or GAC | | |
| Glutamic Acid (Glu or E) | GAA or GAG | | |
| Cysteine (Cys or C) | UGU or UGC | | |
| Arginine (Arg or R) | CGU or CGC or CGA or CGG or AGA or AGG | | |
| Glycine (Gly or G) | GGU or GGC or GGA or GGG | | |
| Tryptophan (Trp or W) | UGG | | |
| Termination codon | UAA (ochre) or UAG (amber) or UGA (opal) | | |

It should be understood that the codons specified above are for RNA sequences. The corresponding codons for DNA have a T substituted for U.

Mutations can be made in the sequences encoding the protein or peptide sequences of the MMP-2 proteins, peptides or immune activator proteins or peptides of the invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)
Another grouping may be those amino acids with phenyl groups:
Phenylalanine, Tryptophan, Tyrosine
Another grouping may be according to molecular weight (i.e., size of R groups):

| | | | |
|---|---|---|---|
| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues, preferably at least about 80%, and most preferably at least about 90, 91, 92, 93, 94, 95, 96, 97, 98, or 99% of the amino acid residues are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense or stimulates a response that would be elicited on binding of a natural ligand to a binding site.

The term 'assay' means any process used to measure a specific property of a compound or agent. A 'screening assay' means a process used to characterize or select compounds based upon their activity from a collection of compounds.

"Preventing" or "prevention" refers to a reduction in risk of acquiring a disease or disorder.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the term "autologous" refers to organs, tissues, cells, or proteins isolated from a donor patient that are later re-introduced into the donor patient. Accordingly, the donor and recipient are the same patient in autologous transfers. The term "autologous T cells", for example, refers to T cells that have been isolated from a subject and then administered to the same patient. Typically, and in accordance with the present methods, the isolated T cells may be stimulated in cell culture prior to administration to the patient.

As used herein, "pg" means picogram, "ng" means nanogram, "ug" or "µg" mean microgram, "mg" means milligram, "ul" or "µl" mean microliter, "ml" means milliliter, "l" means liter.

B. Further Aspects of the Detailed Description

The invention relates generally to methods and agents for inducing and evaluating immune responses to tumors that express MMP-2. Prior to the discoveries detailed herein, there was no appreciation that MMP-2 and tumors expressing MMP-2 (e.g., melanoma) had the capacity to influence the cellular microenvironment so as to promote differentiation/induction of inflammatory $T_H2$ cells at the expense of more effective $T_H1$ cell-based responses. As described herein, MMP-2-specific CD4⁺ T lymphocytes display a suboptimal inflammatory $T_H2$ profile and, furthermore, MMP-2 can create a $T_H2$ skewing microenvironment in a bystander fashion whereby MMP-2-conditioned DCs prime $T_H2$ responses against several other melanoma-associated antigens (MAA). This insight into the mechanism/s whereby tumors expressing MMP-2 subvert the immune response to be a less effective weapon against tumor cell clearance has been used to advantage to design new therapeutic regimens, diagnostic and prognostic methods, and agents as described herein.

Accordingly, methods and agents for inducing an effective immune response to tumors that express MMP-2, including melanoma, are presented herein. In one aspect, a method directed to promoting $T_H1$ responses to MMP-2 expressing tumors and, more particularly, to promoting MMP-2 specific $T_H1$ responses to MMP-2 expressing tumors so as to induce a more effective immune response against the MMP-2 expressing tumors is presented. Methods described herein are further directed to modulating the MMP-2 driven $T_H2$ promoting microenvironment so as to create a microenvironment that promotes differentiation and activation of MMP-2 specific $T_H1$ cells, as reflected in an increase in the number of MMP-2 specific $T_H1$ cells induced thereby and/or increased levels of cytokines that are characteristic of $T_H1$ cells, such as IFNγ and IL-2. A decrease in the number of $T_H2$ cells and/or decreased levels of cytokines characteristic of $T_H2$ cells, such as IL-4 and IL-13, may also be used as an indicator of effective modulation of the tumor microenvironment to achieve a microenvironment that promotes differentiation and activation of MMP-2 specific $T_H1$ cells.

In that MMP-2-conditioned DCs prime $T_H2$ directed responses against several other MAAs (in addition to MMP-2), the present method is also directed to promoting MMA specific $T_H1$ responses to melanoma cells so as to induce a more effective immune response against melanomas. Methods described herein are further directed to modulating the MMP-2 driven $T_H2$ promoting microenvironment so as to create a microenvironment that promotes differentiation and activation of MMA specific $T_H1$ cells, as reflected in an increase in the number of MMA specific $T_H1$ cells induced thereby and/or increased levels of cytokines that are characteristic of $T_H1$ cells, such as IFNγ and IL-2. A decrease in the number of $T_H2$ cells, and/or decreased levels of cytokines characteristic of $T_H2$ cells, such as IL-4 and IL-13, and/or decreased levels of CD4⁺ T cells expressing GATA-3 may also be used as indicators of effective modulation of the tumor microenvironment to achieve a microenvironment that promotes differentiation and activation of $T_H1$ cells specific for MMAs in general, including MMP-2.

The present invention provides indicators to evaluate the effectiveness of an immune response to an MMP-2 expressing tumor (e.g., a melanoma), methods for stimulating or facilitating immune response to an MMP-2 expressing tumor (e.g., a melanoma), and assays for screening and identifying agents, compounds or peptides to modulate immune response to an MMP-2 expressing tumor (e.g., a melanoma). The methods, assays, and indicators described herein are based, in part, on the inhibition of IL-12p70 production that results from MMP-2 mediated degradation of the type-I IFN receptor (IFNAR1), which in turn prevents STAT1 phosphorylation, which is necessary for IL-12p35 production; and on the ability of MMP-2-conditioned DCs to up-regulate OX40L expression. The methods, agents and assays of the invention can be implemented in vaccine strategies and the stimulation of a $T_H1$ cell-based immune response to an MMP-2 expressing tumor, such as melanoma.

Thus, a purpose of the present method is to induce an effective immune response to MMP-2 expressing tumors, including melanoma. As described above, triggering an effective $T_H1$ cell-based immune response to MMP-2 expressing tumors comprises one aspect of an effective immune response. The methods, assays, and indicators described herein are also envisioned as useful in triggering an effective antibody-based response to MMP-2 and tumors expressing same. This invention thus provides a means to overcome earlier failures to develop MMP-2 based pharmaceutical and immunogenic compositions and vaccines.

The present invention demonstrates that MMP-2 is an immunogenic tumor antigen and, more particularly, that specific MMP-2 peptides identified herein are antigenic epitopes as evidenced by the presence of MMP-2-specific CD4$^+$ T lymphocytes reactive to these specific peptides in melanoma patients. See, for example, FIG. 16: Table 1. As shown herein, full length MMP-2 (SEQ ID NO: 1) is an immunogenic antigen. In a particular embodiment, variants of SEQ ID NO: 1 that are enzymatically dead by virtue of mutation/s in essential sites necessary for MMP-2 activity and/or by virtue of chemical or heat inactivation are envisioned as immunogenic antigens that possess advantageous properties as compared to full length enzymatically SEQ ID NO: 1 because the ability of MMP-2 to promote $T_H2$ immune responses at the expense of $T_H1$ immune responses is dependent on MMP-2 enzymatic activity.

MMP-2 antigenic epitopes identified herein are also envisioned as particularly effective immunogens because they have been demonstrated to elicit T cell responses and they lack MMP-2 enzymatic activity. The relative positions within full length MMP-2 and amino acid sequences of the 11 novel MMP-2-derived peptides identified herein as specific epitopes recognized by CD4$^+$ T cell clones are as follows: P1-20: MEALMARGALTGPLRALCLL (SEQ ID NO: 2); P11-30: TGPLRALCLLGCLLSHAAAA (SEQ ID NO: 3); P21-40: GCLLSHAAAAPSPIIKFPGD (SEQ ID NO: 4); P41-60: VAPKTDKELAVQYLNTFYGC (SEQ ID NO: 5); P161-180: RIHDGEADIMINFGRWEHGD (SEQ ID NO: 6); P361-380: ESCTSAGRSDGKMWCATTAN (SEQ ID NO: 7); P551-570: GYPKPLTSLGLPPDVQRVDA (SEQ ID NO: 8); P571-590: AFNWSKNKKTYIFAGDKFWR (SEQ ID NO: 9); P601-620: GFPKLIADAWNAIPDNLDAV (SEQ ID NO: 10); P621-640: VDLQGGGHSYFFKGAYYLKL (SEQ ID NO: 11); and P631-650: FFKGAYYLKLENQSLKSVKF (SEQ ID NO: 12). The peptides may be combined with, associated with, covalently attached to or fused to other immune modulators, including interferons, interleukins, T or B cell antigens or stimulators, other activators, or adjuvant molecules.

Accordingly, MMP-2 proteins and peptides are described herein which have application and use, alone or in combination with other immune system modulators, T cell modulators, antibodies, vaccines, antigens, or chemotherapeutics for stimulating, facilitating or enhancing desired immune system or immune cell actions or activities, particularly those directed against MMP-2 expressing tumors, that result in tumor regression and/or improved patient survival.

In a further embodiment, the present invention relates to certain therapeutic methods which would be based upon the activity of at least one of enzymatically inactivate SEQ ID NO: 1 or SEQ ID NOs: 2-12, or upon agents or other drugs determined to possess the same activity. A therapeutic method is associated with the modulation of the immune response, particularly stimulation or enhancement of immunity and response to MMP-2 expressing tumors, particularly to melanoma. A further therapeutic method is associated with methods for stimulating immune response to MMP-2 expressing tumors comprising administering at least one of enzymatically inactivate SEQ ID NO: 1 or SEQ ID NOs: 2-12, or agents or other drugs determined to possess the same activity, alone or in combination with other MMAs, or other immune modulators, including adjuvants, for generating an immunogenic and/or protective response to MMP-2 expressing tumors. In one aspect of this method, at least one of enzymatically inactivated SEQ ID NO: 1 or SEQ ID NOs: 2-12, or agents or other drugs determined to possess the same activity, are administered to individuals diagnosed as having an MMP-2 expressing tumor, such as melanoma, to stimulate effective immune response to these tumors and clearance of tumor cells.

MMP-2 expressing tumors are known in the art and include the following: melanoma, wherein higher levels of expression are noted in malignant tumors as compared to pre-malignant lesions, and higher levels are correlated with distant metastases and reduced survival; breast cancer, wherein higher levels of expression are noted in malignant tumors as compared to normal tissue, higher activation in malignant tumors is noted as compared to normal tissue, higher levels are correlated with tumor stage, lymph node metastases and distant metastases, and increased levels are correlated with reduced survival; colon cancer, wherein higher levels of expression are noted in malignant tumors as compared to normal tissue, higher activation in malignant tumors is noted as compared to normal tissue, and higher levels are correlated with tumor stage, angiogenesis and local invasion; gastric cancer, wherein higher levels of expression are noted in malignant tumors as compared to normal tissue, higher activation in malignant tumors is noted as compared to normal tissue, and increased levels are correlated with increased invasion and reduced survival; lung cancer, wherein higher levels of expression are noted in malignant tumors as compared to normal tissue, higher activation in malignant tumors is noted as compared to normal tissue, and higher levels are correlated with tumor stage, lymph node metastases and distant metastases; ovarian cancer, wherein higher levels of expression are noted in malignant tumors as compared to pre-malignant lesions, higher activation in malignant tumors is noted as compared to normal tissue, and higher levels are correlated with reduced survival; pancreatic cancer, wherein higher levels of expression are noted in malignant tumors as compared to normal tissue, and higher levels are correlated with lymph node metastases, distant metastases, and reduced survival;

prostate cancer, wherein higher levels of expression are noted in malignant tumors as compared to pre-malignant lesions and higher levels are correlated with tumor grade; and squamous cell carcinoma of the head and neck, wherein higher levels of expression are noted in malignant tumors as compared to normal tissue, and higher levels are correlated with lymph node metastases, distant metastases, reduced survival, and poor treatment response. See Egeblad M and Werb Z, New functions for the matrix metalloproteinases in cancer progression. Nat Rev Cancer. 2002 March; 2(3):161-74, the entire contents of which is incorporated herein by reference.

The present invention also includes enzymatically inactivate SEQ ID NO: 1 or any one of or at least one of SEQ ID NOs: 2-12, or agents or other drugs determined to possess the same activity, which are covalently attached to or otherwise associated with other molecules or agents. These other molecules or agents include, but are not limited to, molecules (including antibodies or antibody fragments) with distinct recognition, targeting or binding characteristics, immune cell modulators, immune cell antigens, toxins, ligands, adjuvants, and chemotherapeutic agents.

Peptides, proteins of the invention may be labelled with a detectable or functional label. Detectable labels include, but are not limited to, radiolabels such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{117}$Lu, $^{211}$At, $^{198}$Au, $^{67}$Cu, $^{225}$Ac, $^{213}$Bi, $^{99}$Tc and $^{186}$Re, which may be attached to antibodies of the invention using conventional chemistry known in the art of antibody imaging Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Peptides of and of use in the present invention may include synthetic, recombinant or peptidomimetic entities. The peptides may be monomers, polymers, multimers, dendrimers, concatamers of various forms known or contemplated in the art, and may be so modified or multimerized so as to improve activity, specificity or stability. For instance, and not by way of limitation, several strategies have been pursued in efforts to increase the effectiveness of antimicrobial peptides including dendrimers and altered amino acids (Tam, J. P. et al (2002) Eur J Biochem 269 (3): 923-932; Janiszewska, J. et al (2003) Bioorg Med Chem Lett 13 (21):3711-3713; Ghadiri et al. (2004) Nature 369(6478):301-304; DeGrado et al (2003) Protein Science 12(4):647-665; Tew et al. (2002) PNAS 99(8): 5110-5114; Janiszewska, J et al (2003) Bioorg Med Chem Lett 13 (21): 3711-3713). U.S. Pat. No. 5,229,490 to Tam discloses a particular polymeric construction formed by the binding of multiple antigens to a dendritic core or backbone.

Protamines or polycationic amino acid peptides containing combinations of one or more recurring units of cationic amino acids, such as arginine (R), tryptophan (W), lysine (K), even synthetic polyarginine, polytryptophan, polylysine, have been shown to be capable of killing microbial cells. These peptides cross the plasma membrane to facilitate uptake of various biopolymers or small molecules (Mitchell D J et al (2002) J Peptide Res 56(5):318-325).

Conjugates or fusion proteins of the present invention, wherein enzymatically inactivate SEQ ID NO: 1 or SEQ ID NOs: 2-12 of the present invention are conjugated or attached to other molecules or agents further include, but are not limited to binding members conjugated to a cell targeting agent or sequence, chemical ablation agent, toxin, immunomodulator, cytokine, cytotoxic agent, chemotherapeutic agent or drug.

Uptake and targeting of DCs can be achieved using a variety techniques known in the art, including coupling to antibodies targeting DC-specific surface molecules (Romani et al., 2010; the entire contents of which is incorporated herein in its entirety, including references cited therein); utilization of engineered Sindbis envelope that specifically target DC instead of VSV-G (Yang et al., 2008; the entire contents of which is incorporated herein in its entirety); site of administration; blood infusion; or ex vivo culture of DC, treatment if ex vivo cultured DC to introduce the desired construct/s, and re-injection of same into subject in need thereof.

In vitro assays are described herein which may be utilized by the skilled artisan to further or additionally screen, assess, and/or verify the activities of enzymatically inactivate SEQ ID NO: 1 or SEQ ID NOs: 2-12 of the present invention, including further assessing immune response targeted against MMP-2 expressing tumor cells. Cell based assays and in vitro methods are described herein below and were utilized to perform experiments as described, for example, in the Examples.

In vivo animal models of human MMP-2 expressing tumors and melanoma or immune response to same may be utilized by the skilled artisan to further or additionally screen, assess, and/or verify the activity of enzymatically inactivate SEQ ID NO: 1 or SEQ ID NOs: 2-12 of the present invention, including further assessing immune response targeted against MMP-2 expressing tumor cells in vivo. Such animal models include, but are not limited to models of immune system modulation or immune response.

Proteins, peptides, immune activators or agents of the present invention may be administered to a patient in need of treatment via any suitable route, including by intravenous, intraperitoneal, intramuscular injection, or orally. The precise dose will depend upon a number of factors, including whether the proteins, peptides, immune activators or agents are for diagnosis or for treatment or for prevention. The dosage or dosing regime of an adult patient may be proportionally adjusted for children and infants, and also adjusted for other administration or other formats, in proportion for example to molecular weight or immune response. Administration or treatments may be repeated at appropriate intervals, at the discretion of the physician.

Proteins, peptides, immune activators or agents of the present invention will usually be administered in the form of a pharmaceutical composition, which may comprise at least one component in addition to the proteins, peptides, immune activators or agents. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

The mode of administration of an immunogenic composition of the invention, whether of the MMP-2 peptide alone or as part of an immunogenic conjugate, may be by any suitable route which delivers an immunoprotective amount of the protein to the subject. One such route is the parenteral route, such as by intramuscular or subcutaneous administration. Other modes of administration may also be employed, where desired, such as the mucosal route, such as by oral, rectal, buccal or intranasal administration, or via other parenteral routes, i.e., intradermally, intravenously, intraperitoneally, or intratumorally.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the proteins, peptides, immune activators or agents herein described and other agents or therapeutics such as immune modulators, antibodies, immune cell stimulators, or adjuvants. In addition, the composition may be administered with hormones such as dexamethasone, immune modulators, such as interleukins, tumor necrosis factor (TNF) or other growth factors, colony stimulating factors, or cytokines which stimulate the immune response and reduction or elimination of virus. The composition may also be administered with, or may include combinations along with immune cell antigen antibodies or immune cell modulators.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A protein, peptide, immune activator or agent can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Accordingly, also encompassed herein is a composition comprising at least one of enzymatically inactivate SEQ ID NO: 1 or SEQ ID NOs: 2-12 or nucleic acid sequences encoding at least one of enzymatically inactivate SEQ ID NO: 1 or at least one of SEQ ID NOs: 2-12 and a pharmaceutically acceptable buffer, for use in treating a patient with an MMP-2 expressing tumor, such as melanoma, wherein said composition alleviates symptoms of the MMP-2 expressing tumor in the patient when administered to the patient in a therapeutically effective amount. Such compositions also have utility for use in prophylaxis for a patient at risk for developing an MMP-2 expressing tumor, including melanoma wherein said composition prevents or alleviates symptoms in the patient when administered to the patient in a therapeutically effective amount. Also encompassed herein is the use of a therapeutically effective amount of a composition comprising at least one of enzymatically inactivate SEQ ID NO: 1 or SEQ ID NOs: 2-12 or nucleic acid sequences encoding at least one of enzymatically inactivate SEQ ID NO: 1 or SEQ ID NOs: 2-12 and a pharmaceutically acceptable buffer in the manufacture of a medicament for treating a patient with an MMP-2 expressing tumor, such as melanoma, wherein the medicament alleviates or prevents symptoms of the MMP-2 expressing tumor when administered to the patient.

The peptide or agent containing compositions are conventionally administered intramuscularly, intravenously, as by injection of a unit dose, or orally, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of activation and immune response desired. Precise amounts of active ingredient required to be administered depend on the judgment of the practitioner and are peculiar to each individual. Suitable regimes for initial administration and follow on administration are also variable, and may include an initial administration followed by repeated doses at appropriate intervals by a subsequent injection or other administration.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

In accordance with the present methods, T cells may be isolated from a subject or patient via methods routinely practiced by skilled practitioners. In brief, most approaches call for isolation of a blood sample from the subject and subsequent isolation of peripheral blood lymphocytes (PBLs) therefrom. T cells of different types can then be purified via a variety of means, including fluorescence activated cell sorting (FACS) and affinity purification using cell type specific markers. Peripheral blood mononuclear cells may, for example, be collected from human donors by leukapheresis and further purified on ficoll-sodium metrizoate density gradients, after which such cells are typically washed extensively and may, as necessary, be frozen in a solution of 10% DMSO, 2% human serum albumin in phosphate buffered saline. Protocols for isolating, purifying, and re-introducing T cells to subjects are, moreover, known in the art and described in standard textbooks of clinical immunology and described in references in the literature, including Godet et al. (J Exp Med 205:2673, 2008); Vignard et al. (J Immunol 175:4797, 2005); and Khammari et al. (J Invest Derm 129:2835, 2009), the contents of each of which is specifically incorporated herein by reference.

As described herein, lymphocytes can be obtained either from a classical Ficoll of the patient's blood or from tumor fragments (tumor infiltrating lymphocytes, TILs). In the latter case, TILs can be isolated by culturing cryopreserved fragments of melanoma-invaded lymph nodes in 12-well tissue culture plates with X-vivo 15 medium containing 150 IU/ml rhIL-2 and 1 nM glutamine for 10 to 14 days. To perform high-fold expansion, $1.8 \times 10^6$ short-term culture TILs are plated at 300 viable lymphocytes/well with irradiated feeder cells into U-bottomed microplates in 200 μl rhIL-2 medium. Phytohemagglutinin is added on day 0 (15 μg/ml). After 48 h, most of the PHA is removed by replacing the culture medium. Ten days later, lymphocytes are removed from the culture plates, adjusted to $1 \times 10^6$ cells/ml in rIL-2 medium and transferred into culture trays for an additional 10 days before injection.

A brief protocol for isolating T and B cells from peripheral blood excerpted from Protocol Online (contributed by Nance E. Donacki, modified February 2009) is as follows:
Reagents
Heparin—1000 U/ml
Ficoll-Hypaque
PBS
RPMI-1640 supplemented with 10 mM glutamine and 15% FBS
AET (0.14M) Dissolve 1.967 g AET in 35 ml di-H2O.
Adjust to pH 8.0 with 1.0N NaOH. Bring volume to 50 ml with di-H2O.
Store at 2-8° C. Check pH every 2 weeks.
AET-Treated SRBC
Wash SRBC 4 times with PBS
Add 4 volumes AET to 1 volume packed SRBC in a 15 m conical tube (1 ml of AET+0.25 ml packed SRBC).
Mix well. Incubate in a 37° C. water bath for 30 minutes. Shake vigorously.
Wash 3 times with PBS.
Store in PBS at 2-8° C. for up to 3 days.
SRBC-Absorbed FBS
Mix 10 volumes of FBS with 1 volume packed SRBC.
Incubate at 37° C. for 30 minutes.
Incubate at 2-8° C. for 30 minutes.
Centrifuge at 400 g for 10 minutes.
Collect the FBS. Filter sterilize. Store aliquots at −20° C.

Preparation of PBL's
Draw peripheral blood into syringe containing 10 U/ml heparin.
Dilute the blood 1:1 with PBS.
Layer 30 ml of diluted blood onto 20 ml Ficoll-Hypaque.
Centrifuge at 1550 rpm for 30 minutes, room temperature.
Aspirate and discard the supernatant.
Carefully collect the interface of PBL's and transfer into a clean tube.
Fill the tube with PBS. Centrifuge at 1550 rpm for 10 minutes.
Wash the pellet 2 times with PBS.
Count the cells and resuspend to $10^7$ cells/ml in PBS.
Separation of T-Cells
Mix 1 ml of AET-treated SRBC with 10 ml FBS.
Mix and equal volume of PBL's with a 1% (v/v) mixture of AET-SRBC_FBS in a 50 ml tube.
Incubate in a 37° C. water bath for 10 minutes.
Centrifuge at 200 g for 10 minutes. Make sure that the cells have pelleted. If not, re-centrifuge for 5 minutes.
Place the tube upright on ice for 60 min.
Layer super over 15 ml of Ficoll-Hypaque leaving 7.5 ml of fluid above the pellet.
Resuspend the pellet by rotating the tube along the long axis.
Stand upright for 1 minute. Remove the top 5 ml and layer on Ficoll-Hypaque.
Rotate as above and transfer to gradient tube.
Wash the tube with 5 ml of PBS and add to gradient.
Centrifuge at 300 g for 40 minutes, room temperature.
Collect the B cells at the interface. Wash 3 times with PBS.
Suspend the SRBC-T cell pellet. Centrifuge at 300 d for 10 minutes.
Aspirate all of the supernatant. Break up the cell pellet by gently shaking.
Add 9 ml of di-H2O with shaking for 4 seconds.
Add 1 ml of 10×PBS with shaking.
Immediately fill the tube with 1×PBS.
Centrifuge at 300 g for 10 minutes, and wash 2 times with PBS.

It will be understood that variations in the above protocol are also envisioned and known in the art and the above protocol is presented for illustrative purposes only and is not intended to be limiting.

In accordance with the methods described herein, isolated T cells may be activated in vitro using cell culture systems as described herein or by following routine protocols understood in the art. Activated T cells (e.g., MMP-2 specific $T_H1$ cells) may then be selected based on epitope specificity, functional capacities such as cytokine secretion, proliferative capacity, differentiation status, and/or anti-tumor activity. Activated, selected T cells are then administered to a subject/patient in need thereof using techniques known in the art such as intravenous or intramuscular injection, local injection in the vicinity of an MMP-2 expressing tumor, and/or intratumoral injection.

The prognostic utility of the present invention extends to the use of markers, including the presence of CD4+ TILs specific for MMP-2, particularly MMP-2 specific $T_H2$ cells; elevated levels of cytokines characteristic of $T_H2$ cells, such as IL-4 and IL-13; elevated numbers of CD4$^+$ T cells expressing GATA-3; elevated OX40L expression on dendritic cells; and reduced levels of type-I IFN receptor (IFNAR1) on dendritic cells in assays to characterize immune response or immune system cell activation response to MMP-2 expressing tumors, including melanoma. The presence, expression, or activity of the markers may be examined by known techniques, including FACS analysis, immunoassay, RT-PCR, etc which may vary with the nature of the marker and are known to the artisan. Such analyses may be conducted in cell systems, in vitro, or in animal model systems, in vivo, or in patient or clinical or vaccine trials or evaluation studies.

Prognostic applications of the present invention, particularly protein, peptide, immune activator or agents thereof, include in vitro and in vivo applications well known and standard to the skilled artisan and based on the present description. Diagnostic assays and kits for in vitro assessment and evaluation of immune system status and/or immune response to MMP-2 expressing tumors, including melanoma, may be utilized to diagnose, evaluate and monitor patient samples and patients with regard to an anticipated or desired immune system response, antigen response, or vaccine response. The assessment and evaluation of immune system status and/or immune response is also useful in determining the suitability of a patient for a clinical trial of a drug or for the administration of a particular chemotherapeutic agent, including a protein, peptide, immune activator or agent of the present invention, including combinations thereof, versus a different agent.

In accordance with the above, an assay system for screening potential drugs effective to modulate CD4+ T cell immune response to MMP-2 expressing tumors, particularly to melanoma, may be prepared. The MMP-2 peptides (e.g., at least one of SEQ ID NOs: 2-12), for example, may be introduced into a test system, and the prospective drug may also be introduced into the resulting cell culture, and the culture thereafter examined to observe any changes in the activity of the cells, or amount and extent of immune response indicator activity (for example, levels of IL-4 and/or IL-13; OX40L expression on dendritic cells; IFNAR1 levels on dendritic cells; and/or elevated numbers of CD4$^+$ T cells expressing GATA-3) due either to the addition of the prospective drug alone, or due to the effect of added quantities of the known peptides and/or agent(s).

Nucleic Acids

The present invention further provides an isolated nucleic acid encoding a protein, peptide, immune activator or agent of the present invention. Nucleic acid includes DNA and RNA. In a preferred aspect, the present invention provides a nucleic acid which codes for a polypeptide of the invention as defined above, including any one of SEQ ID NO: 2-12 or SEQ ID NO: 1 as set out herein.

The present invention also provides constructs in the form of plasmids, vectors, transcription or expression cassettes which comprise at least one polynucleotide as above. The present invention also provides a recombinant host cell which comprises one or more constructs as above. A nucleic acid encoding any specific binding member as provided herein forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression, a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of DNA sequences contemplated herein, particularly encoding the MMP-2 peptides SEQ ID NOs; 2-12, immune activator or agent of the invention. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Introduction

Matrix metalloproteinase-2 (MMP-2) is a proteolytic enzyme that degrades the extracellular matrix and is overexpressed by many tumors. Here, we document the presence of MMP-2-specific CD4$^+$ T cells in tumor-infiltrating lymphocytes (TILs) from melanoma patients. Strikingly, MMP-2-specific CD4$^+$ T cells displayed an inflammatory T$_H$2 profile, i.e. mainly secreting TNFα, IL-4 and IL-13 and expressing GATA-3. Furthermore, MMP-2-conditioned dendritic cells (DCs) primed naive CD4$^+$ T cells to differentiate into an inflammatory T$_H$2 phenotype through OX40L expression and inhibition of IL-12p70 production. MMP-2 degrades the type-I IFN receptor, thereby preventing STAT1 phosphorylation, which is necessary for IL-12p35 production. Active MMP-2, therefore, acts as a novel endogenous type-2 "conditioner" and may play a role in the observed prevalence of detrimental type-2 responses in melanoma.

Experimental Procedures

Reagents. Purified human MMP-2 (mixture of the proenzyme (50%) and the active form (50%)) was purchased from Biomol. The MMP-2 enzyme was inactivated either by heating to 56° C. for 45 min or by addition of the MMP-2 inhibitor III at 100 nM (Calbiochem) for 20 min rhPEX was purchased from Genway. rhMMP-9 (Calbiochem) was used as a mixture of the proenzyme (50%) and the active protein (50%). Overlapping peptides (20 amino acid long overlapping of 10) spanning proMMP-2 sequence were made by Proimmune (>80% pure). Proimmune uses PEPscreen technology, wherein peptides are synthesized on proprietary, state-of-the-art robotic platforms using optimized protocols based on Fmoc-chemistry. In terms of quality control, all peptides are analyzed by MALDI-TOF mass spectrometry to confirm their correct molecular weights. Lyophilized peptides were reconstituted in DMSO and were used either individually (2 µM) or as a pool (2 µM each). rhGM-CSF was purchased from Immunex. rhIL-12, rhIL-4, rhIL-7, rhIL-2 were from R&D Systems. The kits used for basophil isolation and IFNγ-secreting cell enrichment (Miltenyi Biotec) were used according to the manufacturer's instructions.

Antibodies. Allophycocyanin-conjugated antibody to CCR-7 (150503) was purchased from R&D Systems. Unconjugated (10 µg/mL for blocking experiments) or phycoerythrin-conjugated antibody to OX40L (11C3.1) was from Biolegend. Blocking antibody to IL-4 (8F12; 10 µg/mL) was from Acris. Antibodies to human Vβ chains covering 70% of the repertoire (10Test Beta Mark; Beckman Coulter) were used according to the manufacturer's instructions. Fluorescein isothiocyanate-conjugated antibody to IL-12p35/IL-12p70 (B-T21) and IFNAR1 (EP899Y) were from Abcam. Phycoerythrine-conjugated antibodies to IL-12p40/IL-12p70 (C8.6), IL-10 (B-T10), CD203c (FR3-16A11) were from Miltenyi Biotec. Blocking antibody to HLA-DQ (SPVL3; 20 µg/mL) was from NeoMarkers. Blocking antibodies to HLA-DP (B7/21; 20 µg/mL) or HLA-DR (L243; 20 µg/mL), phycoerythrine-conjugated antibodies to phosphorylated (Y701) STAT1 (4a), GATA-3 (L50-823), IL-2 (MQ1-17H12), IL-4 (8D4-8), IL-5 (JES1-39D10), IL-13 (JES10-5A2), TNFα (MAb11), IFNγ (25723.11), perforin (δG9), GranzymeB (GB11), CD40 (5C3), CD80 (L307.4), CD83 (HB15e), CD86 (IT2.2), HLA-DR (TU36), fluorescein isothiocyanate-conjugated antibodies to CD45RA (HI100) and CD45RO (UCHL1), and antibody to CD4 (RPA-T4) were purchased from BD Biosciences Pharmingen. Alexa fluor 488-conjugated antibody to IL-17 (eBio64DEC17), phycoerythrine-conjugated antibody to T-bet (4B10) and allophycocyanin-conjugated antibody to CD62L (DREG-56) were from eBioscience. Antiboby to β-actin (C-2) was from Santa Cruz Biotechnology.

T Cell culture, stimulation and priming. Peripheral blood mononuclear cells (PBMCs) were purified from healthy donor-(HD) or cord blood donor-(CB) derived buffy coats (New York Blood Center) by Ficoll-Paque Plus (GE Healthcare) centrifugation. CD4$^+$/CD25$^-$ cells were enriched (>90%) by magnetic cell sorting (Miltenyi Biotec) and primed/stimulated for 12-15 days either with irradiated (35Gy) autologous CD4$^-$ cells or with autologous mature DCs in IMDM (GIBCO) supplemented with 1 mM HEPES (Life Technologies), 2 mM L-glutamine (Sigma), streptomycin (100 UI/mL)/penicillin (100 µg/mL) (Sigma) and 5% heat inactivated pooled human serum (PHS; Valley Biomedical) in the presence of rhIL-2 (10 UI/mL) and IL7 (5 ng/mL) (R&D Systems). Antigen presenting cells (CD4$^-$ cells or DCs) were loaded either with peptides (2 µM) or with the MMP-2 protein (10 µg/mL) for 2 and 5 h, respectively. DCs were matured using the TLR3 agonist poly(I:C) at 5 µg/mL/$10^6$ DCs (Amersham). To generate T cell clones, we originally relied on our published methodology (Godefroy et al., 2006; Godefroy et al., 2007; the entire contents of each of which is incorporated herein by reference), involving enrichment of IFNγ-secreting cells upon short-term culture and peptide stimulation to generate MMP-2 responsive clones. Briefly, CD4$^+$ T cells were stimulated by CD4$^-$ cells irradiated and pulsed with peptides for 12 days in the presence of rhIL-2 and rhIL-7. CD4$^+$ T cells were then restimulated with peptides for 3 hours before capturing IFNγ-secreting specific cells using a bispecific antibody coating T cells and capturing produced IFNγ. Positive cells were purified magnetically before being cloned. Although MMP-2-specific cells could be isolated, it was realized that IFNγ secretion was marginal compared to their secretion of IL-4 and TNFα. IFNγ-secreting cells in response to MMP-2 peptide pool were enriched by cytokine-guided magnetic cell sorting (Miltenyi Biotec) as described above and cloned the following day by limiting dilution in the presence of irradiated allogeneic PBMCs, 1 µg/mL phytohemagglutinin-L (Sigma) and 150 UI/mL rhIL-2. Tumor infiltrating lymphocytes (TILs) were provided by Pr. F. Jotereau and B. Dréno. They were obtained from tumor-invaded lymph nodes of melanoma patients (stage Mb) and expanded ex vivo. These patients received autologous TILs and IL-2 infusions in a clinical trial (Labarriere et al., 2002). This protocol was approved by the Institutional Ethics Committee and registered with regulatory state authority in France (Nantes).

Lymphocytes can be obtained either from a classical Ficoll of the patient's blood or from tumor fragments (tumor infiltrating lymphocytes, TILs). In the latter case, TILs can be isolated by culturing cryopreserved fragments of melanoma-invaded lymph nodes in 12-well tissue culture plates with X-vivo 15 medium containing 150 IU/ml rhIL-2 and 1 nM glutamine for 10 to 14 days. To perform high-fold expansion, $1.8 \times 10^6$ of short-term culture TIL were plated at 300 viable lymphocytes/well with irradiated feeder cells into U-bottomed microplates in 200 µl rhIL-2 medium. Phytohemagglutinin was added on day 0 (15 µg/ml). After 48 h, most of the PHA was removed by replacing the culture medium. Ten days later, lymphocytes were removed from the culture plates, adjusted to $1 \times 10^6$ cells/ml in rIL-2 medium and transferred into culture trays for an additional 10 days before injection.

Dendritic cell preparation and activation. PBMCs were purified from healthy—(HD) or cord blood—(CB) donors and plated at $40 \times 10^6$ cells/10 mL/dish in complete IMDM with 5% PHS. Cells were allowed to adhere for 2 h at 37° C. Non-adherent cells were removed. The monocyte-enriched fraction was supplemented with 100 UI/mL rhGMCSF and 300 UI/mL rhIL-4 (R&D Systems) on days 0, 2 and 4. Immature DCs were harvested on day 5 and matured using poly(I:C) at 5 µg/mL/$10^6$ DCs (Amersham) Secretion of IL-12p70, TNFα, IL-1β, IL-6, IL-8 and IL-10 was assessed on both immature and mature DCs using the Human Inflammatory Cytokine Cytometric Bead Array (BD Pharmingen).

Enzyme-linked immunosorbent assay Activation of T cell clones (10,000 cells/100 µL/well), polyclonal T cell populations (100,000 cells/100 µL/well), DCs (50,000 cells/100 µL/well) and basophils (10,000 cells/100 µL/well) was determined by ELISA. IFNγ (BioSource), TNFα (BioSource), IL-4 (BioSource), TSLP (Quantikine; R&D Systems), IFNβ (VeriKine; PBL interferon source) and MCP-3 (DuoSet; R&D Systems) contents in supernatants were measured according to the manufacturer's instructions.

Intracellular staining T-bet and GATA-3 expression was measured on resting T cells. Cells were fixed (4% paraformaldehyde for 10 min at RT), permeabilized with 0.1% saponin, and stained for intracellular transcription factors. Cytokine production by T cells was also assessed by intracellular staining T cells were stimulated with 2 µM overlapping peptides. After 1 h, 10 µg/mL brefeldin A was added to the cells. Five hours later, T cells were stained for surface markers, fixed, permeabilized, and stained for intracellular cytokines (TNFα, IFNγ, IL-2, perforin, granzymeB, IL-4, IL-5, IL-10, IL-13 and IL-17). Antigen-specificity was defined by the percentage of cells secreting cytokine as long as it exceeded background (cytokine-secreting cells in the absence of peptide stimulation) by more than twofold and consisted of more than 0.5% of responding cells following subtraction of background for at least one cytokine. It was not uncommon to find relatively high background levels of IL-4 and TNFα producing T cells, likely due to the fact that these highly sensitive cells continued to produce cytokine up to 2-3 weeks after stimulation. For assessment of IL-4 production by basophils, brefeldin A was added simultaneously to stimulation. For intracellular staining of IL-12p35, IL-12p40 and phosphorylated STAT1, immature DCs were incubated with or without MMP-2 as described in the Brief Description of the Drawings. After 1 h, 5 µg/mL poly(I:C) was added to activate immature DCs. For monitoring IL-12 subunits, brefeldin A was added 4 h after poly(I:C) addition. DCs were then cultured for 12 h, fixed, permeabilized and stained for intracellular IL-12. For detection of STAT1 phosphorylation on Y701, DC were fixed 3 h after poly(I:C) addition, permeabilized and stained. Data were acquired with FACScalibur cytometer (BD Biosciences) and analyzed using FlowJo software.

Western blots IFNAR1 and β-actin were detected by Western blot analysis using rabbit and mouse mAbs, respectively. HRP-linked anti-rabbit (Cell Signaling) or anti mouse (Amersham Biosciences) IgG were used as secondary Abs before chemiluminescent detection (ECL Plus, Amersham Biosciences).

Statistical analysis Separate analyses were performed for each experiment individually. Analyses take into account paired observations within donors when appropriate (e.g., MMP-2 vs no MMP-2, active vs inactive, active vs peptides). For three-group comparisons (i.e., MMP-2, Melan-A, NY-ESO-1), analyses of variance were performed for an overall comparison among independent groups, and t-tests were then used for specific pairwise comparisons between groups. Within each analysis, p-values were adjusted for multiple comparisons using a Bonferroni correction. For analyses in which each of two groups was compared to a third group (i.e., two comparisons, with no overall test of the three groups), two t-tests were performed, using the Bonferroni adjustment for the two analyses. Two-sided statistical tests were performed at an overall alpha-level of 0.05, with adjustments for multiple comparisons, as described above. Details for each analysis are provided in the Brief Description of the Drawings.

Results

MMP-2-Specific CD4$^+$ T Cell Responses in Melanoma Patients

Figure 1A:
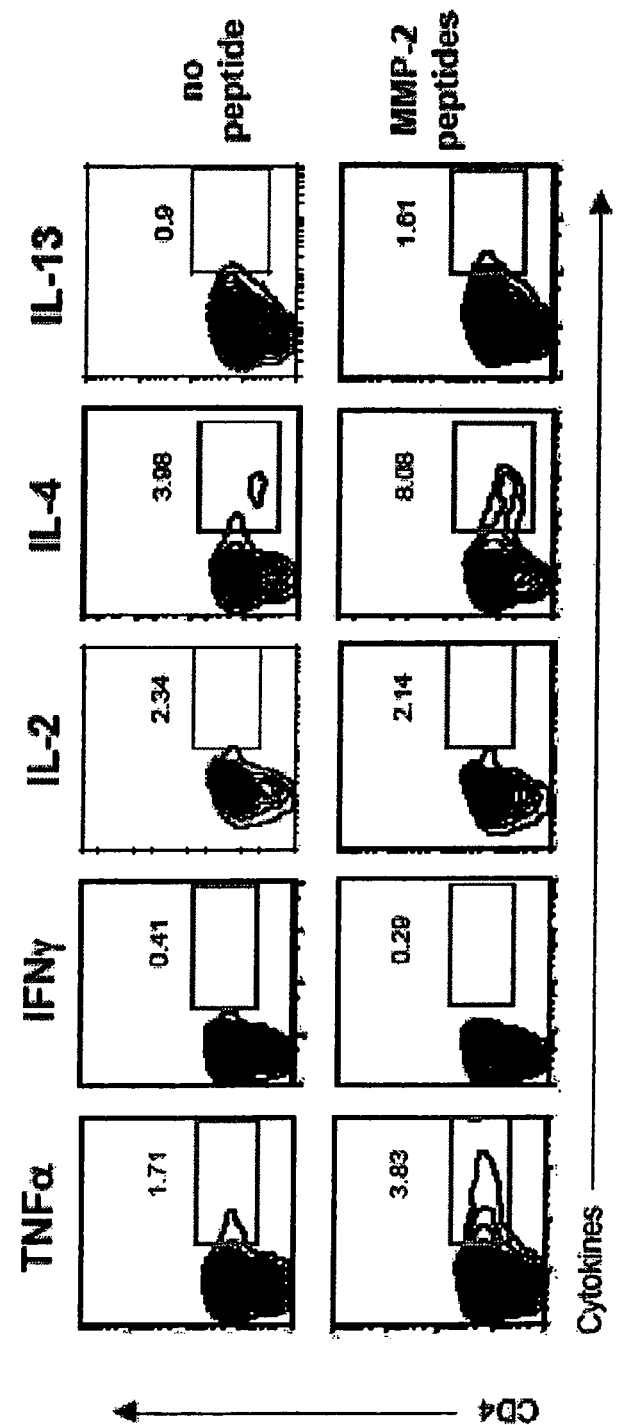
FIG. 1A-B shows MMP-2-specific CD4+ T cell responses in melanoma patients. TILs from representative melanoma patient M186 (A) or from 31 unselected patients (B) were stimulated with the MMP-2 peptide pool (2 μM) for 6 h and assessed for cytokine production by intracellular staining Percentage of secreting cells upon peptide stimulation was considered specific/positive when it exceeded by more than twofold the background (cytokine-secreting cells in the absence of stimulation) and had more than 0.5% of responding cells (after background subtraction) for at least one cytokine. See also FIG. 9 for MMP-2-derived peptides and patient survival analysis.
Figure 1B:
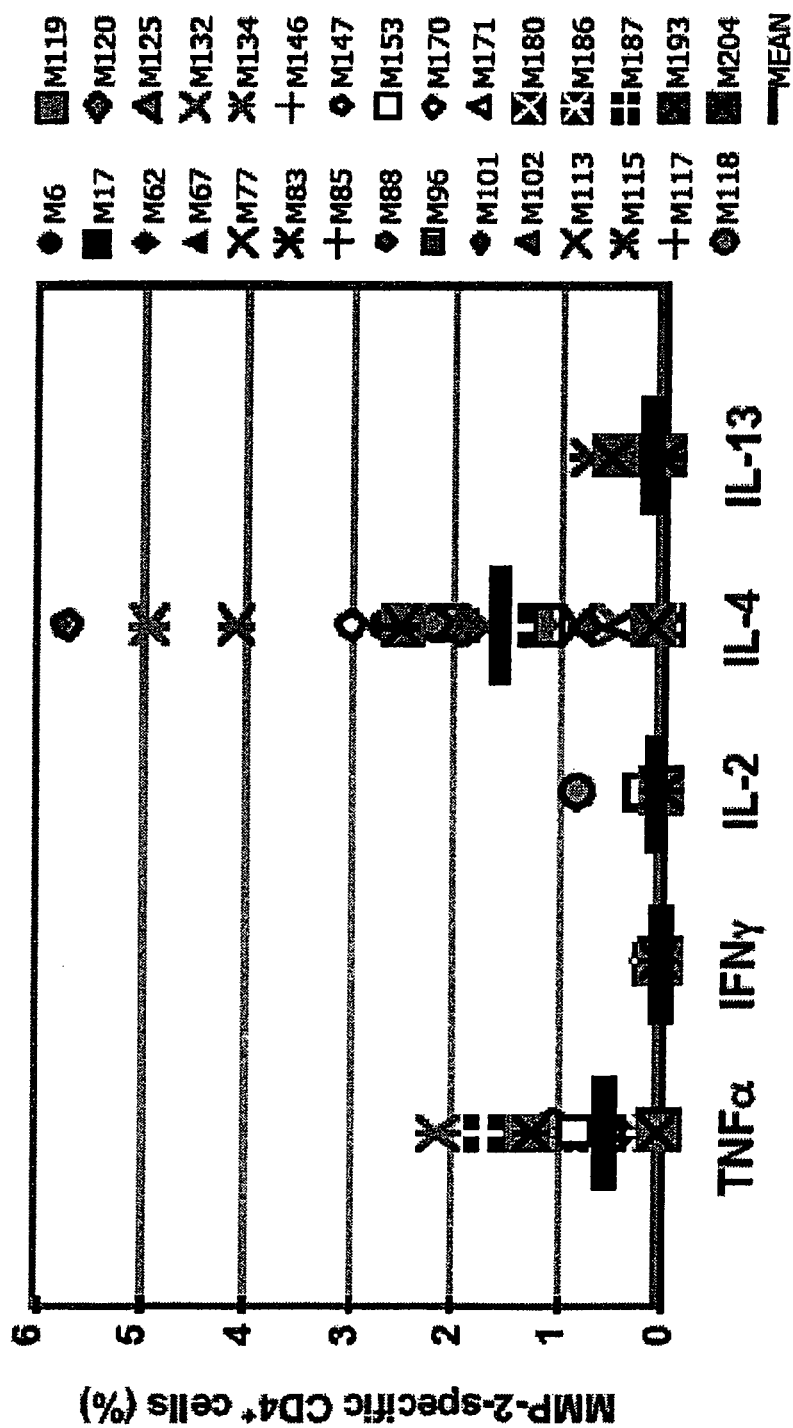

Whether CD4$^+$ T cells recognize MMP-2-derived epitopes has not previously been established. We used a pool of 20 amino acid long, partially overlapping peptides spanning the entire sequence of MMP-2 (FIG. 9A) to evaluate specific responses in TILs derived from melanoma patients, in some of whom we had previously detected MMP-2-specific CD8$^+$ T cells infiltrating their tumors and whose tumor cells produced MMP-2 protein (Godefroy et al., 2005). Strikingly, MMP-2-specific CD4$^+$ T cells were found in 13 out of 31 unselected TIL populations (FIG. 1A-B). Among these 13 responders, the percentage of cells secreting TNFα upon stimulation ranged from 0.04 to 2.12% (mean=0.78%±0.53) and IL-4 from 1.17 to 4.91% (mean=2.44%±1.21). Very few cells produced IFNγ and IL-2 (FIG. 1A-B). Therefore, more than 40% of tested TILs contained MMP-2-specific CD4⁺ T cells preferentially secreting IL-4 and TNFα.

Figure 9B:
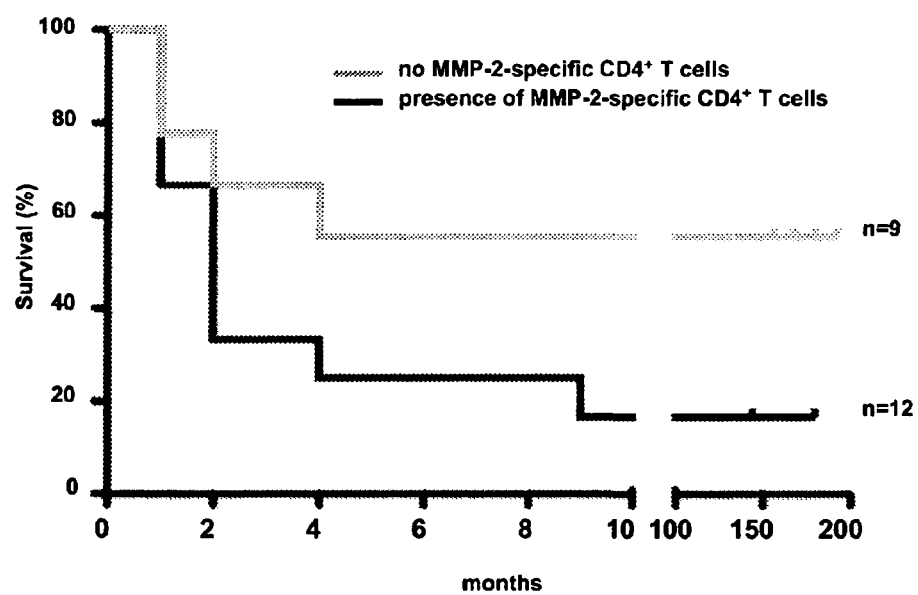

To try to evaluate whether these TILs played any therapeutic role, we assessed the clinical outcome of patients who had CD4⁺ TILs targeting MMP-2. Survival status was available for 21 of these patients. Twelve patients displayed MMP-2-specific CD4⁺ T cell responses and demonstrated a trend towards a poorer clinical outcome compared to patients with no detectable MMP-2 responses (FIG. 9B). The observed difference in patient survival was, however, not statistically significant (p=0.121). The lack of a significant difference (p=0.121) could be explained not only by the limited number of patients available, but also by other critical factors such as the number of lymph nodes invaded, T cell responses to other antigens and patient treatment (Dreno et al., 2002; Khammari et al., 2007; Labarriere et al., 2002). Accordingly, the results to date suggest that if a patient has MMP-2-specific CD4⁺ TILs, such patients merit more particular attention and more aggressive treatment. Additional studies are, however, ongoing to collect data pertaining to survival in a larger patient cohort.

MMP-2-Specific CD4⁺ T Cell Responses in Healthy Donors

Figure 2A:
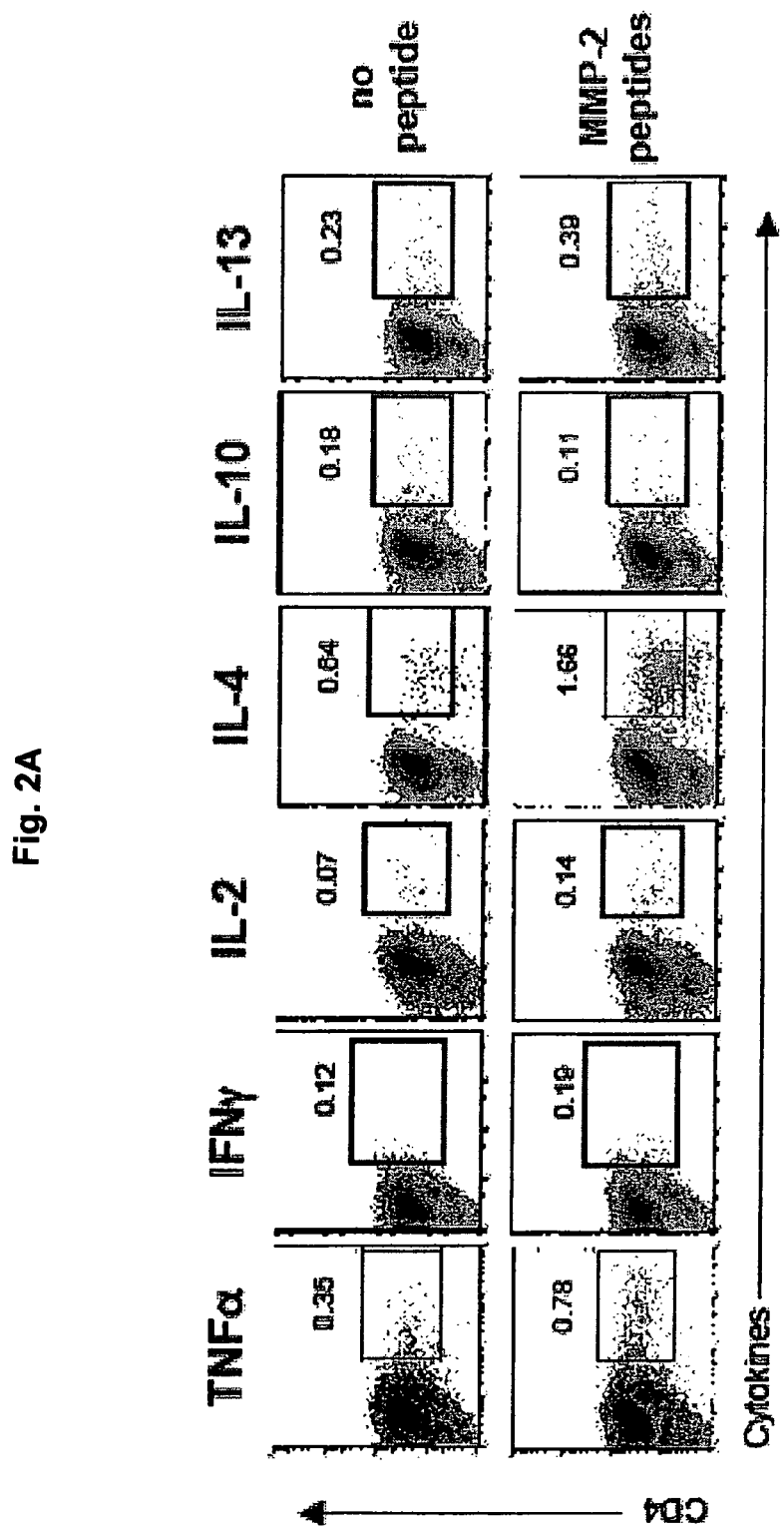
FIG. 2A-D shows MMP-2-specific polyclonal CD4+ T cell responses in healthy donors. (A) Isolated CD4+/CD25− T cells from 16 healthy donors were individually stimulated with the MMP-2 peptide pool (2 μM) pulsed on the irradiated (35 grays) autologous CD4− fraction. 12 days later, cells were re-stimulated in an auto-presentation manner (no APCs), with the same peptides (2 μM) for 6 h, and assessed for cytokine production by intracellular staining Density plots represent cytokine production by representative donor HD9759. (B) Percentages of MMP-2-specific CD4+ T cells (% of producing CD4+ cells after peptide stimulation—% of producing CD4+ cells non-stimulated (background)) are shown for all donors. Percentage of secreting cells upon peptide stimulation was considered specific/positive when it exceeded by more than twofold the background (cytokine-secreting cells in the absence of peptide stimulation) and had more than 0.5% of responding cells (after background subtraction) for at least one cytokine. (C) Ex vivo PBMCs from 6 healthy donors were stimulated by adding the MMP-2 peptide pool (2 μM) onto the cells (no specific APCs were targeted). The gating strategy for visualizing memory CD4+ T cells is shown on the left plot. Density plots showing cytokine production of CD4+/CD45RO+/CD62L− memory cells are represented for representative donor HD7957. Percentages of producing cells among CD4+/CD45RO+ gated cells are indicated. (D) MMP-2-specific memory CD4+ T cell responses for all donors are represented. CD4+/CD45RO+/CD62L+ naive cells derived from healthy (n=6) and cord blood (n=9) donors were used as controls. See also FIG. 10.
Figure 2B:
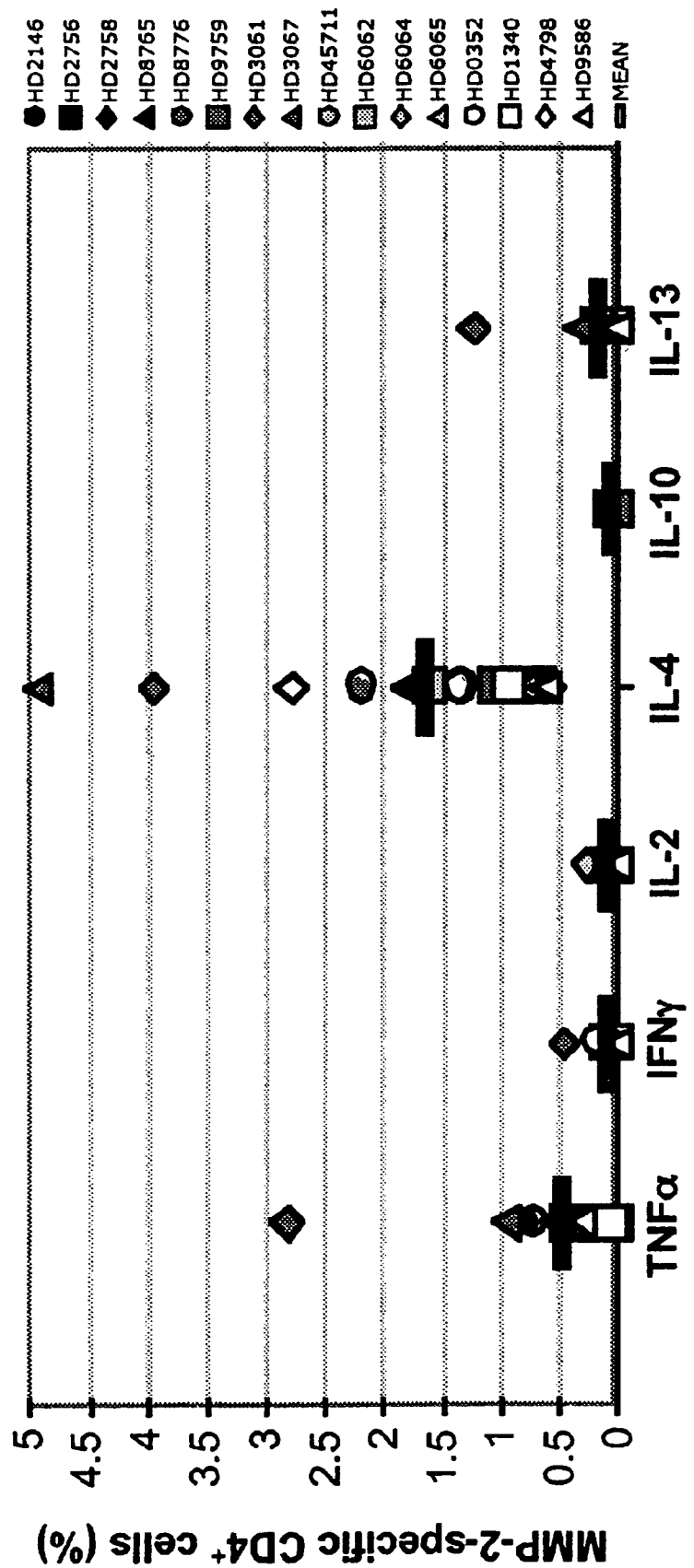
Figures 2C, 2D:
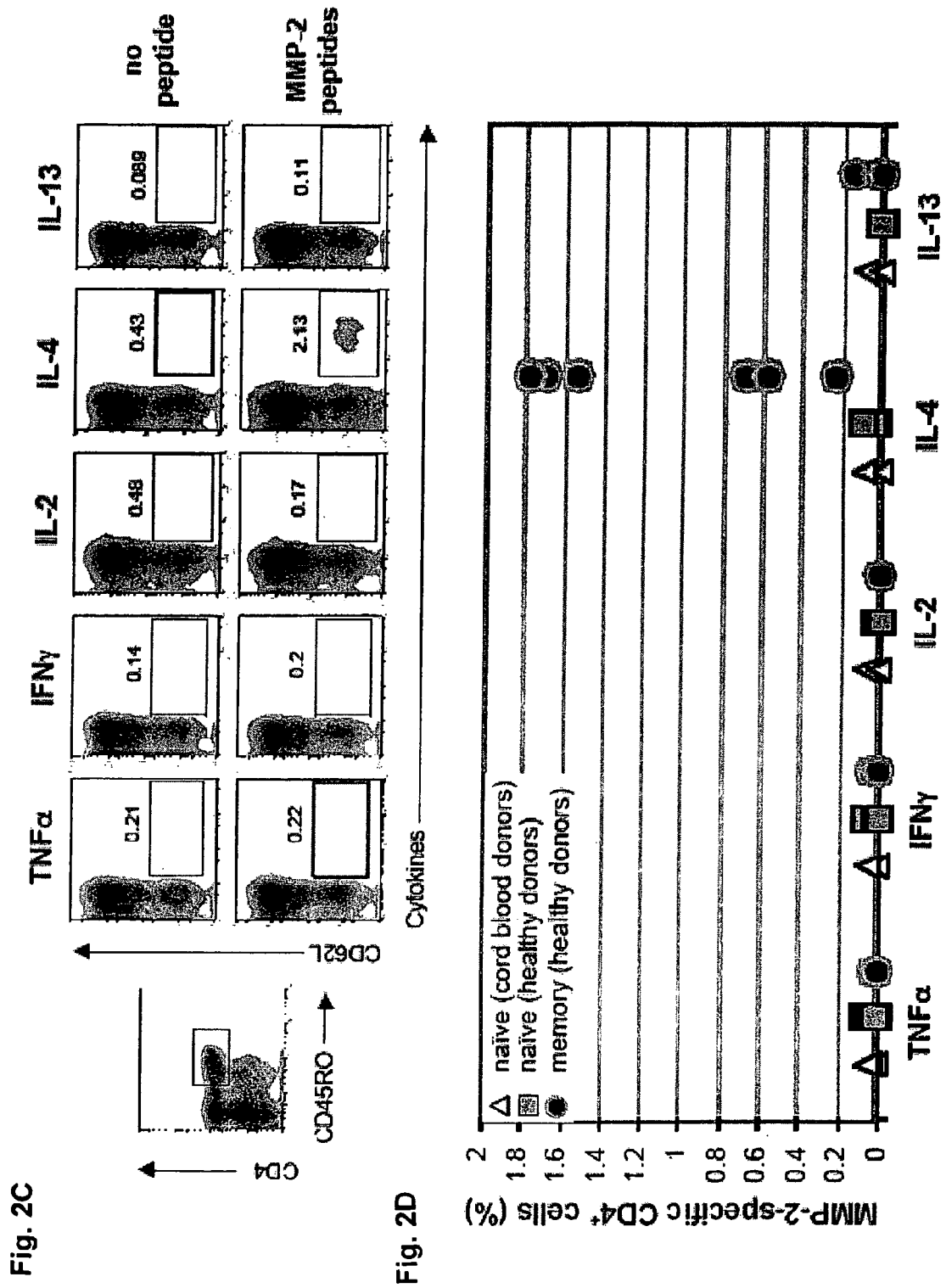

To further study and characterize MMP-2-specific CD4⁺ T cells, we stimulated circulating isolated CD4⁺ cells from 16 healthy donors with the same pool of MMP-2 peptides. Twelve days later, cultures were assessed for MMP-2-specific CD4⁺ T cells by monitoring intracellular cytokine staining upon stimulation with the peptide pool. We derived 14 MMP-2-reactive polyclonal populations (FIG. 2A-B). Among these 14 responders and upon peptide re-stimulation, the percentage of cells secreting TNFα ranged from 0 to 2.8% (mean=0.46%±0.69), IFNγ from 0 to 0.44% (mean=0.07%±0.11), IL-2 from 0 to 0.24% (mean=0.06%±0.06), IL-4 from 0.55 to 4.93% (mean=1.69%±1.3) and IL-13 from 0 to 1.21% (mean=0.15%±0.31) (FIG. 2B). No MMP-2-specific CD4⁺ T cells secreted IL-10 and very few cells secreted type-1 cytokines (FIG. 2A-B). To determine whether MMP-2 responses can be detected directly ex vivo, we stimulated PBMCs from 6 healthy donors with MMP-2 peptides and measured their cytokine responses. Responding gated CD4+ memory T cells (CD4⁺/CD45RO⁺/CD62L⁻) secreted IL-4 (mean=1.09%±0.61 of CD4⁺/CD45RO⁺ cells), but none of the other cytokines (FIG. 2C-D). The absence of a detectable TNFα response is likely due to the small percentage of MMP-2-specific CD4⁺ T cells, producing cytokine below the detection threshold. Gated naive CD4⁺/CD45RA⁺/CD62L⁺ T cells, derived either from healthy donors or cord blood, were used as controls, and failed to respond to the MMP-2 peptides (FIG. 2D). Therefore, MMP-2-specific CD4⁺ T cells can be frequently expanded from normal donors and secrete primarily TNFα and IL-4, but little type-1 cytokines and no IL-10, consistent with an inflammatory $T_H2$ profile (Ito et al., 2005; Soumelis et al., 2002) acquired in vivo.

Figure 11A:
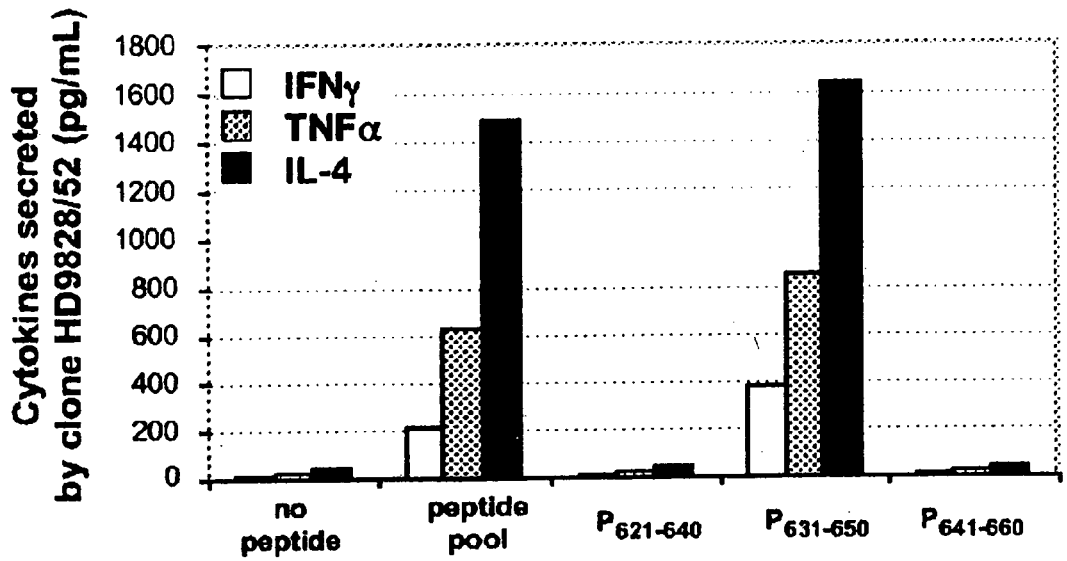
FIG. 11A-D shows MMP-2-specific CD4+ T cell responses in humans (related to FIG. 3). (A) MMP-2-specific CD4+ T cell clones were generated and characterized as described in Experimental Procedures. Clone HD9828/52 is shown as a representative example. Epitope specificities were assessed after overnight stimulation with individual peptides (2 μM). IFNγ, TNFα and IL-4 release was measured by ELISA. (B) All MMP-2-specific CD4+ T cell clones were characterized by staining for CD4, CD8 and TCR Vβ chain expression. Clone HD9828/52 is shown as a representative example. (C) To establish HLA class-II isotype restriction, CD4+ T cell clones were stimulated by corresponding peptides in the absence or presence of blocking mAb (10 μg/mL) for HLA-DP, HLA-DQ or HLA-DR and IFNγ release was measured by ELISA. (D) Purified CD4+/CD25− cells were stimulated for 12 days by autologous DCs incubated with MMP-2 protein (10 μM) and subsequently washed. MMP-2-specific CD4+ T cells were detected by intracellular staining of IFNγ, TNFα and IL-4 after 6 hours of stimulation with MMP-2 peptide pool (2 μM). Numbers in the upper right quadrants are the percentages of each population.
Figure 11B:
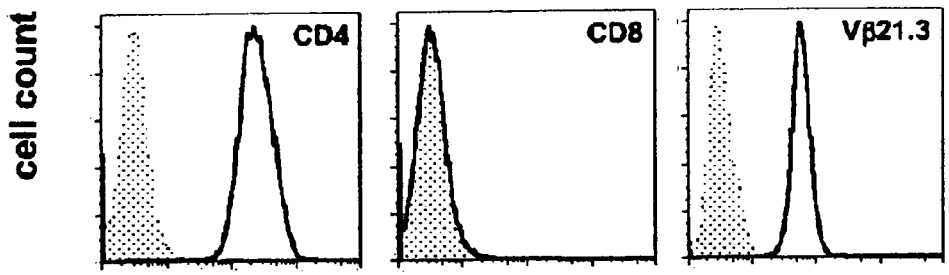
Figure 11C:
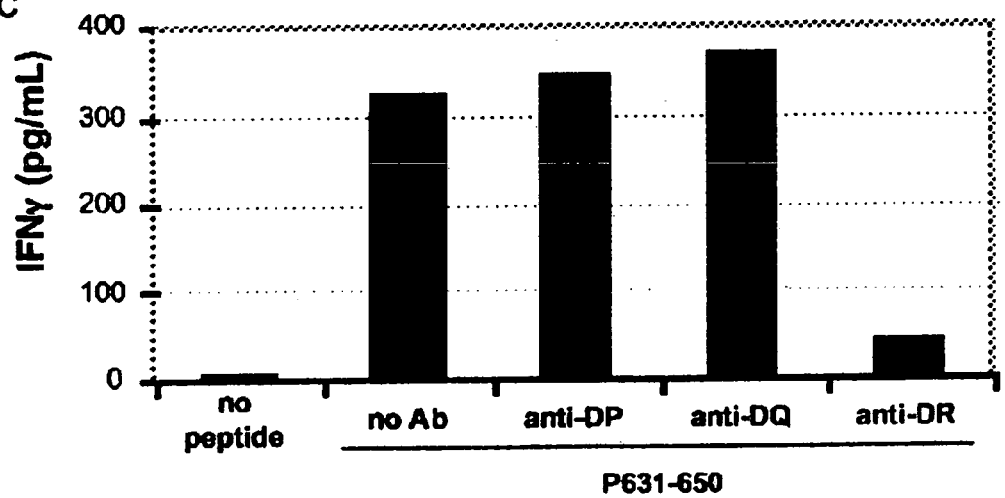

To more accurately characterize the in vitro MMP-2-specific CD4⁺ T cell differentiation state, T cell clones were generated from healthy donors (FIG. 10B). Nineteen CD4⁺ T cell clones responding to the MMP-2 peptide pool were subsequently characterized (as exemplified by clone HD9828/52) for epitope specificity (FIG. 11A), CD4/CD8, TCR Vβ expression (FIG. 11B) and HLA class-II isotype restriction (FIG. 11C). Results for all CD4⁺ T cell clones are shown in FIG. 16: Table 1. We looked for production of TNFα, IL-4 and IFNγ upon stimulation with individual peptides separately to assess epitope specificities. Nineteen CD4⁺ T cell clones recognized eleven distinct and novel MMP-2-derived peptides, within the following amino acid positions: 1-20, 11-30, 21-40, 41-60, 161-180, 361-380, 551-570, 571-590, 601-620, 621-640 and 631-650 (FIG. 11A and FIG. 16: Table 1). Antibodies towards most TCR Vβ chains were used to confirm clonality and distinguished at least 13 distinct clones among the original 19 CD4⁺ T cell clones (FIG. 11B and FIG. 16: Table 1), as >99% of each culture expressed only one Vβ chain. Blocking antibodies against HLA class II isotypes showed that most of the MMP-2-specific T cell clones were HLA-DR restricted (FIG. 11C and FIG. 16: Table 1).

Figure 11D:
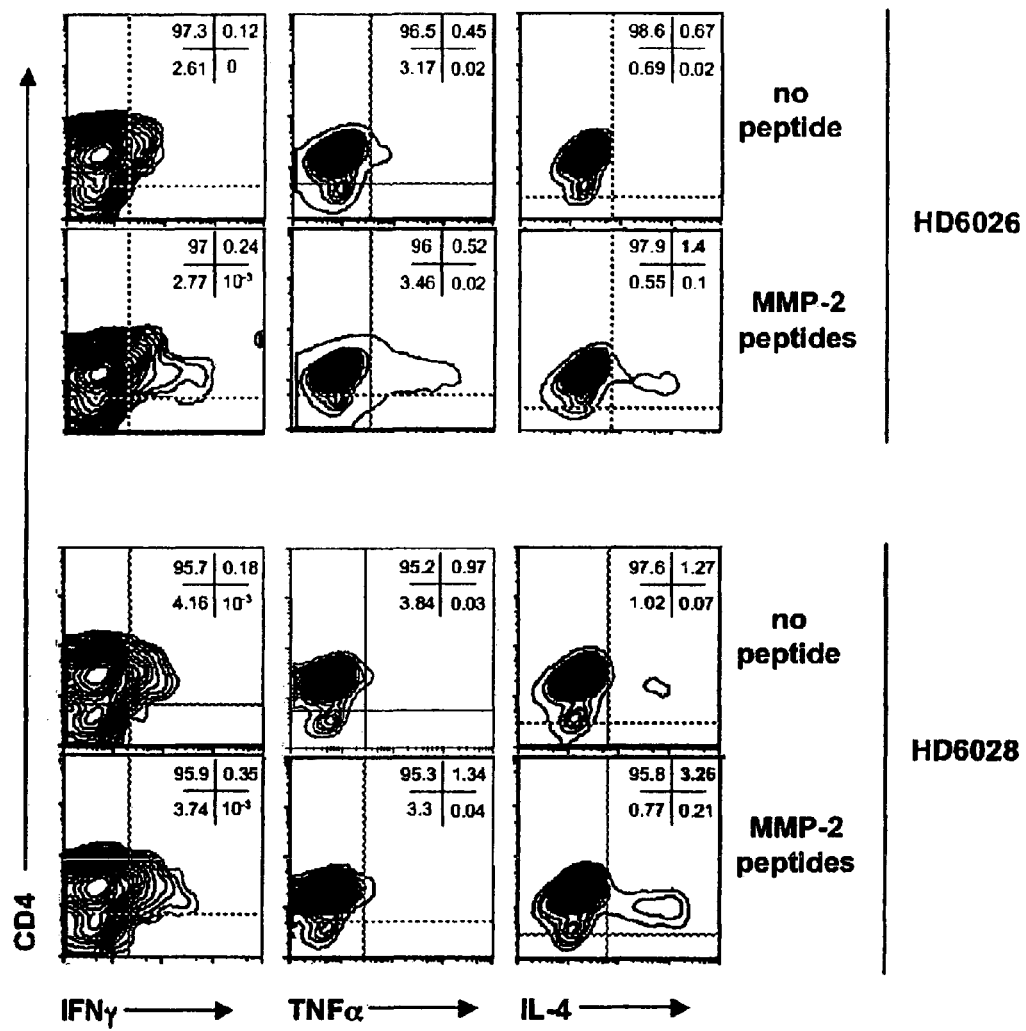

To assess the physiological relevance of MMP-2-derived epitope presentation, CD4⁺ T cells from healthy donors were stimulated with autologous DCs loaded with whole MMP-2 protein. Twelve days later, we tested T cell responses to the peptide pool. Donors HD6026 and HD6028 had 0.12% and 0.17% of cells secreting IFNγ as well as 0.73% and 1.99% secreting IL-4, respectively (FIG. 11D). These results showed, on the one hand, that the whole protein is naturally processed and presented by DCs to T cells and, on the other hand, that MMP-2-specific human CD4⁺ T cells preferentially secrete IL-4 upon DC stimulation.

MMP-2-Specific CD4⁺ T Cells Display an Inflammatory $T_H2$ Phenotype

Because the majority of MMP-2-specific CD4⁺ T cell clones, upon peptide stimulation, secreted more IL-4 and TNFα than IFNγ (FIG. 11A), we tested them for production of a broader panel of cytokines to further assess their cytokine profile. MMP-2-specific T cell clones, as shown by the representative clone HD5950/MC2/43 (FIG. 3A) or the 19 clones (FIG. 3B), secreted mainly TNFα (mean=38.2% of secreting cells, after background subtraction), IL-4 (mean=23.5%) and IL-13 (mean=19.7%), but fewer cells produced IFNγ (mean=6.2%) and IL-2 (mean=5.7%). This profile again corresponds to an inflammatory $T_H2$ phenotype (Ito et al., 2005; Soumelis et al., 2002).

Figure 3B:
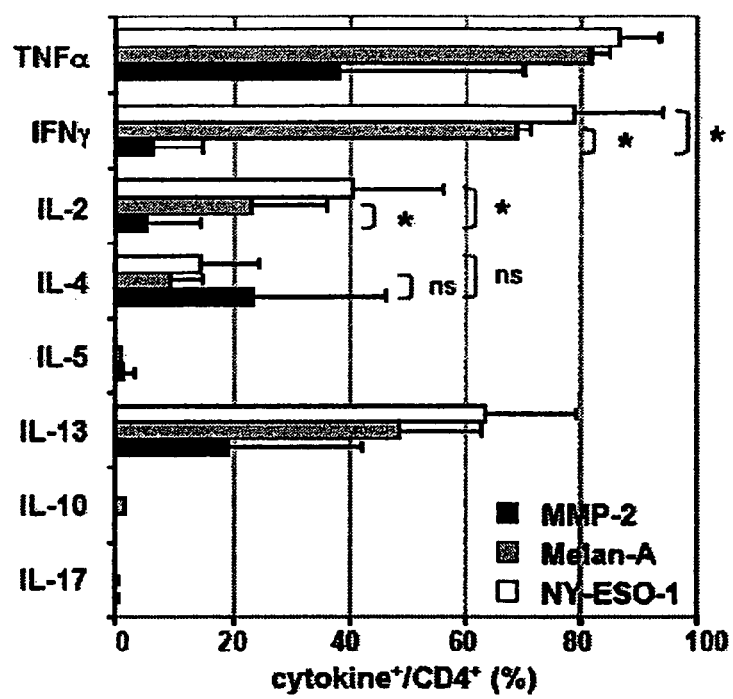
Figure 3C:
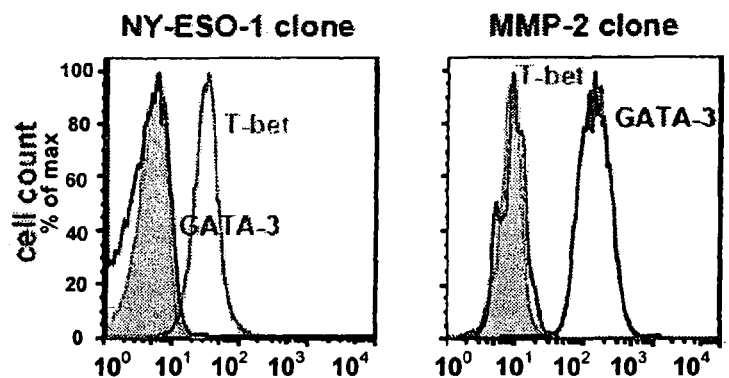
Figure 3D:
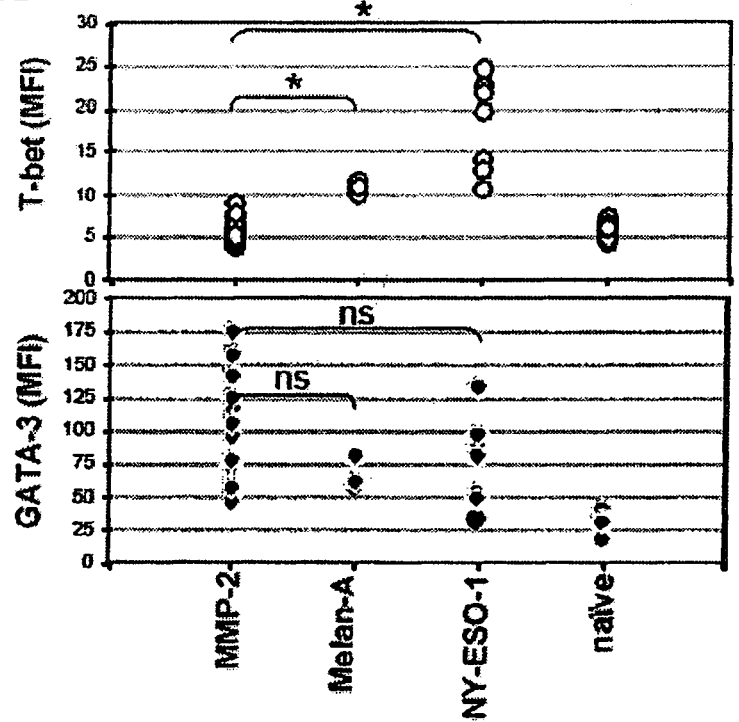

Because of the unique inflammatory $T_H2$ profile of MMP-2-specific CD4⁺ T cells, we next examined CD4⁺ T cell responses to other MAA, under the same conditions. CD4⁺ T cells from healthy donors were stimulated with overlapping 20 amino acid long peptides spanning the length of the differentiation antigen Melan-A/MART-1 and the cancer testis antigen NY-ESO-1 sequences. Antigen-specific T cells were then enriched before generating antigen-specific CD4⁺ T cell clones. We obtained 3 CD4⁺ T cell clones specific for Melan-A/MART-1 (recognizing the epitopes $P_{21-40}$, $P_{51-70}$ and $P_{61-80}$) and 8 for NY-ESO-1 (recognizing $P_{61-80}$, $P_{81-100}$, $P_{119-143}$, $P_{131-160}$, $P_{139-160}$, and $P_{161-480}$). Upon peptide stimulation, these clones secreted TNFα (mean=84.8% of secreting cells after background subtraction), IFNγ (mean=76.1%; overall ANOVA p≤0.0001, compared to MMP-2-specific T cell clones), IL-2 (mean=35.0%; overall ANOVA p≤0.0001 compared to MMP-2-specific T cell clones) and IL-13 (mean=58.5%), but low amounts of IL-4 (mean=14.1%) (FIG. 3B). To further characterize and compare MMP-2-, Melan-A/MART-1- and NYESO-1-specific T helper profiles, clones were stained for type-1 and type-2-associated transcription factors, T-bet and GATA-3 respectively. MMP-2-specific T cell clones expressed GATA-3 (mean MFI (mean fluorescence intensity)=105) and insignificant levels of T-bet (mean MFI=5.5), while Melan-A/MART-1- and NY-ESO-1-specific T cell clones expressed T-bet (mean MFI=16.6) and lower amounts of GATA-3 (mean MFI=72.3), confirming that CD4⁺ T cells recognizing MMP-2 exhibited a $T_H2$-like phenotype (FIG. 3C-D). Cord blood-derived naive CD4+ T cells, gated on CD4+/CD45RA+/CD62L+ cells, were used as a negative control (FIG. 3D).

Figure 4B:
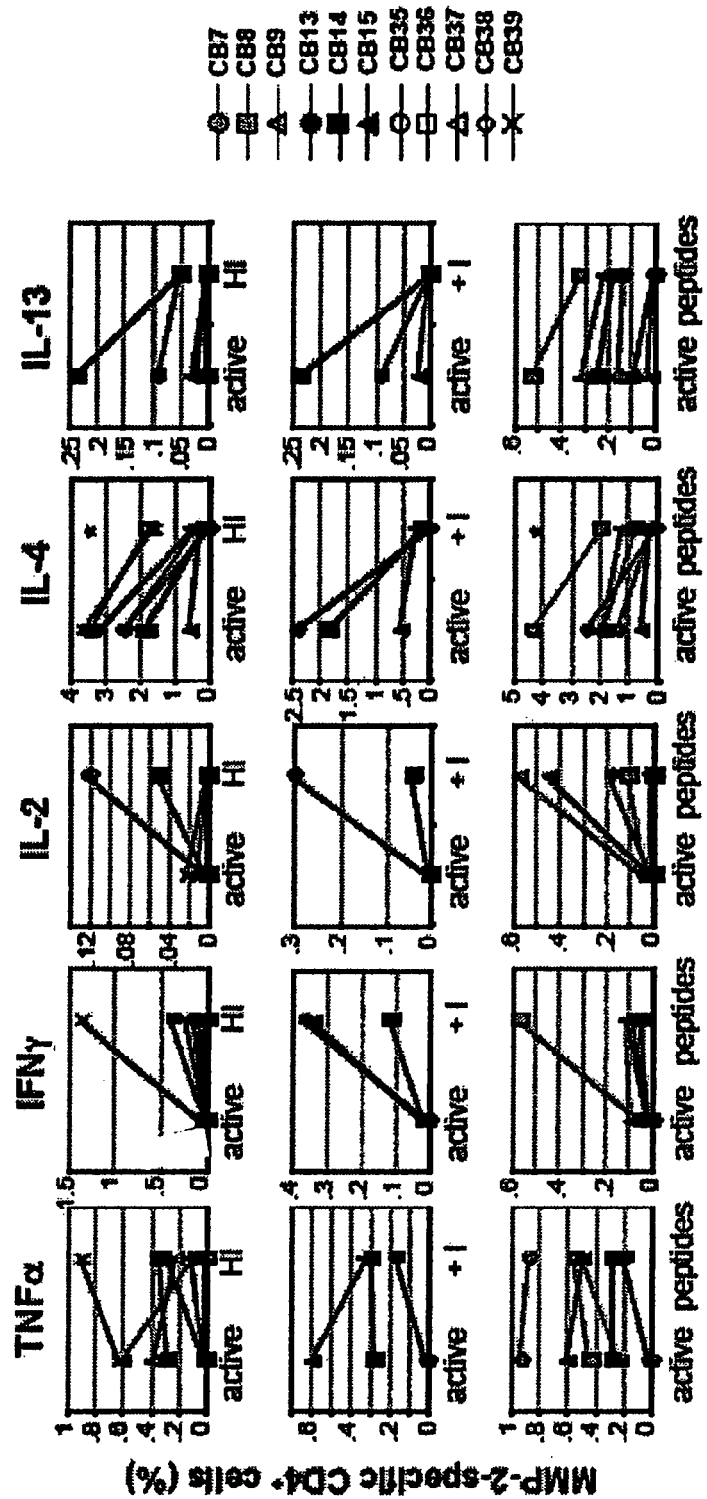

Active MMP-2 Enzyme is Required for Differentiation of Naive MMP-2-Specific CD4+ T Cells into Inflammatory $T_H2$ Cells To determine whether the active full-length protein was required for MMP-2-specific CD4+ T cells to differentiate towards an inflammatory $T_H2$ phenotype, we primed naive CD4+ T cells (from 11 cord blood donors) in vitro using autologous CD4− cells loaded with different sources of MMP-2: overlapping peptides, or the protein in its active or inactive conformation. The CD4− fraction was used as a source of APCs to include any cell type that could potentially be involved in priming. Peptide-specific responses (TNFα, IFNγ, IL-2, IL-4 and IL-13) of primed T cells were measured after 15 days. The percentage of MMP-2-specific CD4+ T cells secreting IL-4 (after background subtraction) was significantly higher when cells were primed with the active MMP-2 (mean=2.38%), rather than with peptides (mean=0.71%; mean of the individual differences=1.34, $p \leq 0.013$) or inactivated MMP-2, whether inactivation occurred by heating (mean=0.45%; mean of differences=1.80, $p \leq 0.0002$) or using a specific inhibitor (mean=0.12%; mean of differences=1.47, ns) (FIG. 4A-B). Furthermore, active MMP-2-primed cells produced less IFNγ and IL-2 compared to inactive MMP-2 or peptides (FIG. 4A-B). Thus the inflammatory $T_H2$ lineage commitment of MMP-2-specific CD4+ T lymphocytes depends on the presence of active MMP-2 both as a source of antigen and as an endogenous $T_H2$ conditioner.

Active MMP-2 Also Influences Other Tumor-Specific T Helper Differentiation

Figure 5B:
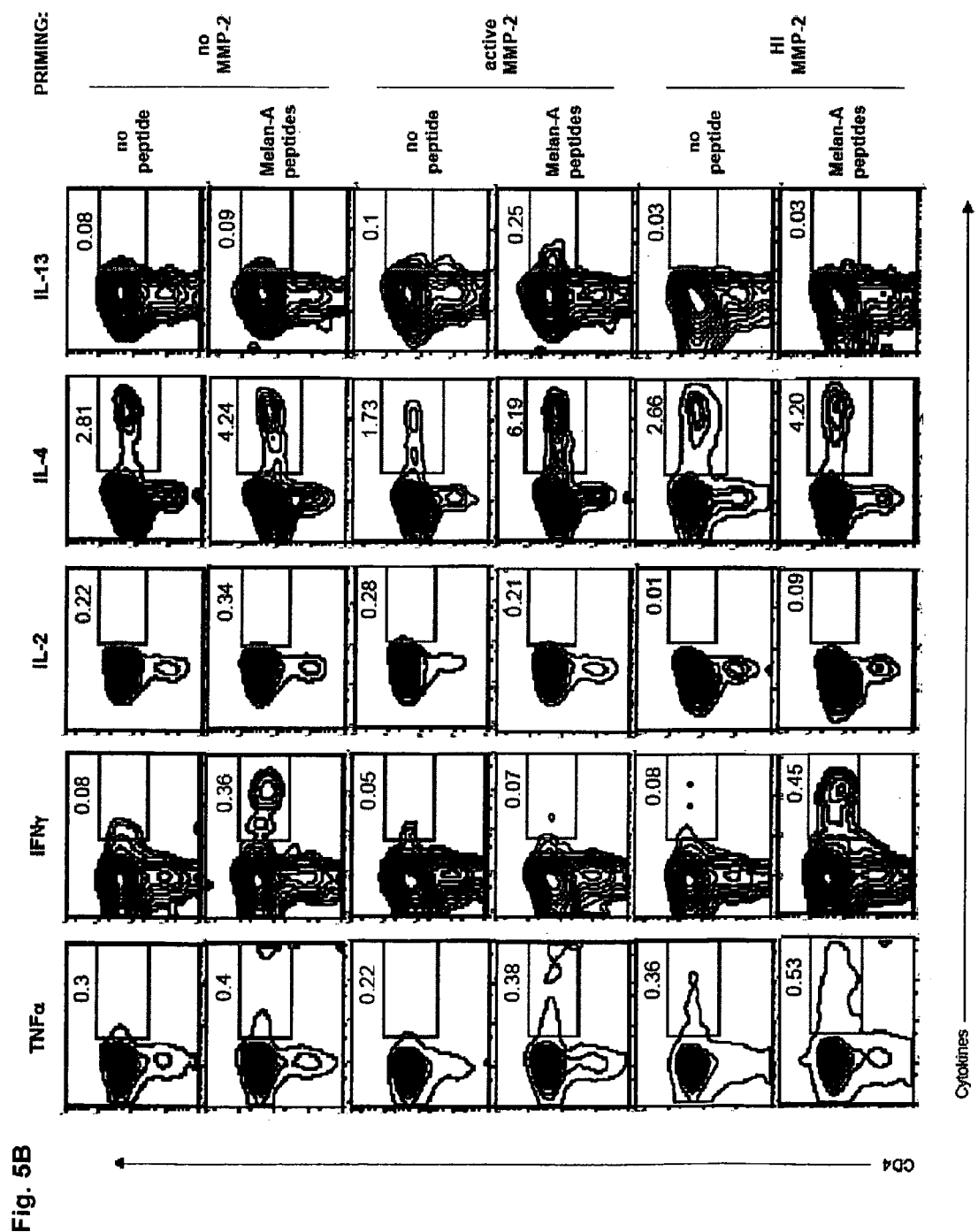

To evaluate whether active MMP-2 also affected CD4+ T cell differentiation specific for other MAA in a bystander fashion, naive CD4+ T cells from 10 cord blood donors were primed to Melan-A/MART-1 or NY-ESO-1 using autologous poly(I:C)-matured DCs pulsed with the corresponding overlapping peptides. After 15 days, primed CD4+ T cells secreted IFNγ (mean=0.23% of secreting cells after background subtraction) and IL-2 (mean=0.15%). CD4+ T cells specific for either tumor associated antigen, secreted little IL-4 and IL-13 (mean=0.75% and 0.02%, respectively) (FIG. 5A-B). On the other hand, when DCs were pre-incubated with active MMP-2 before maturation with poly(I:C), both Melan-A/MART-1-(FIG. 5A-B) and NY-ESO-1-specific (FIG. 5A) primed CD4+ T cells significantly failed to produce type-1 cytokines ($p \leq 0.0004$ and $p \leq 0.0073$ for IFNγ and IL-2, respectively) upon peptide re-stimulation (FIG. 5A-B). Primed CD4+ T cells instead significantly produced more IL-4 (mean=2.50%; mean of differences=1.85, $p \leq 0.0001$) and IL-13 (mean=0.08%; mean of differences=0.07, $p \leq 0.0174$) (FIG. 5A-B). In addition, CD4+ T cells primed using DCs pre-incubated with heat-inactivated MMP-2 significantly secreted similar cytokines than CD4+ T cells primed in the absence of MMP-2. Accordingly, the former CD4+ T cells (primed with HI MMP-2) were significantly different relative to CD4+ T cells primed in the presence of active MMP-2 (mean of differences=0.21 with $p \leq 0.0007$ for IFNγ, mean of differences=0.11 with $p \leq 0.015$ for IL-2 and mean of differences=1.92 with $p < 0.0001$ for IL-4) (FIG. 5A-B). Therefore, pre-exposure to active MMP-2, but not to inactive MMP-2, confers DCs with the ability to skew the differentiation of naive CD4+ T cells towards a $T_H2$-like phenotype, regardless of their antigen-specificity. Hence, MMP-2 could participate in the detrimental $T_H2$ skewing observed in certain tumors, including melanoma, thus impairing host anti-tumor immune responses (Botella-Estrada et al., 2005; Lauerova et al., 2002; McCarter et al., 2005; Minkis et al., 2008; Tatsumi et al., 2002).

Figure 12A:
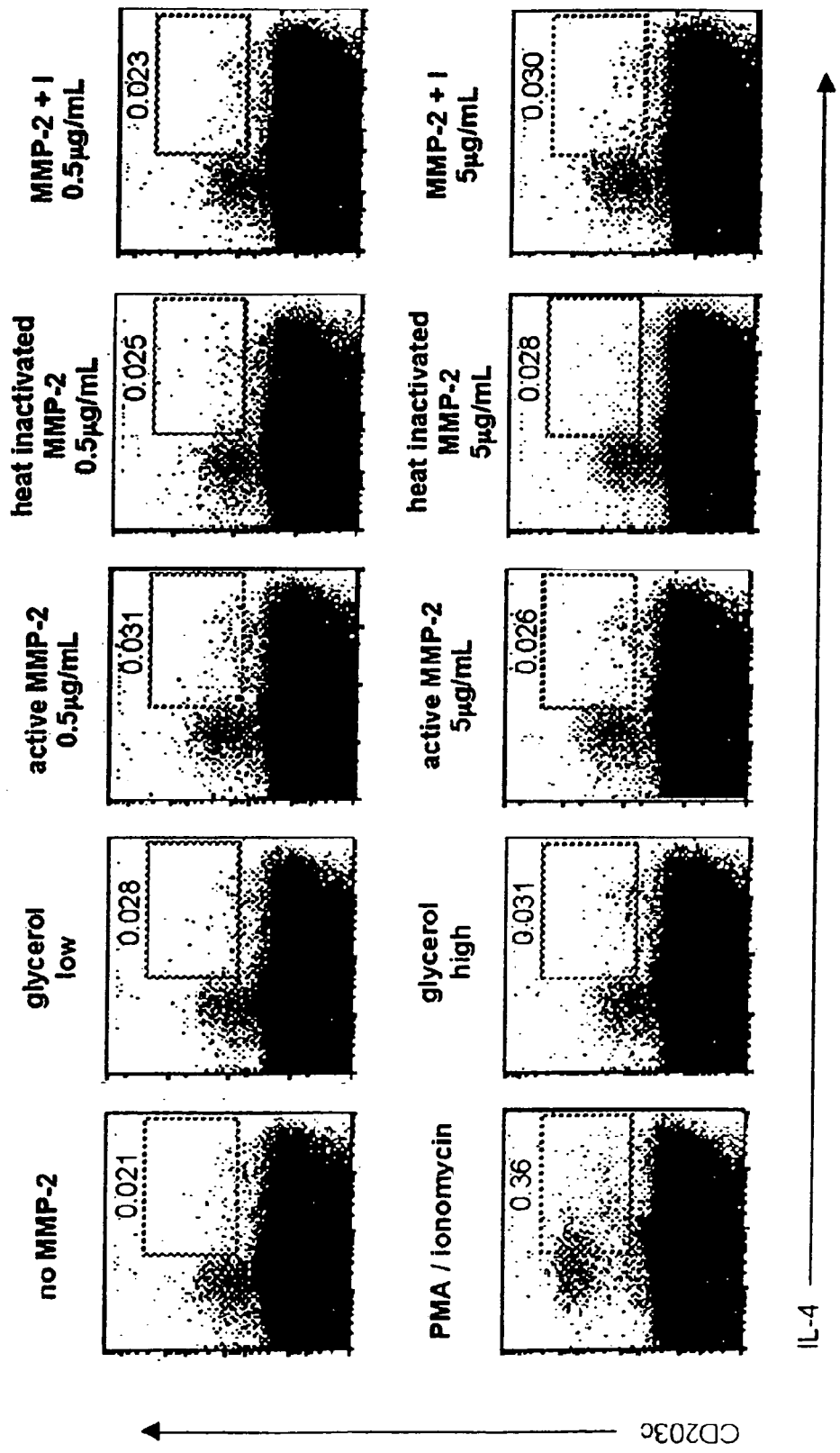
FIG. 12A-C shows that MMP-2 does not activate basophils (related to FIG. 6). (A) PBMCs from 3 healthy donors were incubated as indicated for 6 h in the presence of brefeldin A. Cells were stained for CD203c, a specific/activation marker for basophils, fixed with 4% paraformaldehyde, and stained for intracellular IL-4. Percentages of IL-4-producing basophils are indicated. (B,C) Enriched basophils were cultured for 16 h with MMP-2 (0.5 μg/mL and 5 μg/mL) as indicated. IL-4 (B) and TSLP (C) levels in supernatants were assessed by ELISA.
Figure 12B:
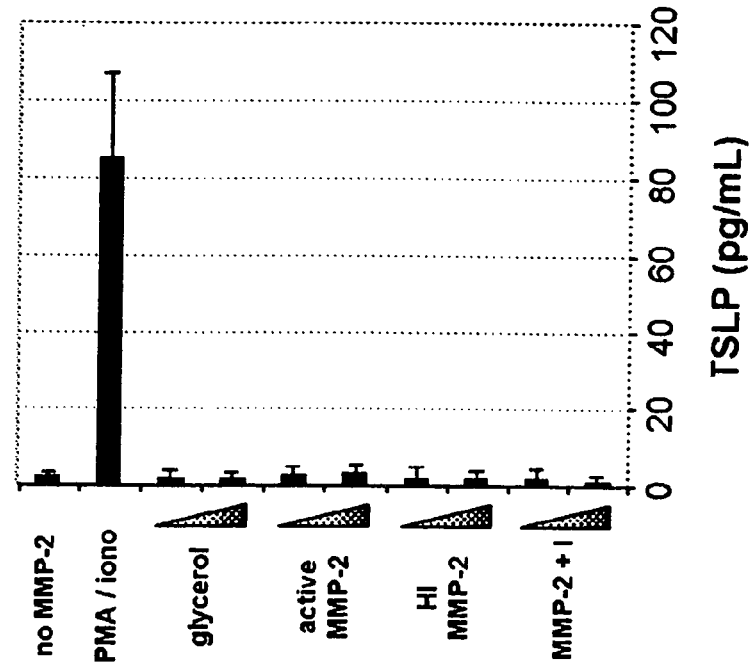
Figure 12C:
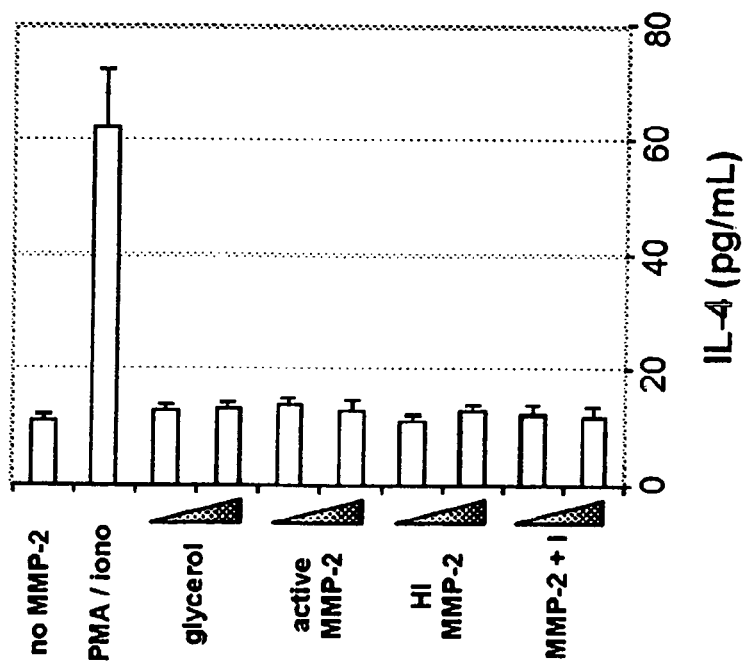

MMP-2 Induces Inflammatory $T_H2$ Cells in a Basophil-independent but DC Dependent Manner We next studied the cellular requirements underlying the inflammatory $T_H2$ polarization of MMP-2-specific cells. Basophils, recently described as APCs (Sokol et al., 2009), are thought to play an important role in $T_H2$ polarization by secreting factors such as IL-4 or thymic stromal lymphopoietin (TSLP; Ito et al., 2005; Oh et al., 2007; Sokol et al., 2008). However, MMP-2 neither induced production of IL-4 nor TSLP by human basophils (FIG. 12A-C). In addition, MMP-2 did not increase the expression of the basophil activation marker CD203c (Ocmant et al., 2007), further demonstrating that MMP-2 did not stimulate basophils (FIG. 12A).

We next evaluated whether DCs could be involved in the polarization of MMP-2-specific CD4+ T cells. Expression levels by DCs of maturation markers CD40, CD80, CD83, CD86, HLA-DR and CCR7 were not significantly affected by either active or inactive MMP-2.

Figure 6A:
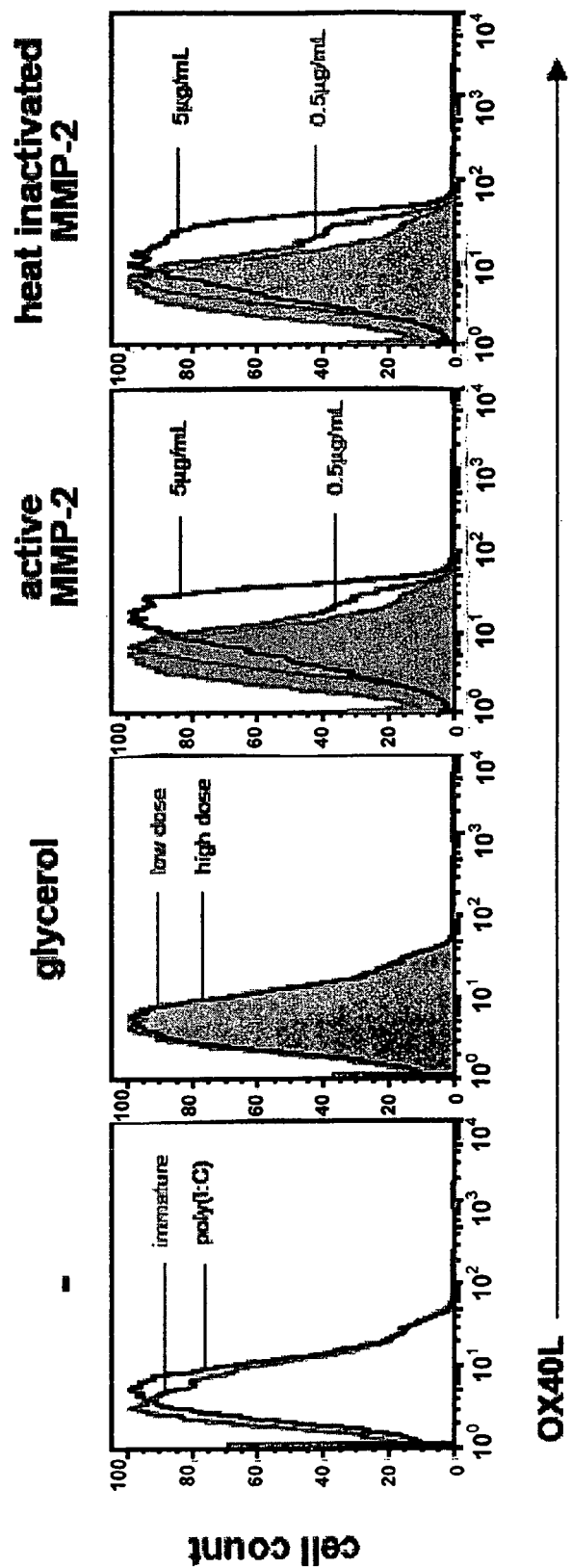
FIG. 6A-B shows MMP-2 protein induces OX40L expression on DCs. Immature and poly(I:C)-matured DCs were incubated with active or HI MMP-2 (0.5 μg/mL or 5 μg/mL) for 24 h. MMP-2 enzymatic activity was controlled (FIG. 13C-D). OX40L expression was assessed by surface staining (A) Histogram plots are shown for representative donor HD1228. Isotype control is represented in tinted gray. (B) Mean fluorescent intensities are represented for all 9 donors tested. For immature and mature DCs, paired t-tests were used to compare low and high values of glycerol, active MMP-2 and inactive MMP-2. P values≤0.0167 (*) were considered statistically significant using a Bonferroni correction for 3 comparisons for each DC type. See also FIG. 12.
Figure 6B:
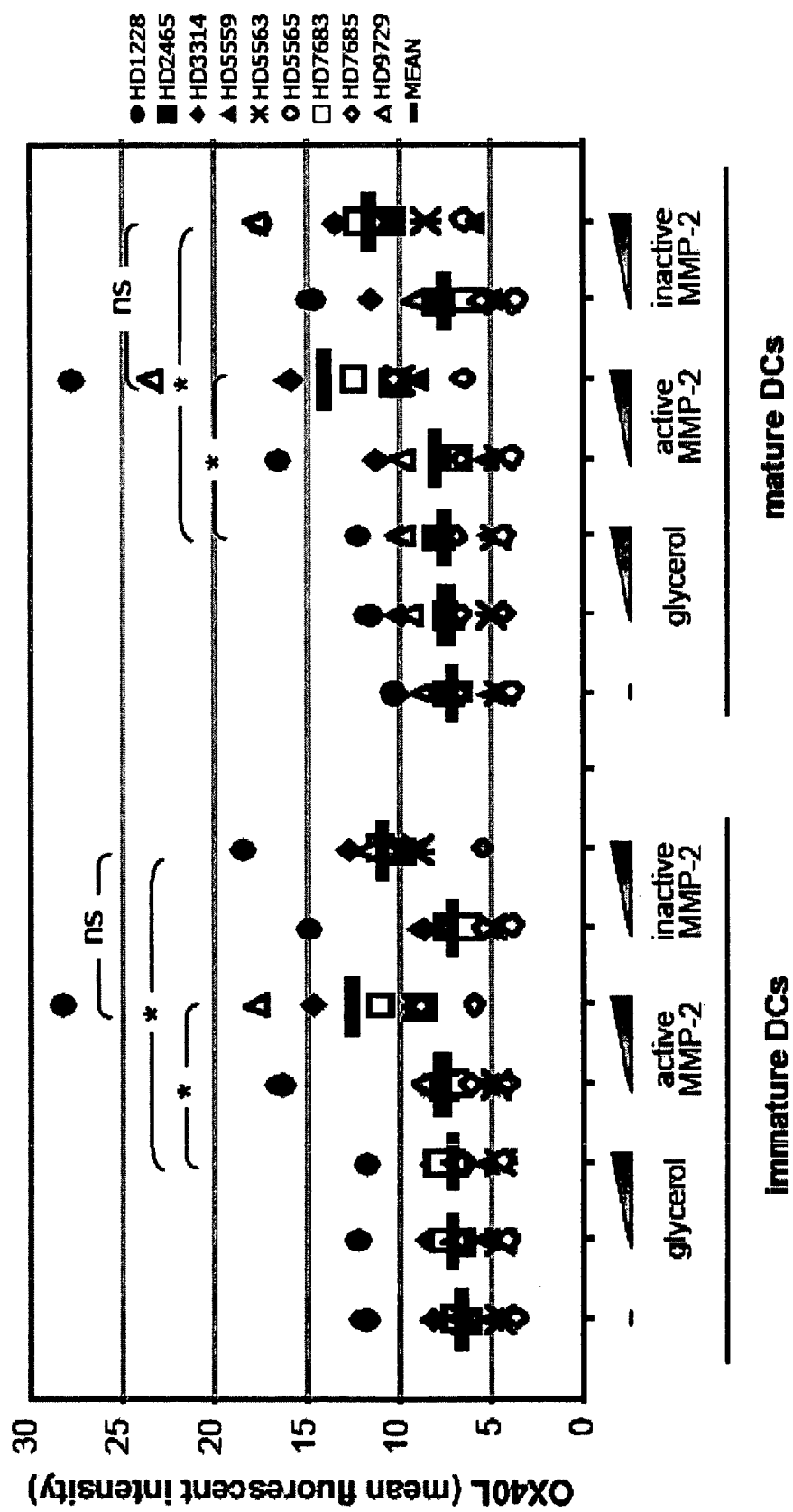

OX40L expressed on DCs can function as an inflammatory $T_H2$-skewing molecule (Ito et al., 2005). Both active and inactivated MMP-2 significantly increased OX40L expression on DCs (n=9), irrespective of their maturation stage (FIG. 6A-B). However, differentiation into inflammatory $T_H2$ cells required pre-exposure of DCs to MMP-2 in its active conformation only (FIG. 5), suggesting the involvement, in the polarization mechanism, of another molecule specifically sensitive to active MMP-2.

Inhibition of IL-12 Production by MMP-2

Figure 7A:
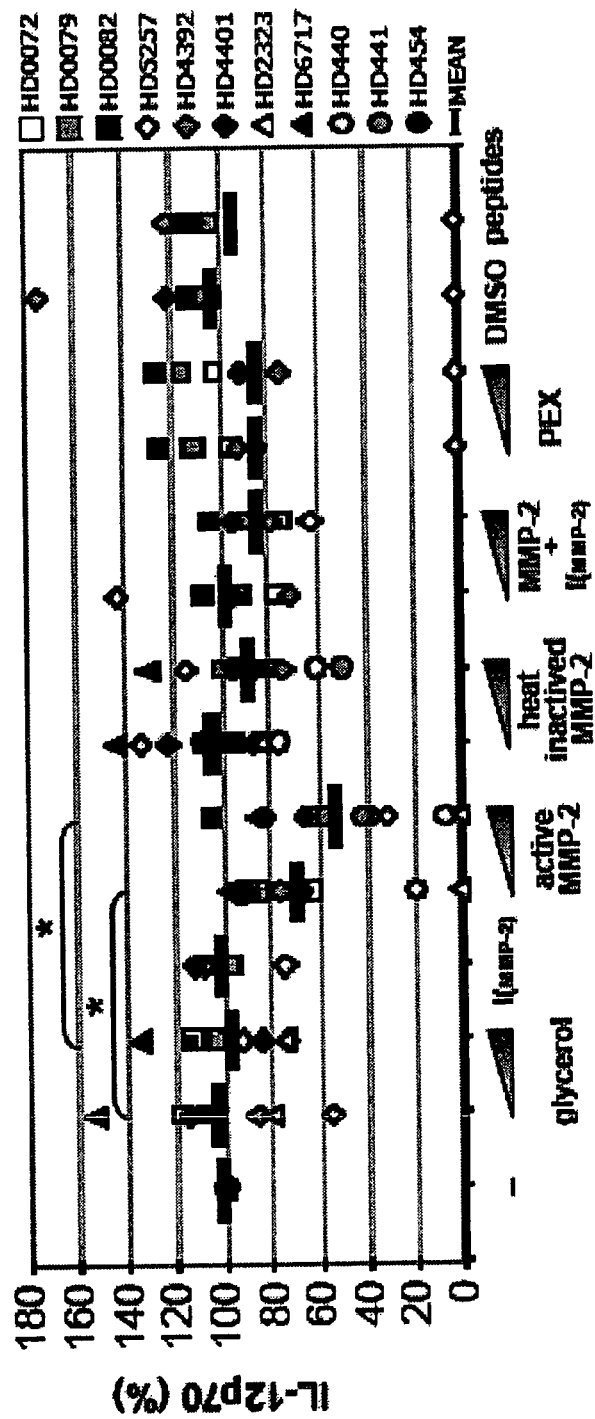
Figure 13B:
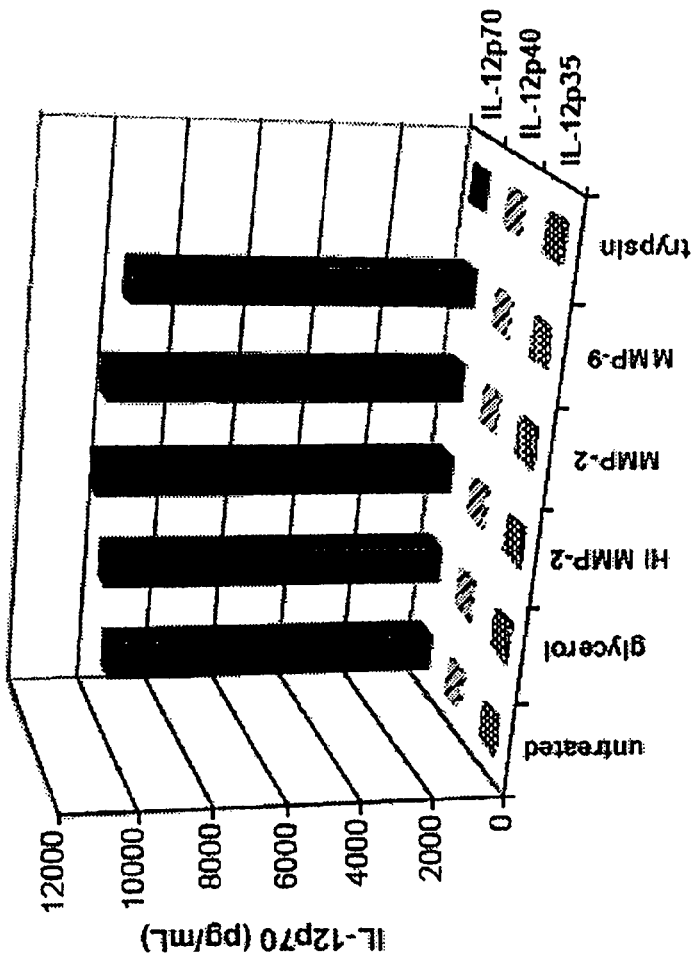
Figure 13A:
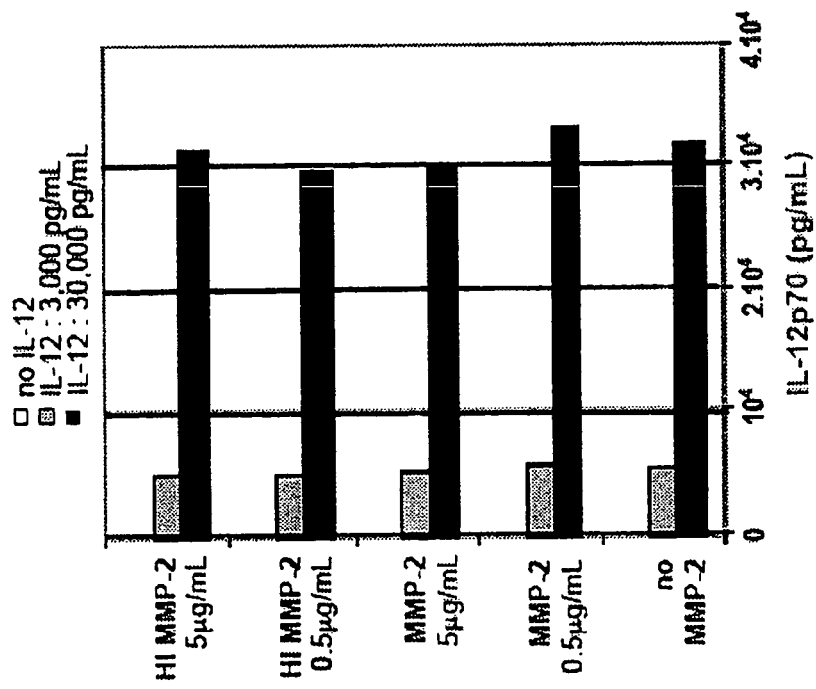
Figure 14:
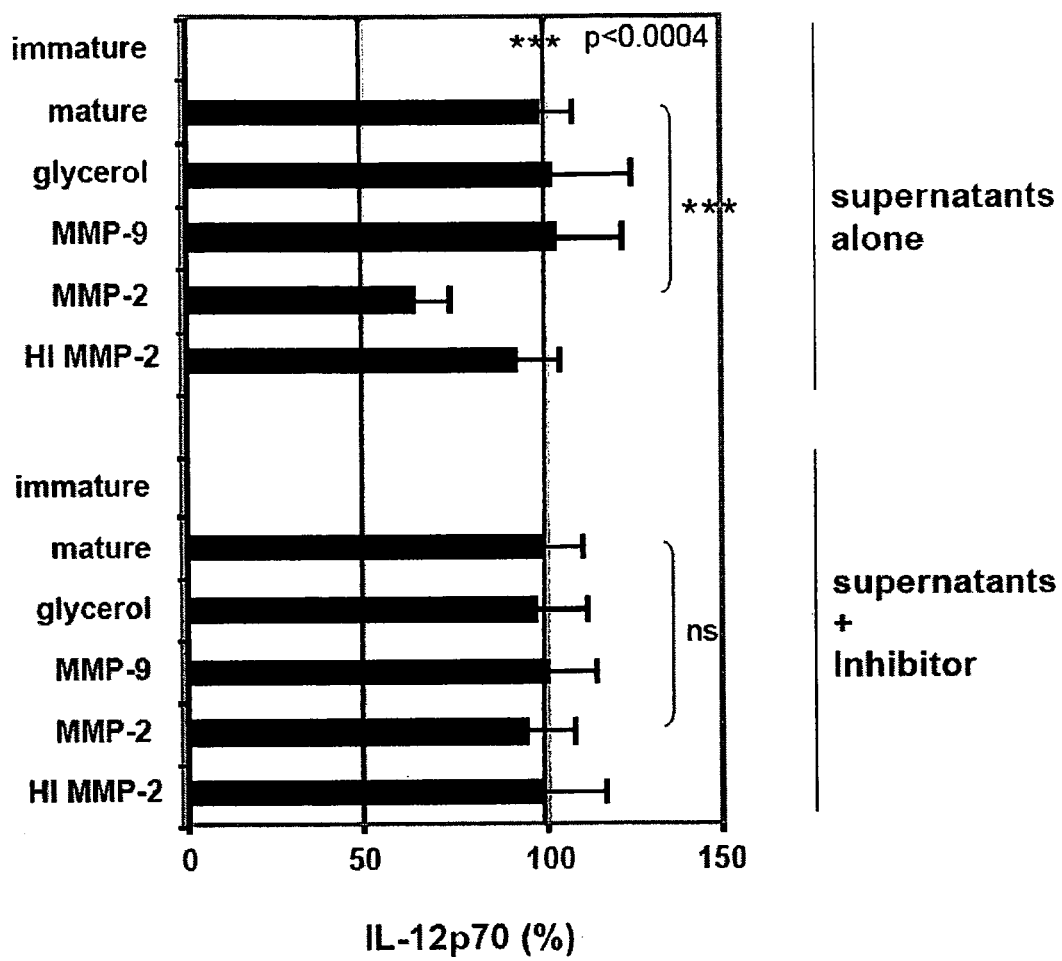
FIG. 14 shows that MMP-2 does not need a cleaved substrate to block IL-12 (related to FIG. 7). To determine whether MMP-2 directly affects DCs or cleaves substrates that subsequently affect DC, immature DCs were incubated for 16 h as indicated and supernatants were harvested and treated or not for 30 min with a MMP-2-specific inhibitor (100 nM). Supernatants (treated or not) were added on autologous DCs for 1 h before addition of poly(I:C). Sixteen hours later, IL-12p70 levels in supernatants were assessed by CBA. Supernatants containing the MMP-2-specific inhibitor did not affect IL-12p70 levels (p>0.24, relative to untreated activated DCs). On the other hand, IL-12p70 production by DCs was significantly inhibited when supernatants did not contain the MMP-2-inhibitor, as DCs secreted only 64.8% of IL-12p70, most likely due to residual active MMP-2. ***, p<0.0004; ns p≥0.05 (paired Student's t-test).

Importantly, MMP-2-treated DCs produced significantly less $T_H1$-associated IL-12p70 (47.8% mean inhibition with 5 μg/mL MMP-2; mean of differences=41.7 with $p \leq 0.001$, n=11 donors), in a dose-dependent manner, when stimulated with the TLR3 agonist poly(I:C). The reduction in IL-12 was not observed using inactivated MMP-2, MMP-2 peptides, rhPEX (190 amino acid long C-terminal fragment of MMP-2 lacking protease activity) or controls including glycerol (vehicle control for MMP-2), DMSO (peptides diluted in DMSO) and a MMP-2-specific inhibitor alone (FIG. 7A). To assess whether MMP-2 diminished IL-12p70 levels by inhibiting DC production/secretion or by directly degrading extracellular IL-12, we incubated rhIL-12 for 24 h in the presence or absence of MMP-2. IL-12p70 levels remained the same in every condition (FIG. 13A). Single chains IL-12p35 and IL-12p40 as well as trypsin-exposed IL-12p70 were not recognized by the CBA kit (FIG. 13B), confirming its specificity for bioactive IL-12p70 and therefore strongly suggesting that IL-12 was not a substrate for MMP-2 and that instead MMP-2 directly inhibited DCs to produce IL-12. MMP-2 activity was controlled by measuring its capacity to degrade MCP-3 (FIG. 13C). Furthermore, supernatants of MMP-2-exposed DCs did not affect IL-12p70 production by fresh DCs, suggesting that no cleaved part of a MMP-2 substrate is directly responsible for this effect (FIG. 14). Following poly(I:C) activation, 4.33%±0.94 DCs expressed the IL-12p35 subunit, whereas only 1.5%±0.22 expressed it when pre-incubated with active MMP-2 (FIG. 7B). Thus, pre-exposure to active MMP-2 reduces DC production of IL-12p35 (mean inhibition=65%), thereby preventing the formation of the bioactive IL-12p70. IL-12p40 production was not affected overall (FIG. 7B). Optimal IL-12p35 transcription is thought to depend on STAT1 activation in human moDCs (Gautier et al., 2005). As expected, STAT1 phosphorylation was decreased when DCs were preincubated with active ($p \leq 0.0047$), but not inactive, MMP-2 prior to poly(I:C) stimulation (FIG. 7C,D), suggesting that active MMP-2 inhibits IL-12p35 production by preventing STAT1 phosphorylation.

MMP-2 binds integrins such as αvβ3 (Brooks et al., 1996), αIIbβ3 (Choi et al., 2008), or other β2 integrins (Stefanidakis et al., 2003) and the scavenger receptor CD91 (Emonard et al., 2004), all of which are expressed on human DCs. We therefore tested whether MMP-2 signaled through such molecules to block IL-12 production and induce OX40L expression. PEX peptide, known to prevent MMP-2 binding to integrins such as αvβ3 (Brooks et al., 1998), and blocking mAbs specific for most of these receptors did not restore IL-12p70 production by MMP-2-exposed DCs, suggesting that other molecules may be involved.

Figure 7F:
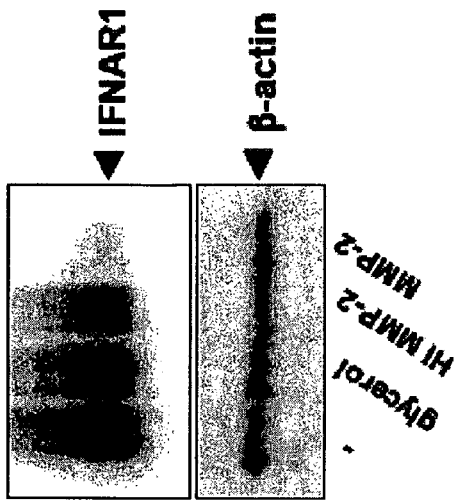
Figure 7H:
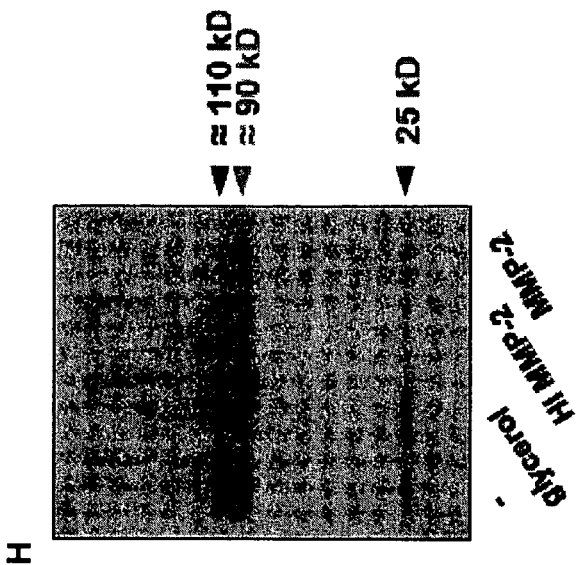
Figure 7E:
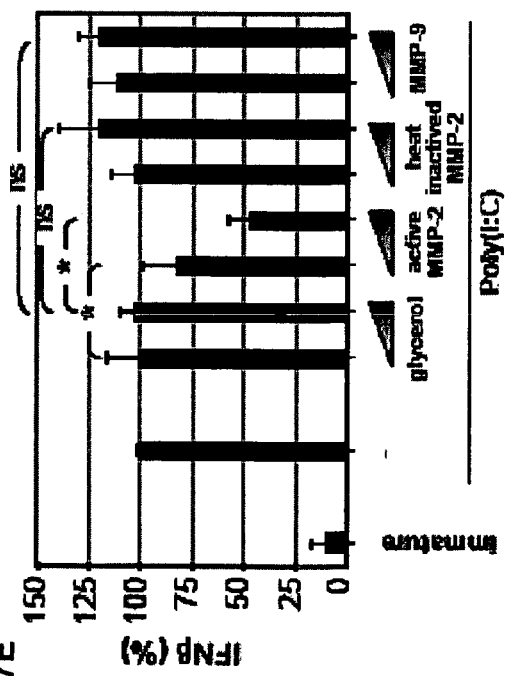
Figure 15:
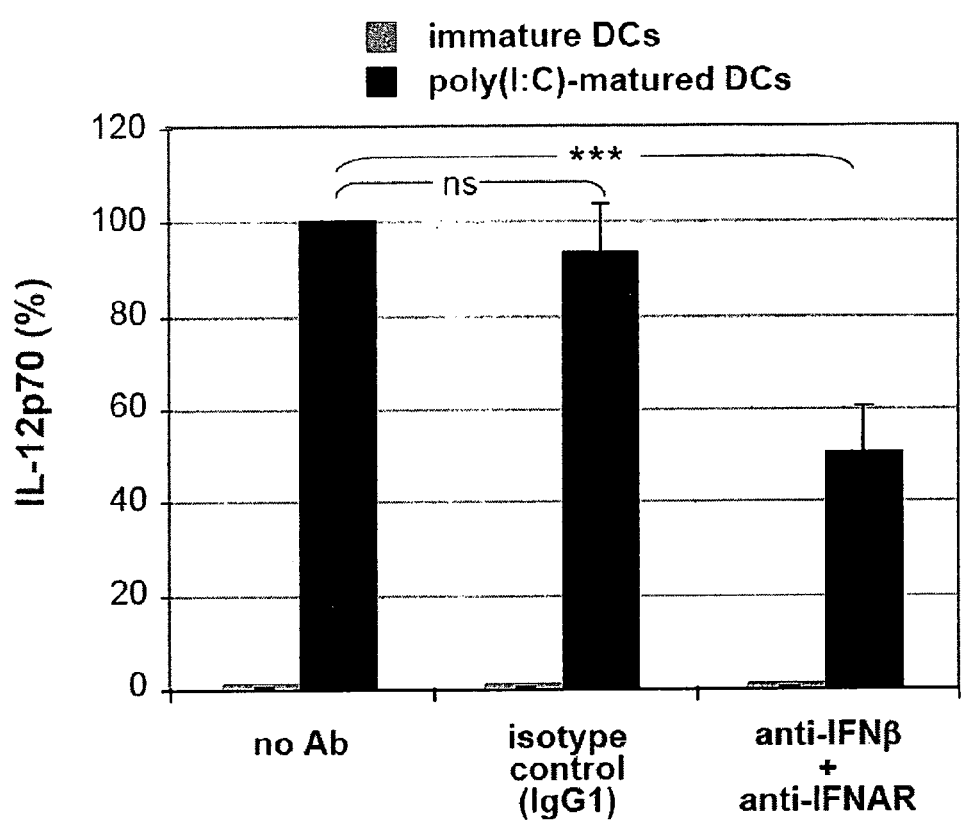
FIG. 15 shows IL-12 production depends on IFNβ/IFNAR signaling (related to FIG. 7). DCs were incubated with indicated antibodies at 10 μg/mL. Poly(I:C) (5 μg/mL/10⁶DCs) was added after 30 min IL-12p70 levels were measured 16 h later by CBA (Myltenyi) and are represented as a percentage of IL-12p70 levels produced when DCs were incubated with poly(I:C) alone (n=3 donors). ***, p<0.02; ns, non significant (paired Student's t-test).

STAT1 phosphorylation (Severa et al., 2006) and subsequent IL-12 production (Gautier et al., 2005) can be induced by type-I IFN receptor triggering. We confirmed that IFNβ induced IL-12p70 production, as blocking mAbs to IFNβ and its receptor significantly inhibited IL-12p70 production and with a similar magnitude as MMP-2 (FIG. 15). We consequently tested involvement of this cytokine and its receptor in our system. IFNβ signaling through its receptor leads to STAT1 phosphorylation (Severa et al., 2006), which triggers IL-12p35 transcription and enhanced transcription of IFNβ itself through an amplification loop (Decker et al., 2005; Gautier et al., 2005). Accordingly, Poly (I:C)-matured DCs pre-exposed to active MMP-2 produced decreased levels of IFNβ (FIG. 7E). Strikingly, we found that MMP-2-exposed DCs drastically lost expression of IFNAR1 chain of the receptor for type-I IFNs (n=7 donors, p≤0.001) (FIG. 7F,G). Furthermore, recombinant rhIFNAR1 (≈110 kD) incubated overnight with active MMP-2 was degraded by MMP-2 (FIG. 7H). Therefore, MMP-2 cleaves IFNAR1 on DCs leading to loss of IL-12 production through reduction of STAT1 phosphorylation.

In summary, both active and inactive MMP-2 induce OX40L expression by DCs while active MMP-2 inhibits IL-12p35 production, and subsequent IL-12p70 formation by degrading IFNAR1, a previously unidentified substrate for MMP-2.

Figure 8A:
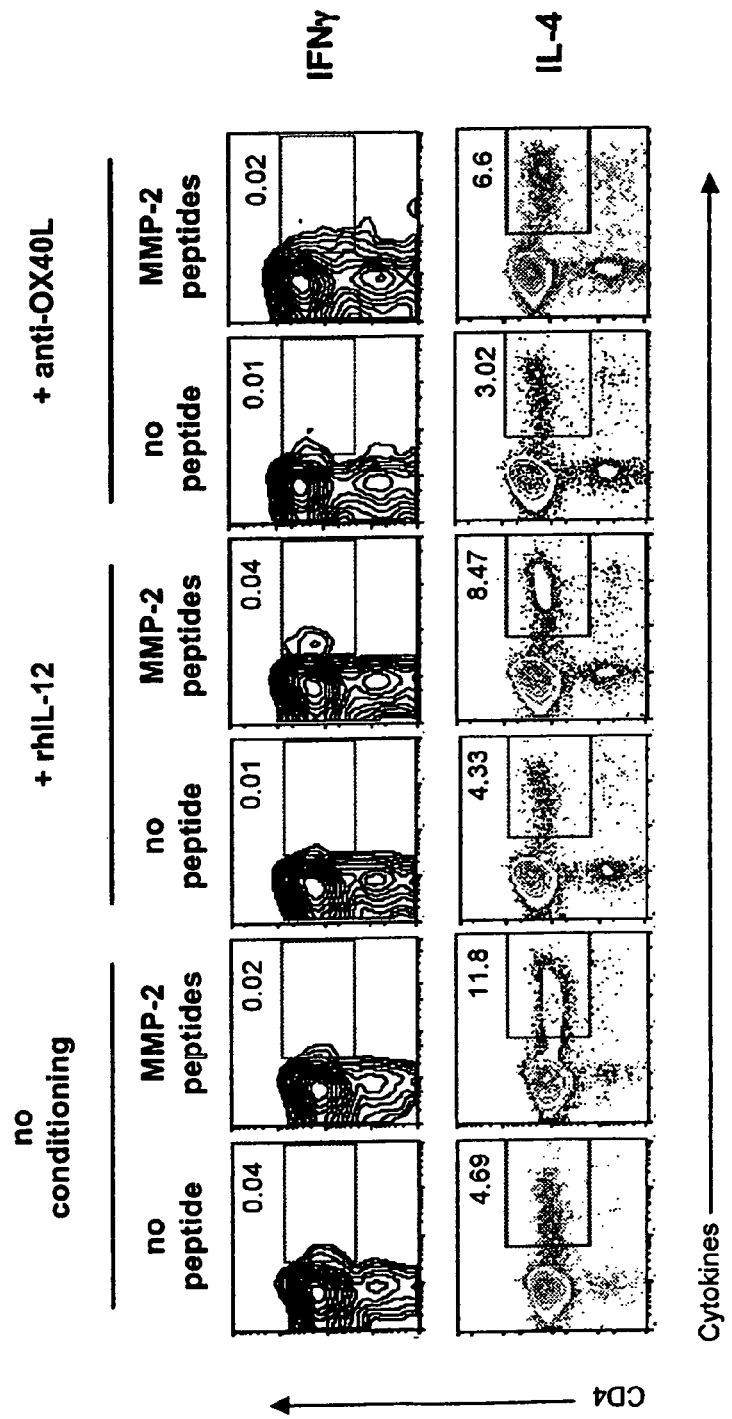
FIG. 8A-B shows MMP-2-specific CD4+ T cell differentiation depends on IL-12 and OX40L expression by DCs. (A) Cord blood-derived CD4+/CD25− cells from 19 donors were stimulated with autologous DCs previously loaded with active MMP-2 (MMP-2 enzymatic activity was controlled (FIG. 13C-D)) for 15 days in the absence or in the presence of exogenous rhIL-12 (10 ng/mL) or blocking mAb for OX40L or IL-4 (10 μg/mL). CD4+ T cells were then stimulated with the MMP-2 peptide pool (2 μM) for 6 h before intracellular staining of cytokines. Contour plots representing cytokine production by CD4+ T cells are shown for donor CB31 CD4+ T cells primed to MMP-2 alone, or together with rhIL-12, anti-OX40L mAb or anti-IL-4 mAb. (B) Percentages of MMP-2-specific CD4+ T cells, secreting indicated cytokines, are represented for all donors. For each cytokine, 5 paired t-tests were used to compare "no conditioning" versus various conditions. P values≤0.01 (*) were considered statistically significant using a Bonferroni correction for 5 comparisons.
Figure 8B:
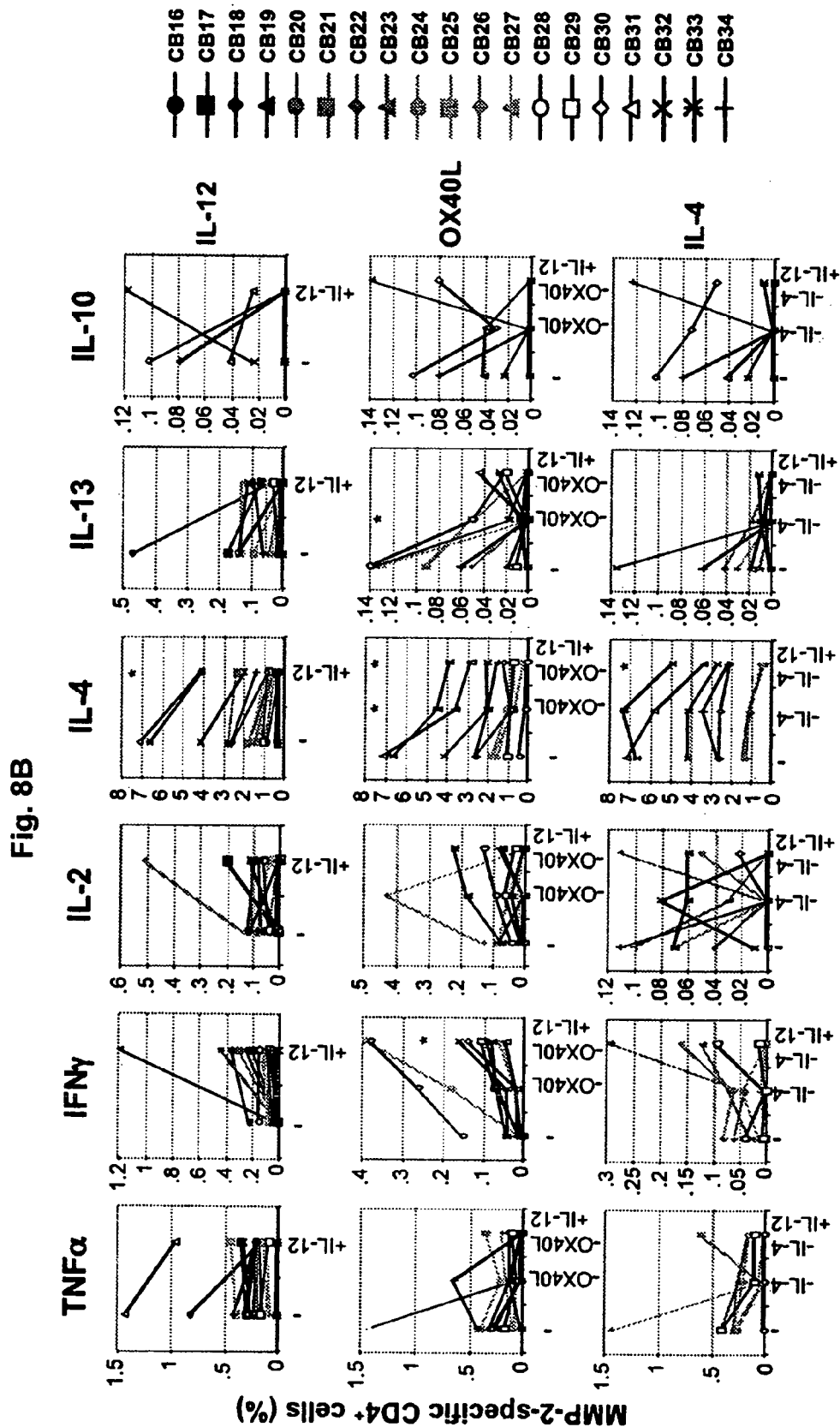

MMP-2-Specific CD4$^+$ T Cell Differentiation Depends on IL-12 and OX40L Expression by DCs During Priming To test whether OX40L and/or IL-12 are directly responsible for inflammatory $T_H2$ polarization of MMP-2-specific T cells, naïve CD4$^+$ T cells from 19 cord blood donors were primed by autologous poly(I:C)-matured DCs pulsed with the active MMP-2 protein. As expected, primed MMP-2-specific CD4$^+$ T cells secreted IL-4 and TNFα corresponding to the inflammatory $T_H2$ phenotype observed so far. However, when exogenous rhIL-12 was added throughout priming, MMP-2-specific T cells partially reverted their phenotype towards a $T_H1$-like profile, i.e. secreting less IL-4 (p≤0.0001; n=19) and more IFNγ (p=0.022; n=19). These results are consistent with the concept that lack of IL-12 is critical for inflammatory $T_H2$ differentiation of MMP-2-specific CD4$^+$ T cells (FIG. 8A-B). When naïve T cells were primed in the presence of anti-OX40L, MMP-2-specific cells secreted less IL-4 (p≤0.003; n=10) and more IFNγ (p=0.023; n=10) than CD4$^+$ T cells primed without additional IL-12 (FIG. 8A-B). Addition of both rhIL-12 and anti-OX40L during priming triggered MMP-2-specific CD4$^+$ T cells secreting less IL-4 (p≤0.002; n=10) and more IFNγ (p≤0.006; n=10) than anti-OX40L alone (FIG. 8B), indicating that both molecules are involved in MMP-2-specific CD4+ T cell polarization.

IL-4 is critical for $T_H2$ differentiation in many models (Sokol et al., 2008; Swain et al., 1990). We next primed naïve MMP-2-specific CD4+ T cells to active MMP-2 while blocking potential DC-derived IL-4 with a specific mAb. Primed cells maintained an identical inflammatory $T_H2$ phenotype (n=8) (FIG. 8B), confirming that, in this $T_H2$ differentiation model, IL-4 is not a major determinant Therefore, inflammatory $T_H2$ polarization of MMP-2-specific T cells is dependent upon both IL-12 and OX40L, but not on IL-4.

In summary, data presented herein show that MMP-2 induces priming of $T_H2$ inflammatory CD4$^+$ T cells, by diminishing IL-12 production (through degradation of type-1 IFN receptor) and inducing OX40L expression by DCs. To the best of our knowledge, these properties render MMP-2, the first human endogenous type-2 conditioner to be described.

Discussion

The first two subsets described of effector CD4$^+$ T cells were the $T_H1$ and $T_H2$ subpopulations (Mosmann and Coffman, 1989). Both cells were shown to mediate anti-cancer functions (Nishimura et al., 1999), but IFNγ-secreting $T_H1$ cells appeared to be superior in inducing memory cytotoxic responses and strong cellular immunity (Nishimura et al., 2000). $T_H1$ cells are characterized by their production of IFNγ and, to a lesser extent, IL-2. IL-12 produced by APCs, particularly activated DCs, as well as IFNγ produced by NK cells and T cells, polarize CD4$^+$ T cells toward the $T_H1$ cell differentiation program through STAT1 and T-bet (Szabo et al., 2000). In contrast, $T_H2$ cells mediate host defense against extracellular parasites, including helminthes and are important in the induction and persistence of allergic diseases. Conventional $T_H2$ cells are classically defined as producers of IL-4, IL-5, IL-10 and IL-13, but the mechanism(s) underlying induction of $T_H2$ differentiation has remained unclear.

IL-4, by inducing GATA-3 expression, is usually described as essential for $T_H2$ differentiation (Sokol et al., 2008; Swain et al., 1990). Cellular sources of IL-4 for $T_H2$ differentiation have not been clearly established. Granulocytes such as basophils readily produce IL-4 after crosslinking of their FcεR1 receptors and have been proposed to be responsible for $T_H2$ differentiation in several models (Falcone et al., 1996; Sokol et al., 2008). MMP-2 did not activate basophils (assessed by IL-4 and TSLP production as well as CD203c expression (FIG. 12A-C)), suggesting these cells were not involved in this model. Moreover, MMP-2-induced type-2 differentiation does not appear to depend on IL-4 since naïve MMP-2-specific CD4$^+$ T cells primed in the presence or in the absence of a blocking antibody specific for IL-4 gave rise to type-2 CD4$^+$ T cells with a similar profile (FIG. 8A-B). This observation is in accordance with accumulating in vivo studies indicating that, in some settings, IL-4 is not essential for $T_H2$ differentiation (Everts et al., 2009; Jankovic et al., 2000; Steinfelder et al., 2009). A default mechanism could also explain $T_H2$ differentiation, where the lack of $T_H1$-polarizing signal, namely IL-12, would be sufficient and/or necessary (Minkis et al., 2008; Moser and Murphy, 2000). We found that active MMP-2 inhibited IL-12 production by DCs (FIG. 7A-B), which was in part responsible for the MMP-2-induced type-2 polarization. Indeed, supplementing the priming cultures of MMP-2-specific CD4$^+$ T cells with rhIL12, even at doses as low as 1 ng/mL, induced lower percentages of IL4-secreting T cells and more IFNγ-secreting cells (FIG. 8A-B).

TSLP leads to $T_H2$ cell recruitment and allergic inflammation (Liu et al., 2007). Basophils (Sokol et al., 2008), epithelial cells (Soumelis and Liu, 2004) or DCs (Ito et al., 2005; Liu, 2006; Watanabe et al., 2004) can be sources of TSLP. TSLP contributes to $T_H2$ immunity by inhibiting $T_H1$ differentiation, by acting directly on T cells to promote $T_H2$ differentiation, or by activating DCs or a combination of the above. Stimulation of DCs with TSLP, in the absence of IL-12, induces upregulation of the costimulatory molecule OX40L and can promote differentiation of naive T cells into cells that secrete IL-4, IL-5, IL-13 and TNFα. Cells exhibiting these features are referred to as inflammatory $T_H2$ cells (Ito et al., 2005; Soumelis et al., 2002). MMP-2-specific CD4$^+$ T cells secrete IL-4, IL-13 and TNFα, but no IL-10, consistent with such an inflammatory $T_H2$ profile. Interestingly, MMP-2 did not activate basophils to secrete TSLP (nor IL-4) (FIG. 12). On the other hand, MMP-2 induced DCs to express OX40L (FIG. 6A-B), in a TSLP-independent manner. We showed that inflammatory $T_H2$ differentiation of MMP-2-specific cells also relied on OX40L expression (FIG. 8A-B). OX40 signaling in CD4$^+$ T cells can directly induce type-2 lineage commitment by inducing NFATc1, which triggers IL-4 production and subsequent GATA-3 expression (So et al., 2006; Yu et al., 2009). MMP-2-induced type-2 differentiation likely works differently as we showed that IL-4 was not a major determinant in this model. Of note, addition of both rhIL-12 and anti-OX40L blocking mAb during priming induced MMP-2-specific CD4$^+$ T cells that secrete significantly less IL-4 and more IFNγ than anti-OX40L alone (FIG. 8B), indicating that both molecules are involved in MMP-2-induced type-2 differentiation by triggering additive effects.

Figure 7G:
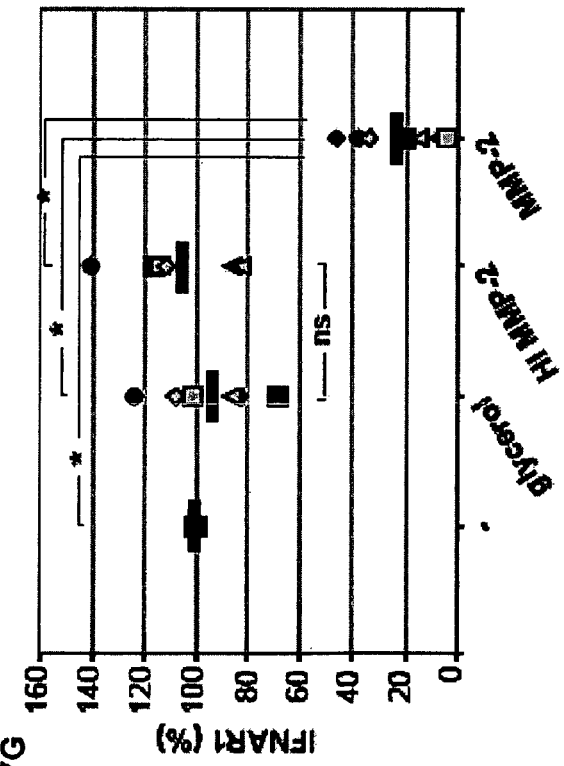

We found that MMP-2 degrades IFNAR1 (FIG. 7F-H), constituting one chain of the heterodimeric type-I IFN receptor. The IFNAR1 chain, described here for the first time as a novel substrate for MMP-2, is essential for signaling (Decker et al., 2005). When cleaved, the type-I IFN amplification loop is abrogated, explaining the reduction of IFNβ secreted by MMP-2-exposed DCs (FIG. 7E). Type-I IFN receptor signaling triggers STAT1 phosphorylation (Severa et al., 2006), which in turn also induces IL-12p35 transcription (Gautier et al., 2005). As a result, bioactive IL-12p70 formation is inhibited and cannot exert its function in $T_H1$ differentiation. Through this mechanism, MMP-2 acts as a novel endogenous type-2 "conditioner".

TNF$^+$/IL10$^-$ $T_H2$ cells are thought to represent the pathogenic $T_H2$ cells that cause allergic inflammation, in contrast to the conventional IL-10-producing cells. Many potent allergens have intrinsic protease activity (Grobe et al., 1999; Kheradmand et al., 2002) and secreted proteases are essential for the infectious and reproductive cycles of helminths (McKerrow et al., 2006). Recent studies showed that the T2 ribonuclease derived from soluble egg antigens of the parasitic helminth *Schistosoma* triggers potent $T_H2$ responses by conditioning mouse DCs (Everts et al., 2009; Steinfelder et al., 2009). One can speculate that the innate immune system might have evolved a mechanism to detect abnormal proteases associated with helminth infection that could then be triggered by other proteases, such as allergens or in this case MMP-2. Our results clearly showed for the first time that an enzyme-induced $T_H2$-conditioning directly resides in the intrinsic enzymatic activity rather than solely in the active conformation of MMP-2.

MMP-2 also acts as a type-2 conditioner for CD4$^+$ T cells recognizing other MAA (FIG. 5A-B), indicating that MMP-2 plays a dominant role in biasing the response against otherwise $T_H1$ inducing tumor antigens. Our in vitro results suggest that increased MMP-2 secretion may locally influence the induction of immune responses and skew them towards type-2 responses. Accordingly, MMP-2-specific CD4$^+$ T cell responses tended to be found in TILs from patients exhibiting a poorer clinical outcome (FIG. 9B). MMP-2 might therefore partially explain the observed prevalence, at least in some studies, of detrimental type-2 responses in various cancers including melanoma.

Our findings collectively support the idea that the pro-tumoral MMP-2 protein represents a good candidate to target in immunotherapy to treat melanoma patients, since it can induce both broad CD4$^+$ and CD8$^+$ T cell responses. Furthermore, elucidation of mechanisms underlying $T_H2$ polarization, including the one identified in this study, opens the way to designing immune strategies for inducing effective antitumor $T_H1$-like responses to treat cancer patients.

REFERENCES

Botella-Estrada, R., Escudero, M., O'Connor, J. E., Nagore, E., Fenollosa, B., Sanmartin, O., Requena, C., and Guillen, C. (2005). Cytokine production by peripheral lymphocytes in melanoma. Eur Cytokine Netw 16, 47-55.

Brooks, P. C., Silletti, S., von Schalscha, T. L., Friedlander, M., and Cheresh, D. A. (1998). Disruption of angiogenesis by PEX, a noncatalytic metalloproteinase fragment with integrin binding activity. Cell 92, 391-400.

Brooks, P. C., Stromblad, S., Sanders, L. C., von Schalscha, T. L., Aimes, R. T., Stetler-Stevenson, W. G., Quigley, J. P., and Cheresh, D. A. (1996). Localization of matrix metalloproteinase MMP-2 to the surface of invasive cells by interaction with integrin alpha v beta 3. Cell 85, 683-693.

Choi, W. S., Jeon, O. H., Kim, H. H., and Kim, D. S. (2008). MMP-2 regulates human platelet activation by interacting with integrin alphaIIbbeta3. J Thromb Haemost 6, 517-523.

Coulie, P. G., and van der Bruggen, P. (2003). T-cell responses of vaccinated cancer patients. Curr Opin Immunol 15, 131-137.

Decker, T., Muller, M., and Stockinger, S. (2005). The yin and yang of type I interferon activity in bacterial infection. Nat Rev Immunol 5, 675-687.

Dreno, B., Nguyen, J. M., Khammari, A., Pandolfino, M. C., Tessier, M. H., Bercegeay, S., Cassidanius, A., Lemarre, P., Billaudel, S., Labarriere, N., et al. (2002). Randomized trial of adoptive transfer of melanoma tumor-infiltrating lymphocytes as adjuvant therapy for stage III melanoma. Cancer Immunol Immunother 51, 539-546.

Emonard, H., Bellon, G., Troeberg, L., Berton, A., Robinet, A., Henriet, P., Marbaix, E., Kirkegaard, K., Patthy, L., Eeckhout, Y., et al. (2004). Low density lipoprotein receptor-related protein mediates endocytic clearance of pro-MMP-2.TIMP-2 complex through a thrombospondin-independent mechanism. J Biol Chem 279, 54944-54951.

Everts, B., Perona-Wright, G., Smits, H. H., Hokke, C. H., van der Ham, A. J., Fitzsimmons, C. M., Doenhoff, M. J., van der Bosch, J., Mohrs, K., Haas, H., et al. (2009). Omega-1, a glycoprotein secreted by *Schistosoma mansoni* eggs, drives Th2 responses. J Exp Med 206, 1673-1680.

Falcone, F. H., Dahinden, C. A., Gibbs, B. F., Noll, T., Amon, U., Hebestreit, H., Abrahamsen, O., Klaucke, J., Schlaak, M., and Haas, H. (1996) Human basophils release interleukin-4 after stimulation with *Schistosoma mansoni* egg antigen. Eur J Immunol 26, 1147-1155.

Gautier, G., Humbert, M., Deauvieau, F., Scuiller, M., Hiscott, J., Bates, E. E., Trinchieri, G., Caux, C., and Garrone, P. (2005). A type I interferon autocrineparacrine loop is involved in Toll-like receptor-induced interleukin-12p70 secretion by dendritic cells. J Exp Med 201, 1435-1446.

Godefroy, E., Moreau-Aubry, A., Diez, E., Dreno, B., Jotereau, F., and Guilloux, Y. (2005). alpha v beta3-dependent cross-presentation of matrix metalloproteinase-2 by melanoma cells gives rise to a new tumor antigen. J Exp Med 202, 61-72.

Godefroy, E., Scotto, L., Souleimanian, N. E., Ritter, G., Old, L. J., Jotereau, F., Valmori, D., and Ayyoub, M. (2006).

Identification of two Melan-A CD4+ T cell epitopes presented by frequently expressed MHC class II alleles. Clin Immunol 121, 54-62.

Godefroy, E., Wang, Y., Souleimanian, N. E., Scotto, L., Stevanovic, S., Chen, Y. T., Valmori, D., and Ayyoub, M. (2007). Assessment of CD4+ T cells specific for the tumor antigen SSX-1 in cancer-free individuals. Cancer Immunol Immunother 56, 1183-1192.

Grobe, K., Becker, W. M., Schlaak, M., and Petersen, A. (1999). Grass group I allergens (beta-expansins) are novel, papain-related proteinases. Eur J Biochem 263, 33-40.

Hirohashi, Y., Torigoe, T., Inoda, S., Kobayasi, J., Nakatsugawa, M., Mori, T., Hara, I., and Sato, N. (2009). The functioning antigens: beyond just as the immunological targets. Cancer Sci 100, 798-806.

Ito, T., Wang, Y. H., Duramad, O., Hori, T., Delespesse, G. J., Watanabe, N., Qin, F. X., Yao, Z., Cao, W., and Liu, Y. J. (2005). TSLP-activated dendritic cells induce an inflammatory T helper type 2 cell response through OX40 ligand. J Exp Med 202, 1213-1223.

Itoh, T., Tanioka, M., Yoshida, H., Yoshioka, T., Nishimoto, H., and Itohara, S. (1998). Reduced angiogenesis and tumor progression in gelatinase A-deficient mice. Cancer Res 58, 1048-1051.

Jankovic, D., Kullberg, M. C., Noben-Trauth, N., Caspar, P., Paul, W. E., and Sher, A. (2000). Single cell analysis reveals that IL-4 receptor/Stat6 signaling is not required for the in vivo or in vitro development of CD4+ lymphocytes with a Th2 cytokine profile. J Immunol 164, 3047-3055.

Kessenbrock, K., Plaks, V., and Werb, Z. (2010). Matrix metalloproteinases: regulators of the tumor microenvironment. Cell 141, 52-67.

Khammari, A., Nguyen, J. M., Pandolfino, M. C., Quereux, G., Brocard, A., Bercegeay, S., Cassidanius, A., Lemarre, P., Volteau, C., Labarriere, N., et al. (2007). Longterm follow-up of patients treated by adoptive transfer of melanoma tumor-infiltrating lymphocytes as adjuvant therapy for stage III melanoma. Cancer Immunol Immunother 56, 1853-1860.

Kheradmand, F., Kiss, A., Xu, J., Lee, S. H., Kolattukudy, P. E., and Corry, D. B. (2002). A protease-activated pathway underlying Th cell type 2 activation and allergic lung disease J Immunol 169, 5904-5911.

Labarriere, N., Pandolfino, M. C., Gervois, N., Khammari, A., Tessier, M. H., Dreno, B., and Jotereau, F. (2002). Therapeutic efficacy of melanoma-reactive TIL injected in stage III melanoma patients. Cancer Immunol Immunother 51, 532-538.

Lauerova, L., Dusek, L., Simickova, M., Kocak, I., Vagundova, M., Zaloudik, J., and Kovarik, J. (2002). Malignant melanoma associates with Th1/Th2 imbalance that coincides with disease progression and immunotherapy response. Neoplasma 49, 159-166.

Liotta, L. A., Tryggvason, K., Garbisa, S., Hart, I., Foltz, C. M., and Shafie, S. (1980). Metastatic potential correlates with enzymatic degradation of basement membrane collagen. Nature 284, 67-68.

Liu, Y. J. (2006). Thymic stromal lymphopoietin: master switch for allergic inflammation. J Exp Med 203, 269-273.

Liu, Y. J., Soumelis, V., Watanabe, N., Ito, T., Wang, Y. H., Malefyt Rde, W., Omori, M., Zhou, B., and Ziegler, S. F. (2007). TSLP: an epithelial cell cytokine that regulates T cell differentiation by conditioning dendritic cell maturation. Annu Rev Immunol 25, 193-219.

Loose, D., and Van de Wiele, C. (2009). The immune system and cancer. Cancer Biother Radiopharm 24, 369-376.

McCarter, M., Clarke, J., Richter, D., and Wilson, C. (2005). Melanoma skews dendritic cells to facilitate a T helper 2 profile. Surgery 138, 321-328.

McKerrow, J. H., Caffrey, C., Kelly, B., Loke, P., and Sajid, M. (2006). Proteases in parasitic diseases. Annu Rev Pathol 1, 497-536.

Minkis, K., Kavanagh, D. G., Alter, G., Bogunovic, D., O'Neill, D., Adams, S., Pavlick, A., Walker, B. D., Brockman, M. A., Gandhi, R. T., et al. (2008). Type 2 Bias of T cells expanded from the blood of melanoma patients switched to type 1 by IL-12p70 mRNA-transfected dendritic cells. Cancer Res 68, 9441-9450.

Moser, M., and Murphy, K. M. (2000). Dendritic cell regulation of TH1-TH2 development. Nat Immunol 1, 199-205.

Mosmann, T. R., and Coffman, R. L. (1989). TH1 and TH2 cells: different patterns of lymphokine secretion lead to different functional properties. Annu Rev Immunol 7, 145-173.

Nishimura, T., Iwakabe, K., Sekimoto, M., Ohmi, Y., Yahata, T., Nakui, M., Sato, T., Habu, S., Tashiro, H., Sato, M., et al. (1999). Distinct role of antigen-specific T helper type 1 (Th1) and Th2 cells in tumor eradication in vivo. J Exp Med 190, 617-627.

Nishimura, T., Nakui, M., Sato, M., Iwakabe, K., Kitamura, H., Sekimoto, M., Ohta, A., Koda, T., and Nishimura, S. (2000). The critical role of Th1-dominant immunity in tumor immunology. Cancer Chemother Pharmacol 46 Suppl, S52-61.

Ocmant, A., Peignois, Y., Mulier, S., Hanssens, L., Michils, A., and Schandene, L. (2007). Flow cytometry for basophil activation markers: the measurement of CD203c up-regulation is as reliable as CD63 expression in the diagnosis of cat allergy. J Immunol Methods 320, 40-48.

Oh, K., Shen, T., Le Gros, G., and Min, B. (2007). Induction of Th2 type immunity in a mouse system reveals a novel immunoregulatory role of basophils. Blood 109, 2921-2927.

Rosenberg, S. A. (2004). Shedding light on immunotherapy for cancer. N Engl J Med 350, 1461-1463.

Severa, M., Remoli, M. E., Giacomini, E., Ragimbeau, J., Lande, R., Uze, G., Pellegrini, S., and Coccia, E. M. (2006). Differential responsiveness to IFN-alpha and IFN-beta of human mature DC through modulation of IFNAR expression. J Leukoc Biol 79, 1286-1294.

So, T., Song, J., Sugie, K., Altman, A., and Croft, M. (2006). Signals from OX40 regulate nuclear factor of activated T cells c1 and T cell helper 2 lineage commitment. Proc Natl Acad Sci USA 103, 3740-3745.

Sokol, C. L., Barton, G. M., Farr, A. G., and Medzhitov, R. (2008). A mechanism for the initiation of allergen-induced T helper type 2 responses. Nat Immunol 9, 310-318.

Sokol, C. L., Chu, N. Q., Yu, S., Nish, S. A., Laufer, T. M., and Medzhitov, R. (2009). Basophils function as antigen-presenting cells for an allergen-induced T helper type 2 response. Nat Immunol 10, 713-720.

Soumelis, V., and Liu, Y. J. (2004). Human thymic stromal lymphopoietin: a novel epithelial cell-derived cytokine and a potential key player in the induction of allergic inflammation. Springer Semin Immunopathol 25, 325-333.

Soumelis, V., Reche, P. A., Kanzler, H., Yuan, W., Edward, G., Homey, B., Gilliet, M., Ho, S., Antonenko, S., Lauerma, A., et al. (2002) Human epithelial cells trigger dendritic cell mediated allergic inflammation by producing TSLP. Nat Immunol 3, 673-680.

Stefanidakis, M., Bjorklund, M., Ihanus, E., Gahmberg, C. G., and Koivunen, E. (2003). Identification of a negatively charged peptide motif within the catalytic domain of progelatinases that mediates binding to leukocyte beta 2 integrins. J Biol Chem 278, 34674-34684.

Steinfelder, S., Andersen, J. F., Cannons, J. L., Feng, C. G., Joshi, M., Dwyer, D., Caspar, P., Schwartzberg, P. L., Sher, A., and Jankovic, D. (2009). The major component in schistosome eggs responsible for conditioning dendritic cells for Th2 polarization is a T2 ribonuclease (omega-1). J Exp Med 206, 1681-1690.

Swain, S. L., Weinberg, A. D., English, M., and Huston, G. (1990). IL-4 directs the development of Th2-like helper effectors. J Immunol 145, 3796-3806.

Szabo, S. J., Kim, S. T., Costa, G. L., Zhang, X., Fathman, C. G., and Glimcher, L. H. (2000). A novel transcription factor, T-bet, directs Th1 lineage commitment. Cell 100, 655-669.

Tatsumi, T., Kierstead, L. S., Ranieri, E., Gesualdo, L., Schena, F. P., Finke, J. H., Bukowski, R. M., Mueller-Berghaus, J., Kirkwood, J. M., Kwok, W. W., et al. (2002). Disease-associated bias in T helper type 1 (Th1)/Th2 CD4 (+) T cell responses against MAGE-6 in HLA-DRB10401 (+) patients with renal cell carcinoma or melanoma. J Exp Med 196, 619-628.

Watanabe, N., Hanabuchi, S., Soumelis, V., Yuan, W., Ho, S., de Waal Malefyt, R., and Liu, Y. J. (2004). Human thymic stromal lymphopoietin promotes dendritic cell-mediated CD4+ T cell homeostatic expansion. Nat Immunol 5, 426-434.

Westermarck, J., and Kahari, V. M. (1999). Regulation of matrix metalloproteinase expression in tumor invasion. Faseb J 13, 781-792.

Yee, C., Thompson, J. A., Roche, P., Byrd, D. R., Lee, P. P., Piepkorn, M., Kenyon, K., Davis, M. M., Riddell, S. R., and Greenberg, P. D. (2000). Melanocyte destruction after antigen-specific immunotherapy of melanoma: direct evidence oft cell-mediated vitiligo. J Exp Med 192, 1637-1644.

Yu, Q., Sharma, A., Oh, S. Y., Moon, H. G., Hossain, M. Z., Salay, T. M., Leeds, K. E., Du, H., Wu, B., Waterman, M. L., et al. (2009). T cell factor 1 initiates the T helper type 2 fate by inducing the transcription factor GATA-3 and repressing interferon-gamma. Nat Immunol 10, 992-999.

What is claimed is:

1. A method for monitoring and assessing immune response to a matrix metalloproteinase-2 (MMP-2) expressing tumor comprising assessing enhanced cell mediated responses to MMP-2, the method comprising: inducing enhanced cell mediated immune responses by contacting at least one of CD4+$T_H$1 cells and dendritic cells with at least one MMP-2 peptide, wherein the at least one MMP-2 peptide consists of 20-25 contiguous amino acids of SEQ ID NO: 1 comprising amino acids 601-620 of SEQ ID NO: 1 (P601-620), amino acids 621-640 of SEQ ID NO: 1 (P621-640), or amino acids 630-650 of SEQ ID NO: 1 (P630-650); or a composition comprising the at least one MMP-2 peptide and detecting an increase in at least one of MMP-2-specific CD4+ $T_H$1 cells and dendritic cells expressing type-I IFN receptor (IFNAR1), wherein the increase is indicative of the immune response to the MMP-2 expressing tumor.

2. The method of claim 1, wherein the MMP-2 expressing tumor is melanoma, breast cancer, colon cancer, gastric cancer, lung cancer, ovarian cancer, pancreatic cancer, prostate cancer, or squamous cell carcinoma of the head and neck.

3. The method of claim 1, wherein the MMP-2 expressing tumor is a melanoma.

4. The method of claim 1, wherein the MMP-2 peptide is associated with or covalently attached to a polycationic or cell penetrating peptide to promote cellular uptake or delivery.

5. The method of claim 4, wherein the polycationic or cell penetrating peptide is a Tat peptide comprising the sequence RKKRRQRRR (SEQ ID NO: 27).

6. The method of claim 1, wherein dendritic cells are targeted for cellular uptake or delivery of the at least one MMP-2 peptide or the composition comprising the at least one MMP-2 peptide.

7. The method of claim 1, wherein induction of MMP-2-specific CD4+$T_H$2 cells is inhibited.

8. The method of claim 1, wherein the inducing is performed in a subject.

9. The method of claim 8, wherein the subject is a mammalian subject.

10. The method of claim 9, wherein the mammalian subject is a human.

11. The method of claim 1, wherein the at least one MMP-2 peptide consists of the amino acids 601-620 of SEQ ID NO: 1, the amino acids 621-640 of SEQ ID NO: 1, or the amino acids 630-650 of SEQ ID NO: 1.

* * * * *